US011464784B2

(12) United States Patent
Kurtz et al.

(10) Patent No.: US 11,464,784 B2
(45) Date of Patent: Oct. 11, 2022

(54) INHIBITION OF AMINOCYLASE 3 (AA3) IN THE TREATMENT OF CANCER

(71) Applicant: THE REGENTS OF THE UNIVERSITY OF CALIFORNIA, Oakland, CA (US)

(72) Inventors: Ira B Kurtz, Los Angeles, CA (US); Alexander Pushkin, Los Angeles, CA (US); Kirill B. Tsirulnikov, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 75 days.

(21) Appl. No.: 16/646,975

(22) PCT Filed: Sep. 14, 2018

(86) PCT No.: PCT/US2018/051146
§ 371 (c)(1),
(2) Date: Mar. 12, 2020

(87) PCT Pub. No.: WO2019/055825
PCT Pub. Date: Mar. 21, 2019

(65) Prior Publication Data
US 2020/0206239 A1 Jul. 2, 2020

Related U.S. Application Data

(60) Provisional application No. 62/559,170, filed on Sep. 15, 2017.

(51) Int. Cl.
| *A61K 31/5415* | (2006.01) |
| *A61P 31/00* | (2006.01) |
| *A61P 35/00* | (2006.01) |
| *A61K 31/18* | (2006.01) |
| *A61K 31/26* | (2006.01) |
| *A61K 31/366* | (2006.01) |
| *A61K 31/4184* | (2006.01) |
| *A61K 31/429* | (2006.01) |
| *A61K 31/4439* | (2006.01) |
| *A61K 31/519* | (2006.01) |
| *A61K 31/7105* | (2006.01) |
| *A61K 45/06* | (2006.01) |

(52) U.S. Cl.
CPC .......... *A61K 31/5415* (2013.01); *A61K 31/18* (2013.01); *A61K 31/26* (2013.01); *A61K 31/366* (2013.01); *A61K 31/4184* (2013.01); *A61K 31/429* (2013.01); *A61K 31/4439* (2013.01); *A61K 31/519* (2013.01); *A61K 31/7105* (2013.01); *A61P 31/00* (2018.01); *A61P 35/00* (2018.01); *A61K 45/06* (2013.01)

(58) Field of Classification Search
None
See application file for complete search history.

(56) References Cited

U.S. PATENT DOCUMENTS

| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,196,265 A | 4/1980 | Croce et al. |
| 4,275,149 A | 6/1981 | Litman et al. |
| 4,277,437 A | 7/1981 | Maggio |
| 4,352,799 A * | 10/1982 | Renson ................ C07D 293/12 514/183 |
| 4,366,241 A | 12/1982 | Tom et al. |
| 4,469,797 A | 9/1984 | Albarella |
| 4,472,509 A | 9/1984 | Gansow et al. |
| 4,703,003 A | 10/1987 | Struck |
| 4,706,855 A | 11/1987 | Litwin |
| 4,742,159 A | 5/1988 | Batz et al. |
| 4,767,720 A | 8/1988 | Lingwood |
| 4,816,567 A | 3/1989 | Cabilly et al. |
| 4,867,973 A | 9/1989 | Goers et al. |
| 4,938,948 A | 7/1990 | Ring et al. |
| 4,946,778 A | 8/1990 | Ladner et al. |
| 5,021,236 A | 6/1991 | Gries et al. |
| 5,091,513 A | 2/1992 | Huston et al. |
| 5,164,296 A | 11/1992 | Blaustein et al. |
| 5,196,066 A | 3/1993 | Kusuda et al. |

(Continued)

FOREIGN PATENT DOCUMENTS

| WO | 2008040441 | 4/2008 |
| WO | 2012087908 | 6/2012 |

(Continued)

OTHER PUBLICATIONS

Roehrl et al., Biochemistry (2004), 43(51), pp. 16067-16075.*
International Preliminary Report on Patentability for International Application No. PCT/US2016/033923, Report dated Nov. 28, 2017, 9 Pgs.
International Preliminary Report on Patentability for International Application No. PCT/US2018/051146, Report dated Mar. 17, 2020, dated Mar. 26, 2020, 7 Pgs.
International Search Report and Written Opinion for International Application No. PCT/US2016/033923, Search completed Nov. 21, 2016, dated Nov. 21, 2016, 14 Pgs.
Anders et al., "Aminoacylases", Adv. Pharmacol, 1994, vol. 27, pp. 431-448.

(Continued)

*Primary Examiner* — Brian J Davis
(74) *Attorney, Agent, or Firm* — Norton Rose Fulbright US LLP

(57) ABSTRACT

The current methods and compositions provide for therapeutic approaches to treating hepatocellular carcinoma (HCC) and other types of cancer including, for example, pancreatic and colon cancer. Accordingly, certain aspects of the disclosure relates to methods and compositions for treating HCC, pancreatic and colon cancer using one or more small molecule inhibitors disclosed herein. In certain embodiments, the small molecule inhibitor is a benzothiazine, a sulfonamide, a thiazolidinone or other chemical compound.

24 Claims, 30 Drawing Sheets

(56) References Cited

U.S. PATENT DOCUMENTS

| | | | |
|---|---|---|---|
| 5,223,409 | A | 6/1993 | Ladner et al. |
| 5,403,484 | A | 4/1995 | Ladner et al. |
| 5,420,253 | A | 5/1995 | Emery et al. |
| 5,565,332 | A | 10/1996 | Hoogenboom et al. |
| 5,571,698 | A | 11/1996 | Ladner et al. |
| 5,627,052 | A | 5/1997 | Schrader |
| 5,656,434 | A | 8/1997 | Terano et al. |
| 5,770,376 | A | 6/1998 | Bagrov |
| 5,789,208 | A | 8/1998 | Sharon |
| 5,821,337 | A | 10/1998 | Carter et al. |
| 5,844,091 | A | 12/1998 | Blaustein et al. |
| 5,858,657 | A | 1/1999 | Winter et al. |
| 5,861,155 | A | 1/1999 | Lin |
| 5,871,907 | A | 2/1999 | Winter et al. |
| 5,969,108 | A | 10/1999 | Mccafferty et al. |
| 6,054,297 | A | 4/2000 | Carter et al. |
| 6,165,464 | A | 12/2000 | Hudziak et al. |
| 6,365,157 | B2 | 4/2002 | Rockwell et al. |
| 6,406,867 | B1 | 6/2002 | Yu et al. |
| 6,709,659 | B1 | 3/2004 | Lok et al. |
| 6,709,873 | B1 | 3/2004 | Yatscoff et al. |
| 6,753,407 | B2 | 6/2004 | Noga et al. |
| 6,814,965 | B2 | 11/2004 | Gao et al. |
| 6,849,259 | B2 | 2/2005 | Haurum et al. |
| 6,861,572 | B1 | 3/2005 | Etches et al. |
| 6,875,434 | B1 | 4/2005 | Schenk |
| 6,881,557 | B2 | 4/2005 | Foote |
| 6,891,024 | B2 | 5/2005 | Marsh |
| 6,946,546 | B2 | 9/2005 | Vaughan et al. |
| 7,067,676 | B2 | 6/2006 | Dell et al. |
| 8,487,077 | B2 | 7/2013 | Olma et al. |
| 9,556,206 | B2 | 1/2017 | Toutov et al. |
| 2010/0248371 | A1 | 9/2010 | Connell et al. |
| 2011/0257233 | A1 | 10/2011 | Cosford et al. |
| 2016/0015709 | A1 | 1/2016 | Cheresh et al. |

FOREIGN PATENT DOCUMENTS

| | | |
|---|---|---|
| WO | 2016191424 | 12/2016 |
| WO | 2019055825 | 3/2019 |

OTHER PUBLICATIONS

Baum et al., "Lithium-silylindolide als Precursor fur 1, 2-, 1,3-Bis(silyl)indole and Bis(indol-1,3-yl)silane", Zeitschrift fur Anorganische und Allgemeine Chemie, 1999, vol. 625, No. 12, pp. 1969-1978.
Beier et al., "Synthesis of SF5-containing benzisoxazoles, quinolines, and quinazolines by the Davis reaction of nitro-(pentafluorosulfanyl)benzenes", Beilstein J. Org. Chem., Feb. 21, 2013, vol. 9, pp. 411-416.
Bentinger et al., "Phosphorylation of farnesol in rat liver microsomes: properties of farnesol kinase and farnesyl phosphate kinase", Arch. Biochem. Biophys., 1998, vol. 353, pp. 191-198.
Bernard-Gauthier et al., BioMed Research Int., Jul. 24, 2014, 20.
Boroughs et al., "Metabolic pathways promoting cancer cell survival and growth", Nat. Cell Biology, 2015, vol. 17, pp. 351-359.
Bos, "Ras oncogenes in human cancer: a review", Cancer Research, 1989, vol. 49, pp. 4682-4689.
Braun et al., "Reactivity of a palladium fluoro complex towards silanes and Bu3SnCH=CH2: catalytic derivatisation of penlafluoropyridine based on carbon-fluorine bond activation reactions", Dalton Transactions, 2006, pp. 5118-5123.
Buhaescu et al., "Mevalonate pathway: A review of clinical and therapeutical implications", Clin. Biochem, 2007, vol. 40, pp. 575-584.
Cai et al., J. Nucl. Med., Feb. 2007, vol. 48, pp. 304-310.
Calle et al., "Synthesis and Reactions of Silylated and Stannylated 1,2-Azoles", Synthesis, 2001, No. 13, pp. 1949-1958.
Campbell et al., "Increasing complexity of Ras signaling", Oncogene, 1998, vol. 17, pp. 1395-1413.

Champagne et al., Paquin, J.-F. Chem Rev., Apr. 9, 2015, vol. 115, pp. 9073-9174.
Cheng et al., J. Nucl. Med., 2008, vol. 49: 804.
Chetty et al., "KRAS", Journal of Clinical Pathology, 2013, vol. 66, pp. 548-550.
Chung et al., "Overexpression and oncogenic function of adloketo reductase family B10 (ARK1B10) in pancreatic carcinoma", Mod. Pathol. 2012, vol. 25, pp. 758-766.
Cox et al., "Drugging the undruggable RAS: Mission possible?", Nat. Rev. Drug Discovery, 2014, vol. 13, pp. 828-851.
Cox et al., "Targeting RAS membrane association: back to the future for anti-RAS drug discovery?", Clin. Cancer Res., 2015, vol. 21, pp. 1819-1827.
Dialer et al., "Studies toward the development of new silicon-containing building blocks for the direct 18F-labeling of peptides", Journal of Medicinal Chemistry, 2013, vol. 56, No. 19, pp. 7552-7563.
Downward, "Targeting RAS signaling pathways in cancer therapy", Nat. Rev. Cancer, 2003, vol. 3, pp. 11-22.
El-Serag, "Hepaatocellular carcinoma", New England Journal of Medicine, 2011, vol. 365, pp. 1118-1127.
Endo, "N-acyl-l-aromatic amino acid deacylase in animal tissues", Biochim. Biophys. Acta, 1978, vol. 523, pp. 207-214.
Frenzel et al., "Indolyl- and Pyrrolylsilanes—Syntheses and Crystal Structures", Zeitschrift fur Naturforschung B, 1995, vol. 50, No. 11, pp. 1658-1664.
Frenzel et al., "New Routes to 1,2- and 1,3-Bis(silyl)indoles-Synthesis of the first Bis(indol-3-yl)silane", Main Group Chemistry, 1996, vol. 1, pp. 399-408.
Gao et al., "CAAX-box protein, prenylation and process and carcinogenesis,", Am. j. Transl. Res, 2009, vol. 1, pp. 312-325.
Hobbs et al., "RAS isoforms and mutations in cancer at a glance", J. Cell. Sci., 2016, vol. 129, pp. 1287-1292.
Hollingworth et al., Chem. Commun., 2012, vol. 48, pp. 2929-2942.
Huang et al., "Oncogenic K-Ras requires activation for enhanced activity", Oncogene, 2014, vol. 33, pp. 532-535.
Jacobson et al., Bioconjugate Chem., Feb. 21, 2011, vol. 22, pp. 422-428.
Jacobson et al., "Fluorine-18 Radiochemistry, Labeling Strategies and Synthetic Routes", Bioconjugate Chem., 2015, vol. 26, pp. 1-18.
Jana et al., "Crown Ether Nucleophilic Catalysts (CENCs): Agents for Enhanced Silicon Radiofluorination", J. Org. Chem., Feb. 7, 2017, vol. 82, pp. 2329-2335.
Kang, "Cross-coupling and carbonylative cross-coupling of organofluorosilanes with hypervalent iodonium Tetrafluoroborates", Tetrahedron, 1997, vol. 53, Issue 9, pp. 3027-3034.
Klingebiel et al., "Mono-, Bis-, Tris- und Tetrakis(indol-1-yl)silane", Journal of Organometallic Chemistry, 1993, vol. 55, pp. 51-55.
Konstantinopoulos et al., "Post-translational modifications and regulation of the RAS Supervamily of GTPases as anticancer targets", Nat. Rev. Drug Discovery, 2007, vol. 6, pp. 541-555.
Kostikov et al., Nature Protocols, 2012, vol. 7, pp. 1956-1963.
Lee et al., "A Fluoride-Derived Electrophilic Late-Stage Fluorination Reagent for PET Imaging", Science, Nov. 4, 2011, vol. 334, pp. 639-642.
Liang et al., Angew. Chem. Int. Ed., Aug. 5, 2013, vol. 52, pp. 8214-8264.
Liu et al., Mol. Imaging, 2011, 10:168.
Lowy et al., "Function and regulation of Ras", Annu Ref. Biochem, 1993, vol. 62, pp. 851-891.
Masaoka et al., "The synthesis of chlorosilanes from alkoxysilanes, silanols, and hydrosilanes with bulky substituents", Journal of Organometallic Chemistry, 2006, vol. 691, pp. 174-181.
McCormick, "KRAS as a therapeutic traget", Clinical Cancer Res.. 2015, vol. 21, pp. 1797-1801.
McCormick, "K-Ras protein as a drug target", Journal of Molecular Medicine (Berl), 2016, vol. 94, pp. 253-258.
Mosmann, "Rapid colorimetric assay for cellular growth and survival: application to proliferation and cytotoxicity assays", J. Immunol. Methods, 1983, vol. 65, pp. 55-63.

(56) References Cited

OTHER PUBLICATIONS

Mu et al., "Silicon-Based Building Blocks for One-Step 18F-Radiolabeling of Peptides for PET Imaging", Angew. Chem. Int. Ed., 2008, vol. 47, pp. 4922-4925.

Mullen et al., "The interplay between celll signaling and the mevalonate pathway in cancer", Nat. Rev. Cancer, 2016, vol. 16, pp. 718-731.

Neugebauer et al., "Silylfurans and Bis(sily)butadiyes—Synthesis, Lithium Derivatives, Crystal Structure", Zeitschrift für Naturforschung B, Oct. 1, 2000, vol. 55, Issue 10, pp. 913-923.

Newman et al., "Specificty of aminoacylase III-mediated deacetylation of mercapturic acids", Drug M et al. Dispos., 2007, vol. 35, pp. 43-50.

Olafsen et al., Tumor Biol., 2012, vol. 33:669.

Pasca Di Magliano et al., "Roles for KRAS in pancreatic tumor development and progression", Gastroentherol, 2013, vol. 144, pp. 1220-1229.

Phelps, "Positron emission tomography provides molecular imaging of biological processes", PNAS, Aug. 1, 2000, vol. 97, No. 16, pp. 9226-9233.

Ryan et al., "Targeting RAS-mutant cancers: is ERK the key?", Trends Cancer, 2015, vol. 1, pp. 183-198.

Sangiovanni et al., "Increased survival of cirrohotic patients with a hapatocellulor carcinoma detected during surveillance", Gastroenterology, 2004, vol. 126, pp. 1005-1014.

Shaw et al., "PI(3)K and mTOR signaling controls tumour cell growth", Nature, 2006, vol. 441, pp. 424-430.

Suzuki et al., "Purification and characterization of a rat liver enzyem catalyzing n-deactylation of mercapturic acid conjugates", Drug Metal. Dispos., 1981, vol. 9, pp. 573-577.

Svensson et al., "Genetic and pharmacologic analyses of the role of Icmt in Ras membrane association and vunction", Methods Enzymol. 2006, vol. 407, pp. 144-159.

Teufel et al., "Genetics of heptocellular carcinoma", World J. Gastroentrol., 2007, vol. 13, pp. 2271-2282.

Ting et al., J. Am. Chem. Soc., Sep. 1, 2005, vol. 127, No. 38, pp. 13094-13095.

Ting et al., "Arylfluoroborates and Alkylfluorosilicates as Potential PET Imaging Agents: High-Yielding Aqueous Biomolecular 18F-Labeling", J. Am. Chem. Soc., May 19, 2005, vol. 127, pp. 13094-13095.

Toutov, "Alkaline salts of sodium and potassium: from C-X reduction to C—H functionalization and beyond", Thesis, Sep. 26, 2016, California Institute of Technology, 696 pgs.

Toutov et al., "Sodium Hydroxide Catalyzed Dehydrocoupling of Alcohols with Hydrosilanes", Org. Lett., Nov. 9, 2016, vol. 18, pp. 5776-5779.

Toutov et al., "Alkali Metal-Hydroxide-Catalyzed C(sp)—H Bond silylation", Journal of the American Chemical Society, Jan. 1, 2017, vol. 1394, pp. 1668-1674, doi: 10.1021/jacs.6b12114.

Toutov et al., "Silylation of C—H bonds in aromatic heterocycles by an Earth-abundant metal catalyst", Nature, Feb. 5, 2015, vol. 518, pp. 80-84.

Uttamsingh et al., "Acylase-catalyzed deacetylation of haloalkene-derived meracapturates", Chem. Res. Toxicol., 1999, vol. 12, pp. 937-942.

Villanueva et al., "Targeted therapies for heptaocillular carcinoma", Gastronterology, 2011, vol. 140, pp. 141-1426.

Wangler et al., Bioconjug Chem., Dec. 15, 2010, vol. 21, No. 12, pp. 2289-2296.

Wangler et al., "Kil-Like 18F-Labeling of Proteins: Synthesis of 4-(Di-tertbutyl[18F]fluorosilyl)benzenethiol (Si[18F] FA-SH) Labeled Rat Serum Albumin for Blood Pool Imaging with PET", Bioconjugate Chemistry, 2009, vol. 20, pp. 317-321.

Wangler et al., Appl. Sci., Mar. 28, 2012, vol. 2, pp. 277-302.

Whyte et al., "K- and N-Ras are Geranygeranylated in Cells Treated with Farnesyl Protein Transferase Inhibitors", J. Biol. Chem., 1997, vol. 272, pp. 14459-14464.

Wong et al., "Molecular pathogenesis of heptaocellular carcinoma", Liver Int., 2008, vol. 28, pp. 160-174.

Wu et al., Curr Pharm Biotechnol., Sep. 1, 2010, vol. 11, No. 6, pp. 572-580.

Zhang et al., "Protein prenylation: molecular mechanisms and functional consequences.", Annu. Ref. Biochem., 1996, vol. 65, pp. 241-269.

Zhang et al., "The renewed battle against RAS-mutant cancers", Cell. Mol. Life. Sci., 2016, vol. 73, pp. 1845-1858.

Zhou et al., "Systematic review with network meta-analysis: statins and risk of hepatocellular carcinoma", Oncogarget, 2016, vol. 7, pp. 21753-21762.

Gueraud, "4-Hydroxynonenal Metabolites and Adducts in Pre-Carcinogenic Conditions and Cancer," Free Radical Biology and Medicine, 111: 196-208, 2017.

Hsieh, et al., "Structures of Aminoacylase 3 in Complexwith Acetylated Substrates," PNAS, 107: 17962-17967, 2010.

International Search Report and Written Opinion Issued in Corresponding PCT Patent Application No. PCT/US2018/051146, dated Feb. 15, 2019.

Long, et al., "Differential Aminoacylase Experssion in Neuroblastoma," Int J Cancer, 129, 1322-1330, 2011.

Pushkin, et al., "Structural Characterization, Tissue Distribution, and Functional Expression of Murine Aminoacylase III," Am J of Physiol, 286: C848-C856, 2004.

Tsirulnikov, et al., "Inhibition of Aminoacylase 3 Protects Rat brain Cortex Neuronal Cells From Toxicity of 4-Hydroxy-2-Nonenal Mercapturate and 4-Hydroxy-2-Nonenal," Toxicol Appl Pharmacol, 263: 303-314, 2012.

Tsirulnikov, et al., "Mouse Aminoacylase 3: A Metalloenzyme Activated by Cobalt and Nickel," *Biochim Biophys Acta*, 1794: 1049-1057, 2009.

\* cited by examiner

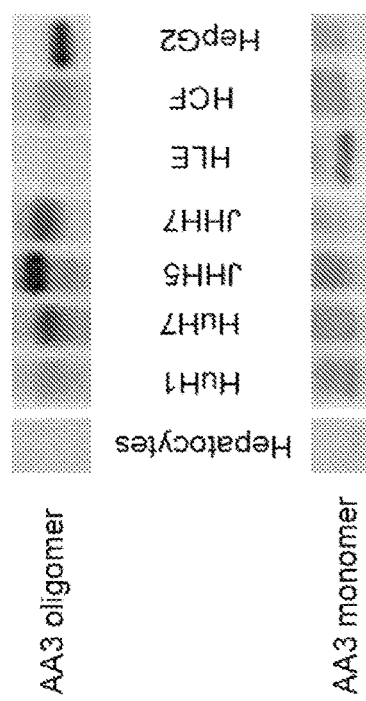
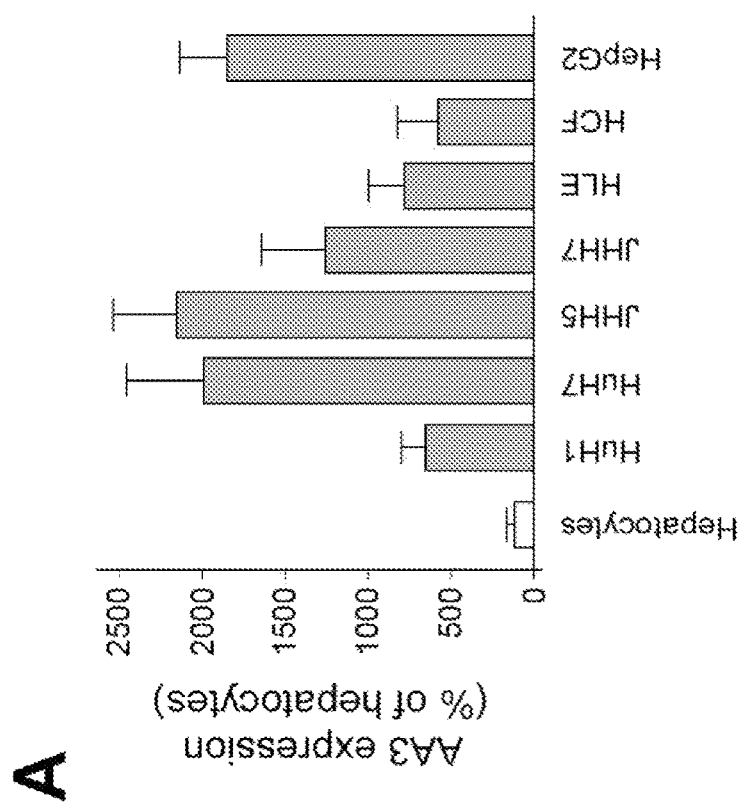
FIG. 1

Normal 1
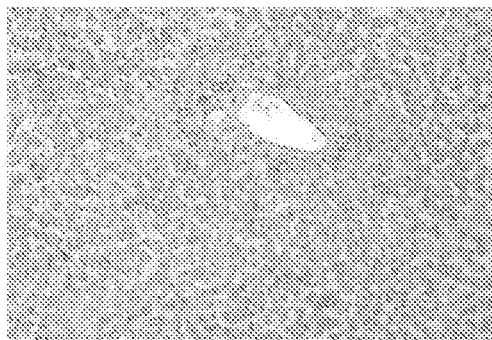 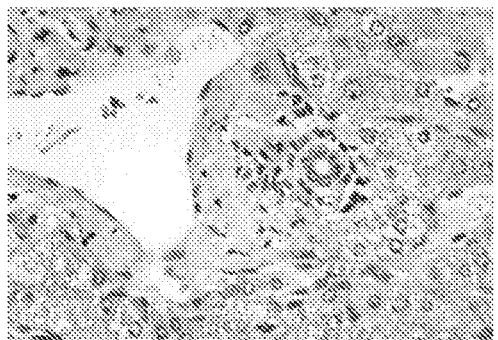
100X　　　　　　　　　400X
Normal 2
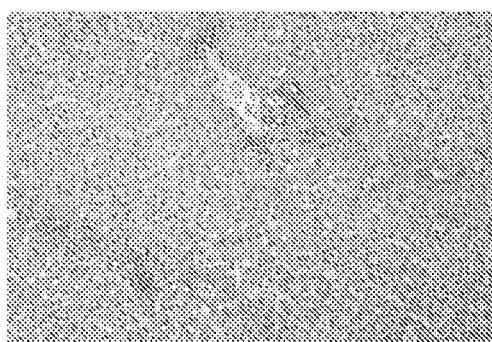 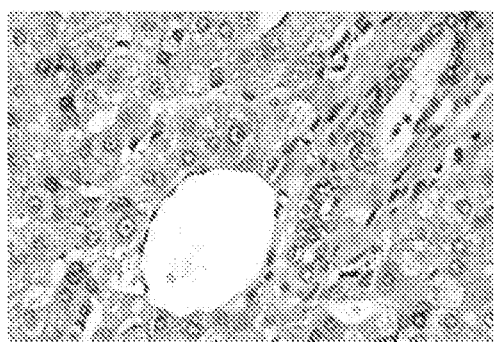
100X　　　　　　　　　400X
Normal 3
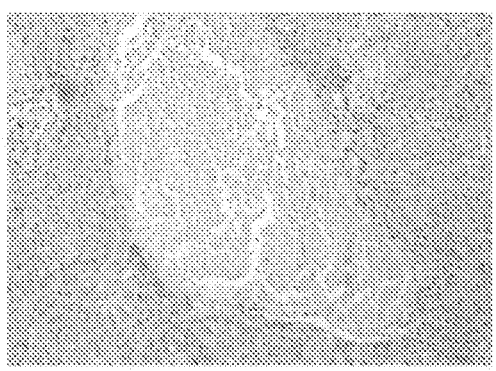 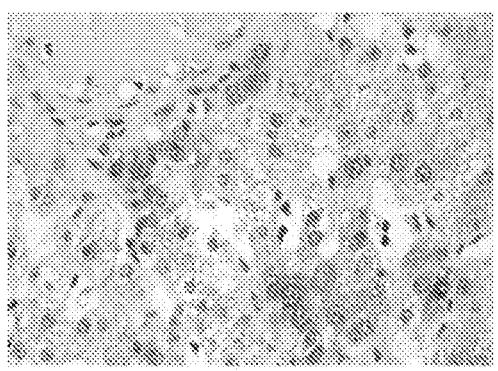
100X　　　　　　　　　400X
FIG. 2

Normal 1
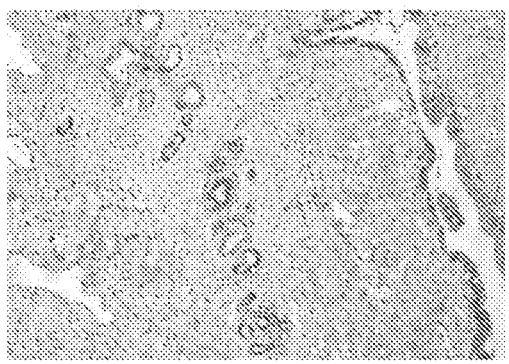
100X
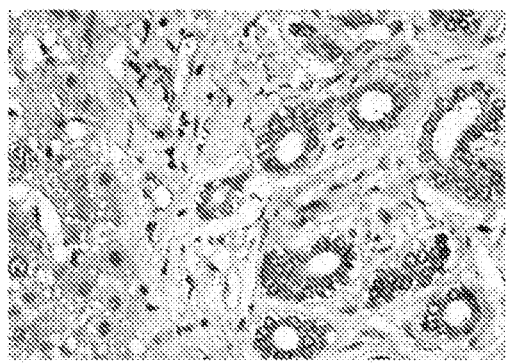
400X
Normal 2
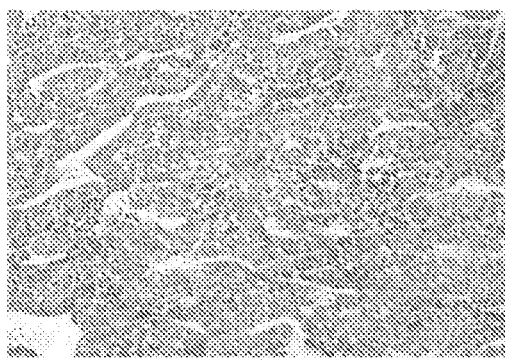
100X
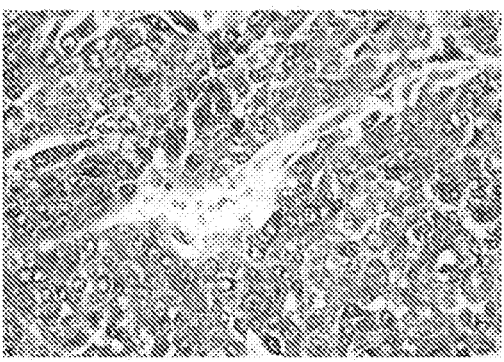
400X
Normal 3
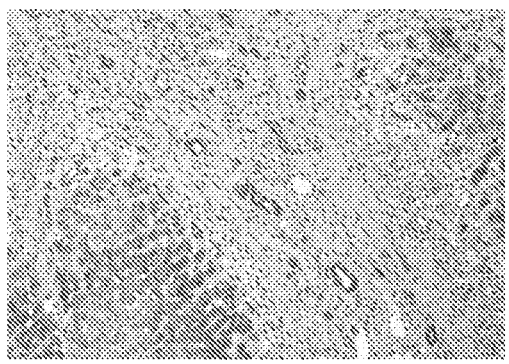
100X
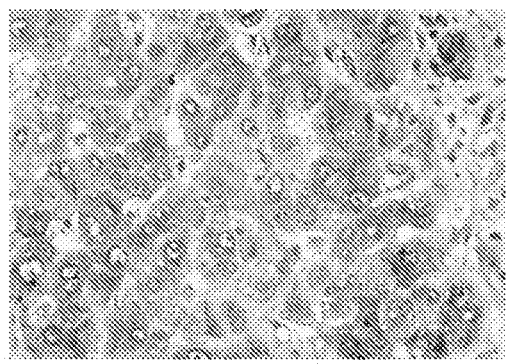
400X
FIG. 3

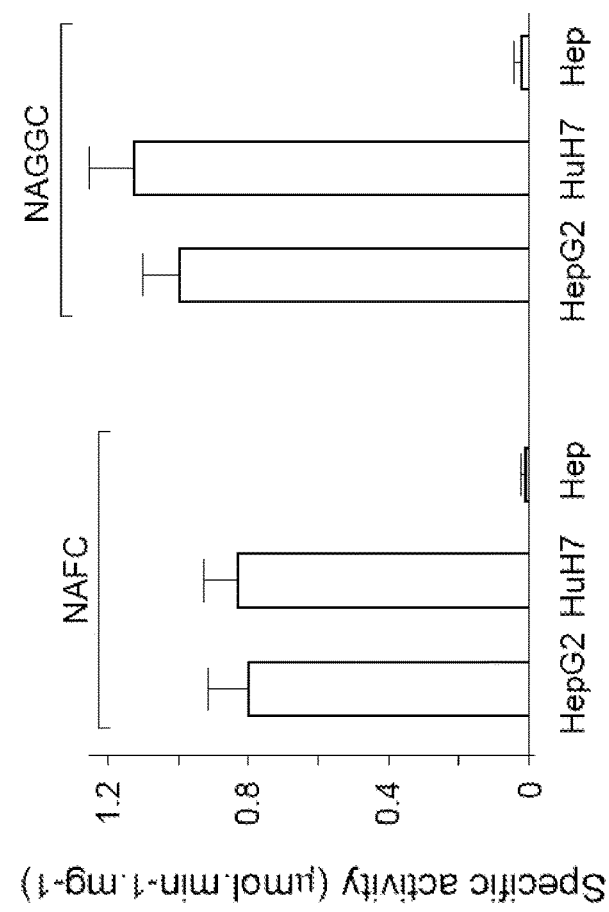
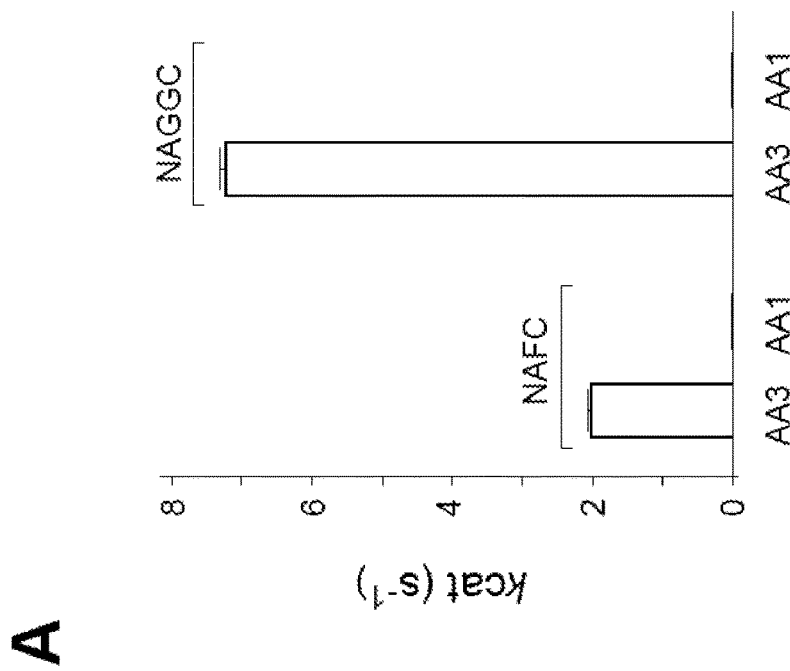
FIG. 5

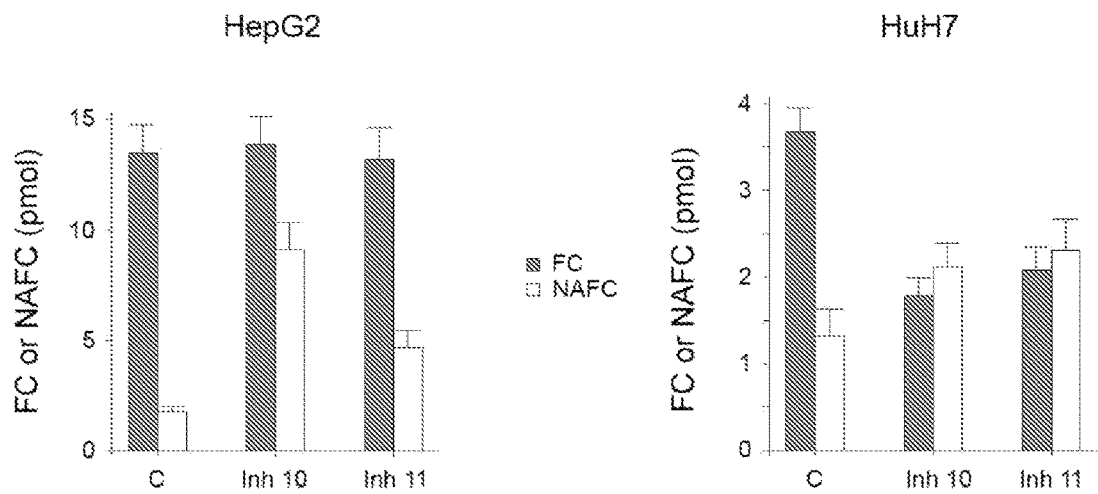
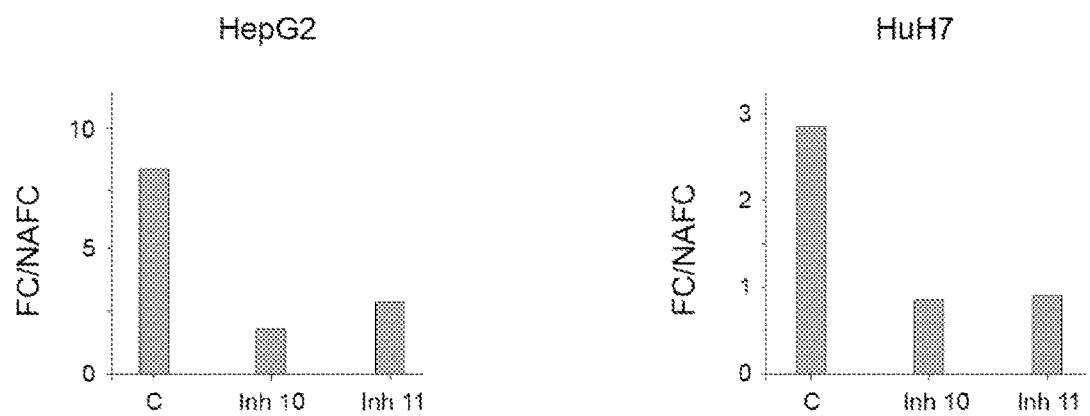
FIG. 6

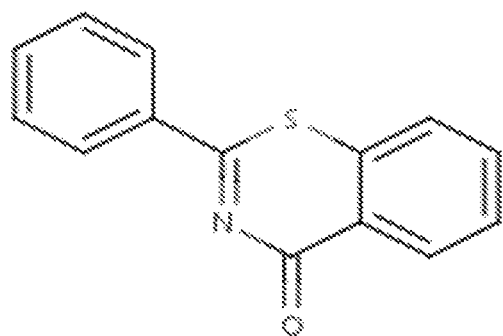
2-Phenyl-4H-1,3-benzothiazin-4-one (Inhibitor 10)
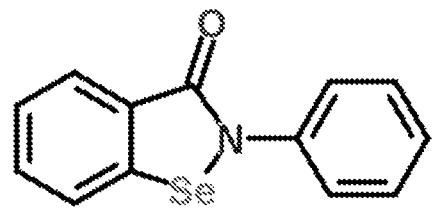
Ebselen (2-Phenyl-1,2-benzoselenazol-3(2H)-one)
FIG. 11

CHROMENONES
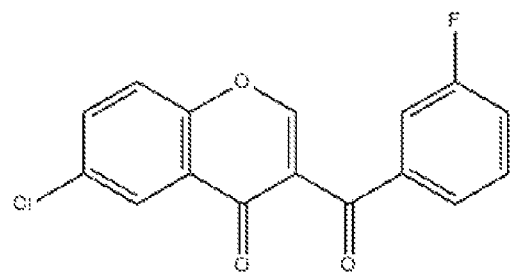
6-Chloro-3-(3-fluorobenzoyl)-4H-chromen-4-one
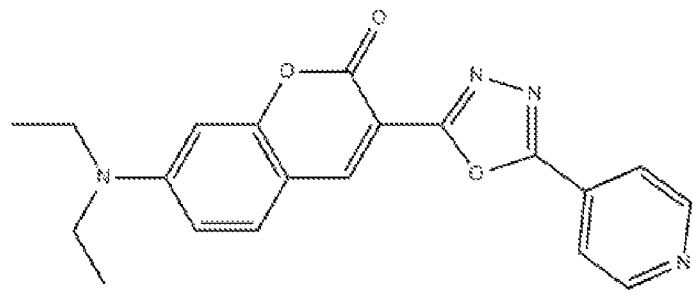
7-Diethylamino-3-(5-pyridin-4-yl-[1,3,4]oxadiazol-2-yl)-chromen-2-one
FIG. 12

THIAZOLES
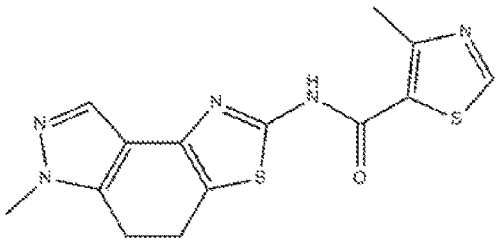
4-Methyl-N-(6-methyl-5,6-dihydro-4H-[1,3]thiazolo
[4,5-e]indazol-2-yl)-1,3-thiazole-5-carboxamide
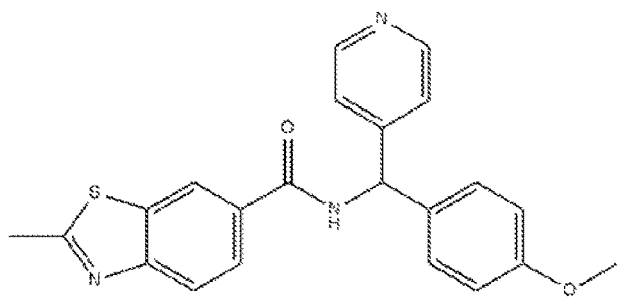
N-[(4-Methoxyphenyl)(4-pyridinyl)methyl]-2-
methyl-1,3-benzothiazole-6-carboxamide
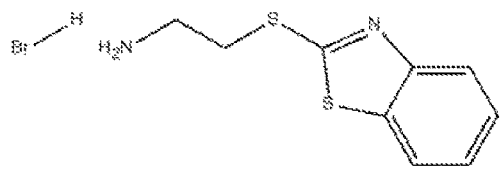
2-(1,3-Benzothiazol-2-ylsulfanyl)ethanamine hydrobromide
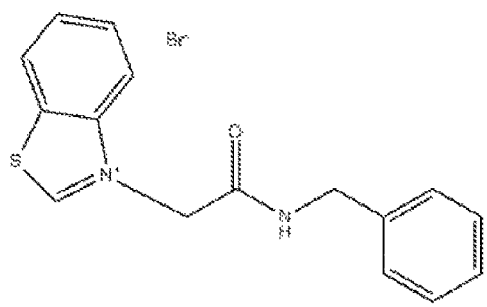
3-[2-(Benzylamino)-2-oxoethyl]-
1,3-benzothiazol-3-ium bromide
FIG. 13

THIENOPYRIMIDINES
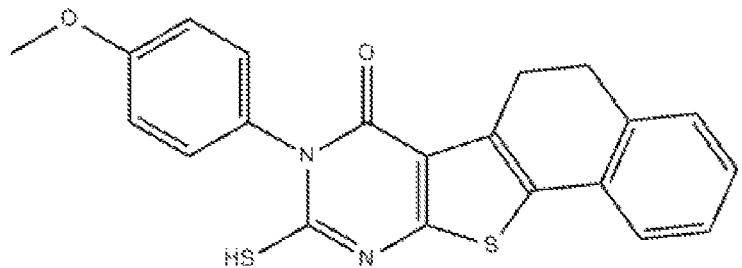
8-(4-Methoxyphenyl)-9-sulfanyl-5,8-dihydronaphtho[2',1':4,5]thieno[2,3-d]pyrimidin-7(6H)-one
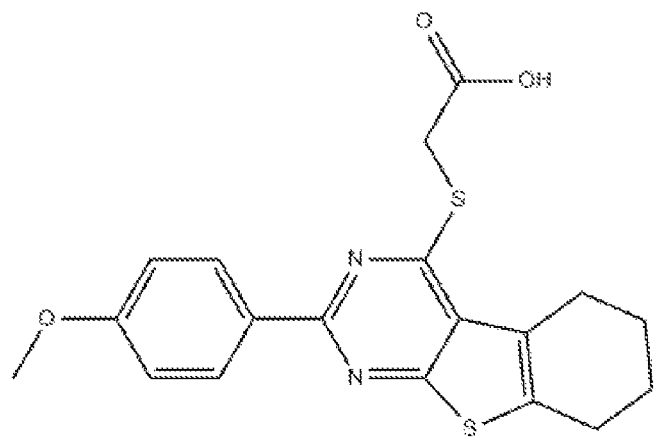
{[2-(4-Methoxyphenyl)-5,6,7,8-tetrahydro[1]benzothieno[2,3-d]pyrimidin-4-yl]sulfanyl}acetic acid
FIG. 14

(THIOCYANATOPHENYL)CARBAMOYL CYCLOHEXENES
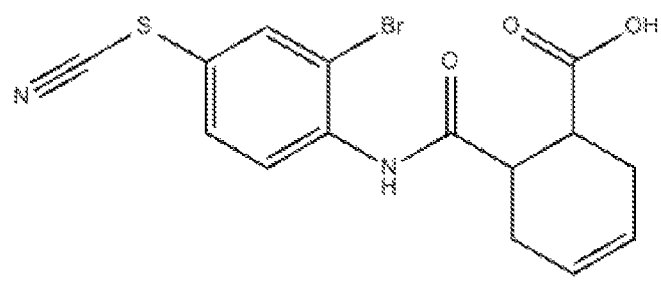
6-[(2-Bromo-4-thiocyanatophenyl)carbamoyl]-
3-cyclohexene-1-carboxylic acid
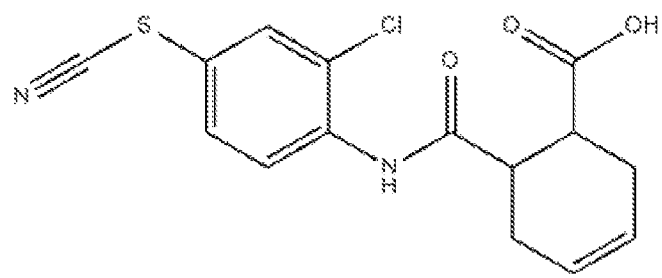
6-[(2-chloro-4-thiocyanatophenyl)carbamoyl]-
3-cyclohexene-1-carboxylic acid
FIG. 15

SULFONAMIDES (grouped together by inventor)
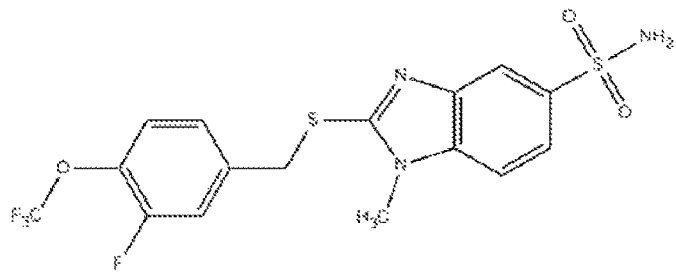
Inhibitor 11
2-[(3-Fluoro-4-methoxybenzyl)sulfanyl]-1-methyl-1H-benzimidazole-5-sulfonamide
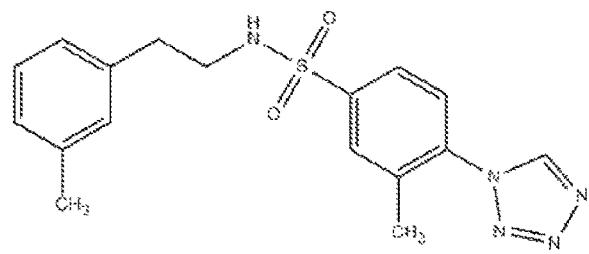
3-Methyl-4-tetrazol-1-yl-N-(2-m-tolyl-ethyl)-benzenesulfonamide
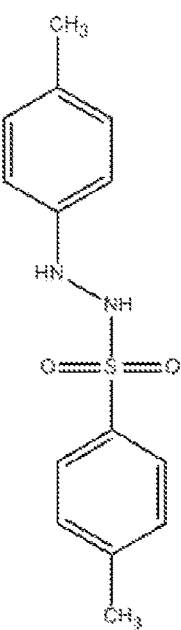
4-Methyl-N'-(4-methylphenyl)benzenesulfonohydrazide
FIG. 16

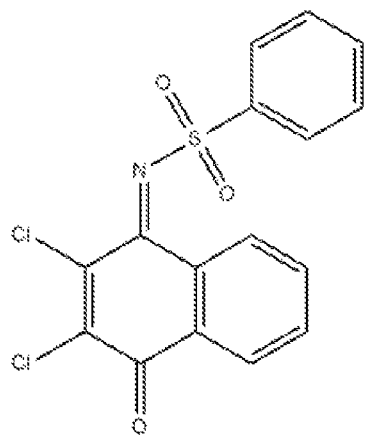
N-(2,3-Dichloro-4-oxo-4H-naphthalen-1-ylidene)-benzenesulfonamide
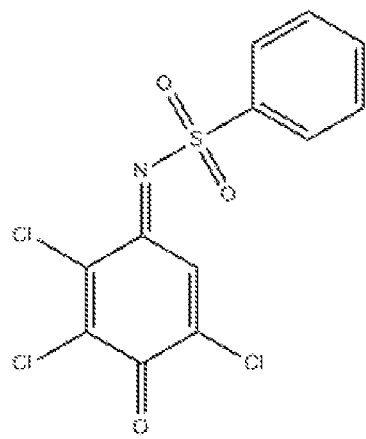
N-[(1E)-2,3,5-Trichloro-4-oxocyclohexa-2,5-dien-1-ylidene]benzenesulfonamide
FIG. 16 (continued)

THIAZOLIDINONES (grouped together by inventor)
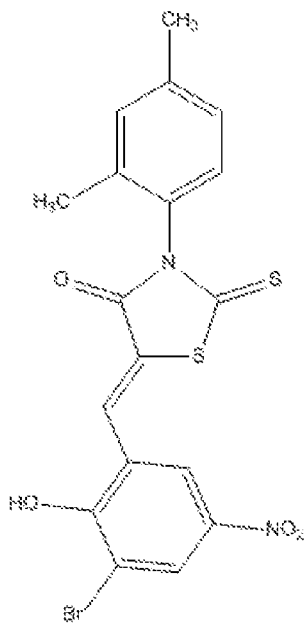
Inhibitor 3
(5Z)-5-(3-Bromo-2-hydroxy-5-nitrobenzylidene)-
3-(2,4-dimethylphenyl)-2-thioxo-1,3-thiazolidin-4-one
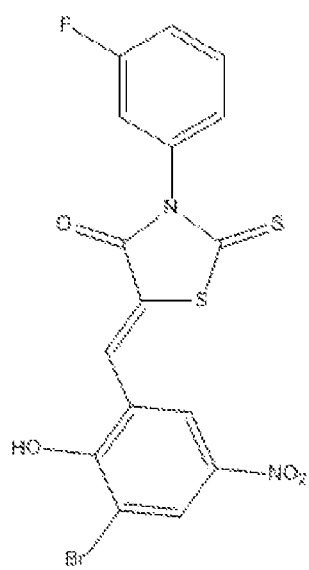
(5Z)-5-(3-Bromo-2-hydroxy-5-nitrobenzylidene)-
3-(3-fluorophenyl)-2-thioxo-1,3-thiazolidin-4-one
FIG. 17

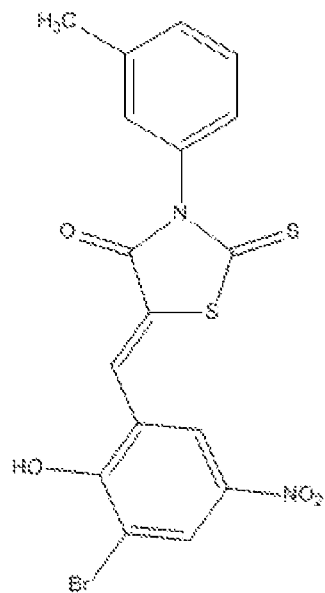
(5Z)-5-(3-Bromo-2-hydroxy-5-nitrobenzylidene)-
3-(3-methylphenyl)-2-thioxo-1,3-thiazolidin-4-one
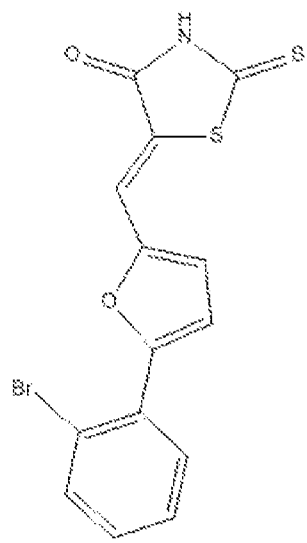
(5E)-5-{[5-(2-Bromophenyl)-2-furyl]methylene}-
2-thioxo-1,3-thiazolidin-4-one
FIG. 17 (continued)

OTHER
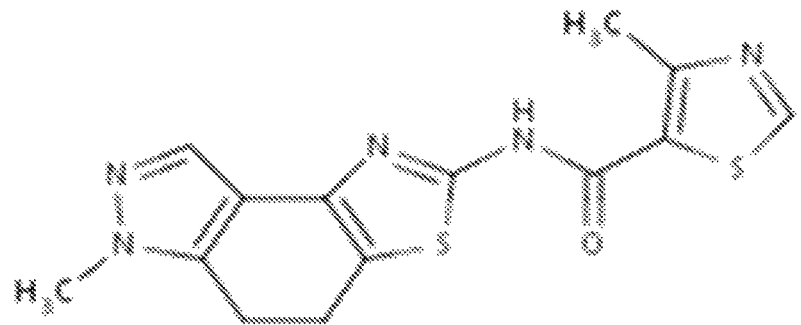
4-Methyl-N-(6-methyl-5,6-dihydro-4H-[1,3]thiazolo[4,5-e]indazol-2-yl)-1,3-thiazole-5-carboxamide
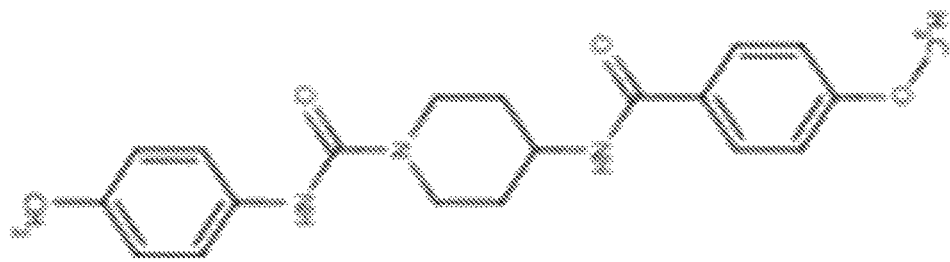
4-[(4-Methoxybenzoyl)amino]-N-(4-methylphenyl)-1-piperidinecarboxamide
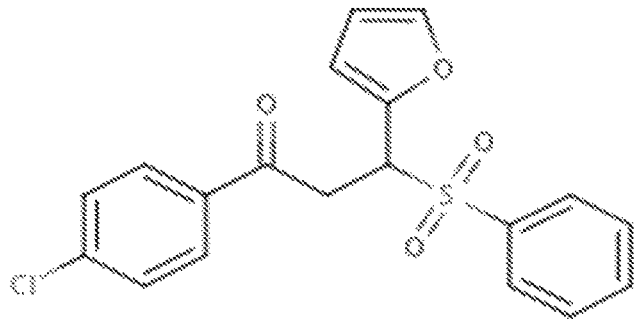
3-Benzenesulfonyl-1-(4-chloro-phenyl)-3-furan-2-yl-propan-1-one
FIG. 18

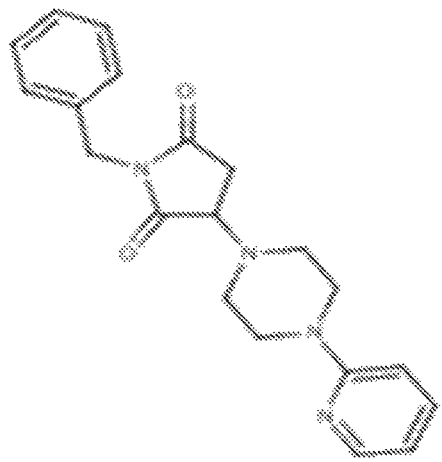
1-Benzyl-3-[4-(2-pyridinyl)-1-piperazinyl]-2,5-pyrrolidinedione
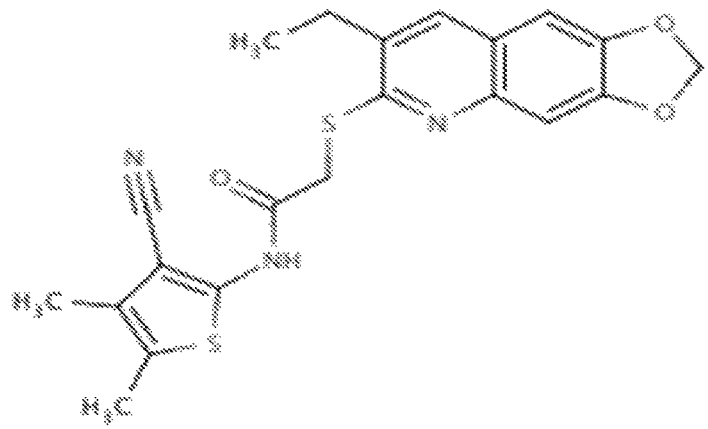
N-(3-Cyano-4,5-dimethyl-2-thienyl)-2-[(7-ethyl[1,3]dioxolo[4,5-g]quinolin-6-yl)sulfanyl]acetamide
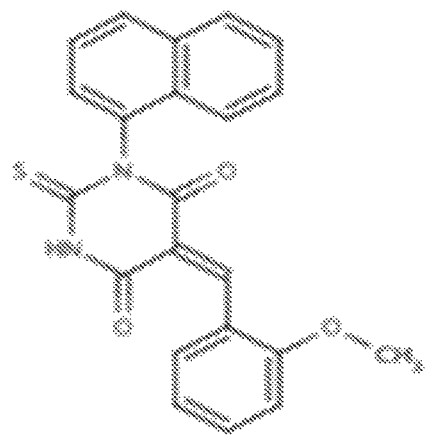
(5E)-5-(2-Methoxybenzylidene)-1-(1-naphthyl)-2-thioxodihydro-4,6(1H,5H)-pyrimidinedione
FIG. 18 (continued)

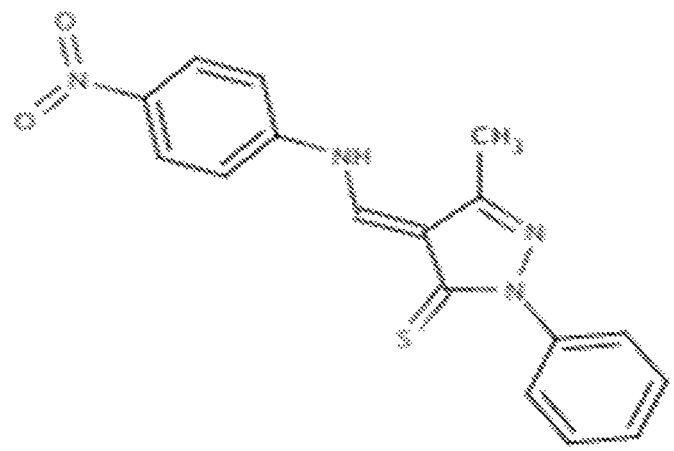
(4E)-5-Methyl-4-{[(4-nitrophenyl)amino]methylene}-2-phenyl-2,4-dihydro-3H-pyrazole-3-thione
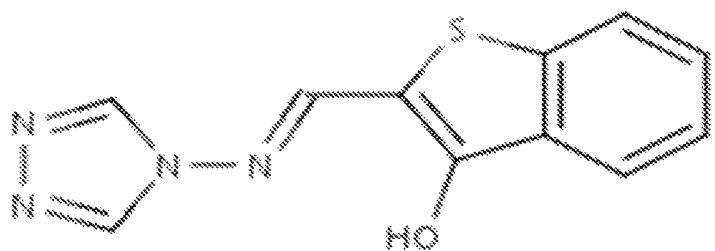
2-[(E)-(4H-1,2,4-Triazol-4-ylimino)methyl]-1-benzothiophene-3-ol
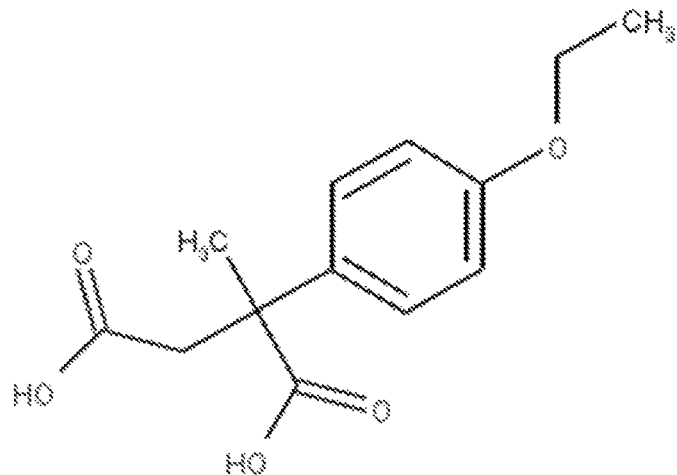
2-(4-ethoxyphenyl)-2-methyl succinic acid
FIG. 18 (continued)

N$^a$-Acetylated amino acids

N-Acetyl-L-phenylalanine

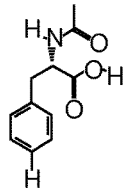

$K_m$=1.6 mM,
$V_{max}$=7.9 U

N-Acetyl-L-tyrosine

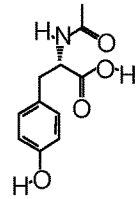

$K_m$=1.4 mM,
$V_{max}$=7.5 U

N-Acetyl-L-tryptophan

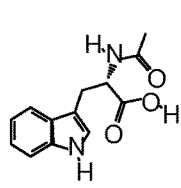

$K_m$=1.2 mM,
$V_{max}$=8.1 U

N-Acetyl-L-histidine

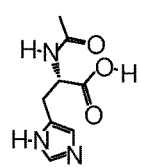

$K_m$=1.8 mM,
$V_{max}$=5.9 U

N-Acetyl-L-lysine

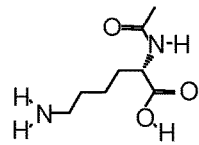

$K_m$=1.3 mM,
$V_{max}$=5.8 U

N-Acetyl-L-cysteine

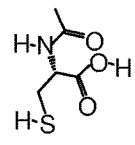

$K_m$=NA, $V_{max}$=0

N-Acetyl-L-aspartic acid

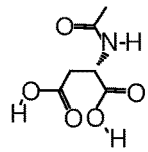

$K_m$=NA, $V_{max}$=0

N-Acetyl-L-leucine

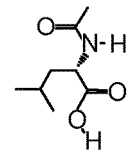

$K_m$=NA, $V_{max}$=0

Mercapturic acids

N-Acetyl-S-benzyl-L-cysteine

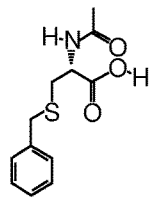

$K_m$=1.1 mM,
$V_{max}$=11.7 U

N-Acetyl-S-(2-fluorobenzyl)-L-cysteine

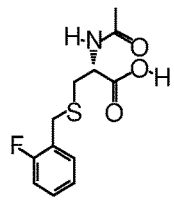

$K_m$=1.3 mM,
$V_{max}$=4.8 U

N-Acetyl-S-(2-chlorobenzyl)-L-cysteine

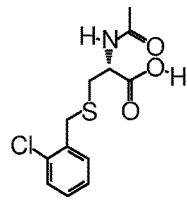

$K_m$=1.45 mM,
$V_{max}$=12.1 U

N-Acetyl-S-(3-fluorobenzyl)-L-cysteine

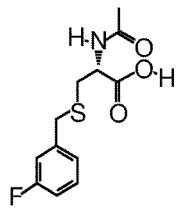

$K_m$=0.6 mM,
$V_{max}$=3.5 U

*FIG. 20*

Mercapturic acids

N-Acetyl-S-(4-chlorobenzyl)-L-cysteine

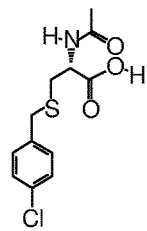

$K_m$=0.3 mM,
$V_{max}$=10.6 U

N-Acetyl-S-(4-bromobenzyl)-L-cysteine

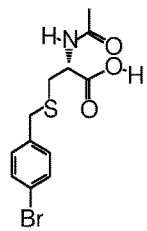

$K_m$=5.3 mM,
$V_{max}$=32.1 U

N-Acetyl-S-(metoxybenzyl)-L-cysteine

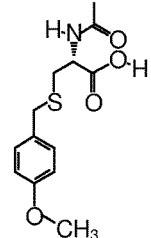

$K_m$=1.2 mM,
$V_{max}$=24.0 U

Acetyl-S-(1,1,2,2-tetrafluoroethyl)-L-cysteine

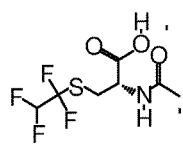

$K_m$=0.26 mM,
$V_{max}$=0.81 U

N-Acetyl-S-(2-chloro-1,1,2-trifluoroethyl)-L-cysteine

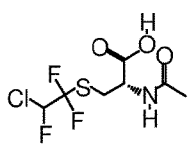

$K_m$=0.28 mM,
$V_{max}$=0.56 U

N-Acetyl-S-(2,2-difluoro-1,1-dichloroethyl)-L-cysteine

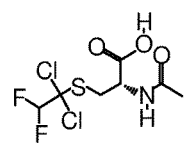

$K_m$=0.3 mM,
$V_{max}$=1.1 U

N-Acetyl-S-(2,2-dichloro-1,1-difluoroethyl)-L-cysteine

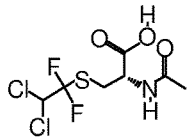

$K_m$=5.3 mM,
$V_{max}$=32.1 U

N-Acetyl-S-(1,2,2-trichlorovinyl)-L-cysteine

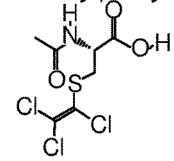

$K_m$=1.2 mM, $V_{max}$=24 U

N-Acetyl-S-(1,2-dichlorovinyl)-L-cysteine

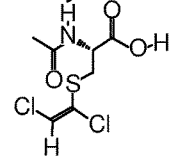

$K_m$=0.9 mM,
$V_{max}$=15.7 U

N-Acetyl-S-(2,2-dichlorovinyl)-L-cysteine

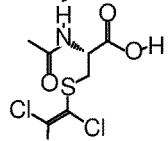

$K_m$=0.4 mM,
$V_{max}$=21.8 U

N-Acetyl-S-(1,2,3,4,4-pentachlorobutadienyl)-L-cysteine

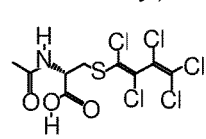

$K_m$=1.0 mM,
$V_{max}$=25.3 U

FIG. 20
*(CONT.)*

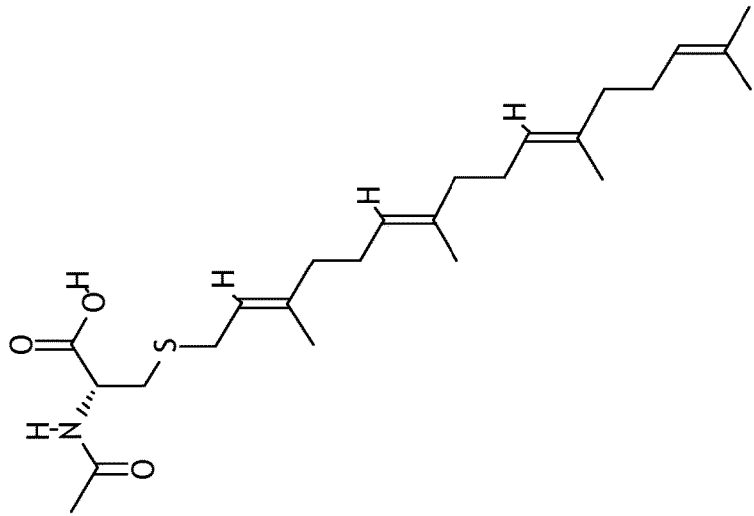
N-Acetylgeranylgeranyl-L-cysteine
$K_m = 0.14$ mM, $V_{max} = 12.1$ U
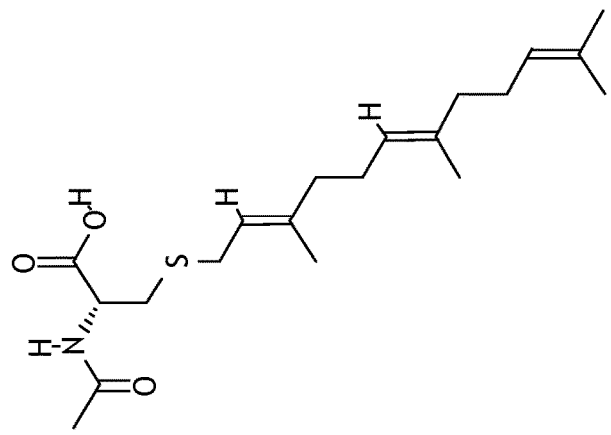
N-Acetylfarnesyl-L-cysteine
$K_m = 0.025$ mM, $V_{max} = 3.4$ U
FIG. 21

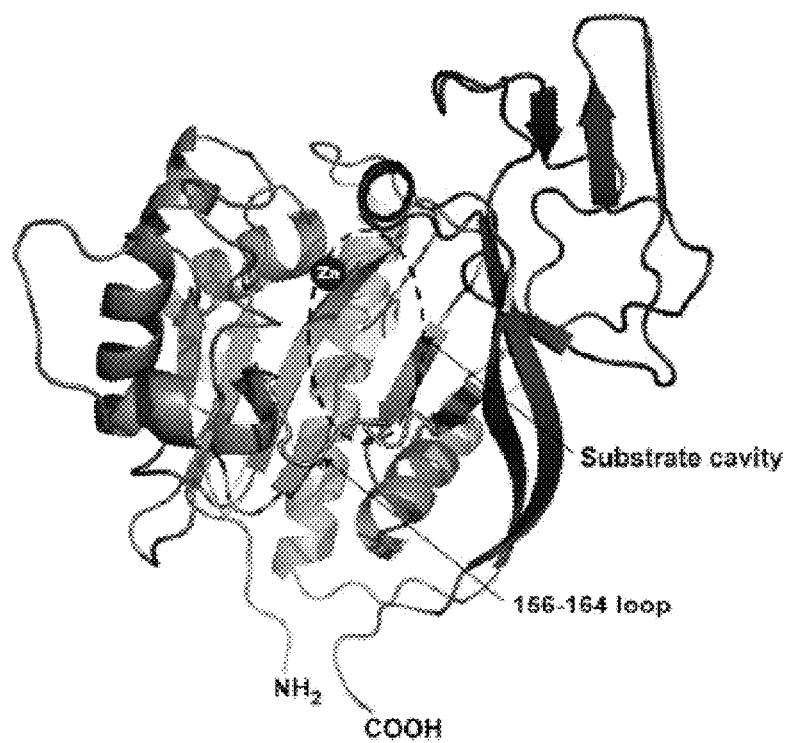
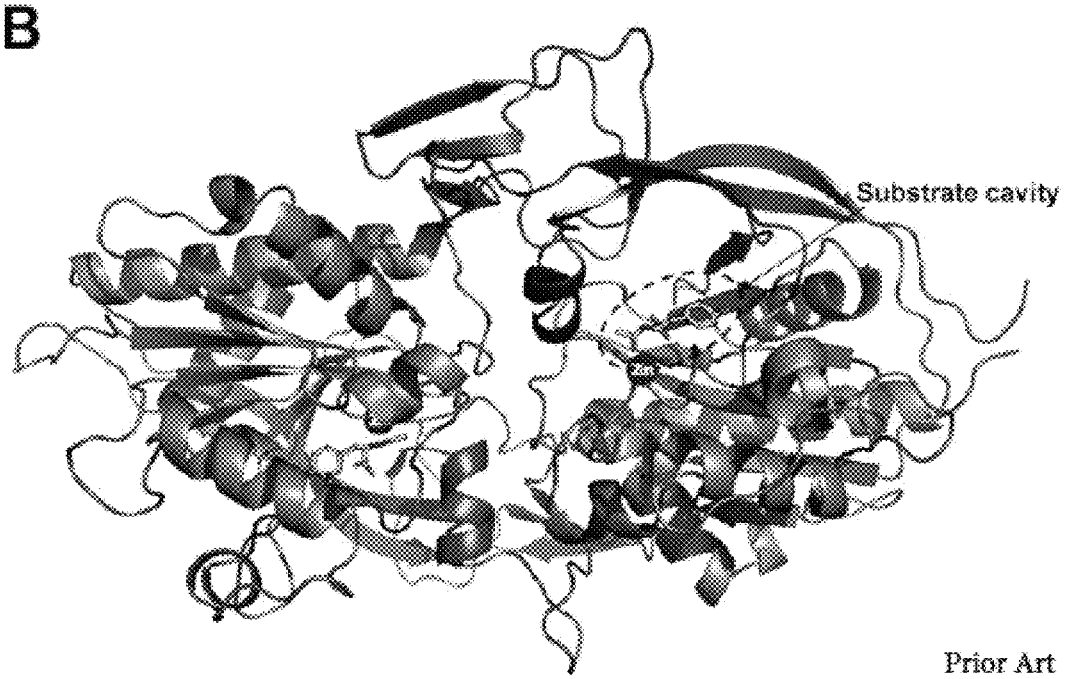
FIG. 23

INHIBITION OF AMINOCYLASE 3 (AA3) IN THE TREATMENT OF CANCER

CROSS-REFERENCE TO RELATED APPLICATIONS

This application is a national phase application under 35 U.S.C. § 371 of International Application No. PCT/US2018/051146, filed Sep. 14, 2018, which claims the benefit of priority of U.S. Provisional Patent Application No: 62/559,170 filed Sep. 15, 2017, each of which are hereby incorporated by reference in their entirety.

BACKGROUND OF THE INVENTION

1. Field of the Invention

The present disclosure relates generally to the fields of biology and medicine. Particularly, it concerns chemical compounds, methods, and compositions involving those compounds. More particularly the present invention relates to cancer, including hepatocellular carcinoma (HCC), pancreatic and colon cancer. The present invention also relates to methods and compositions of treating patients, including patients with HCC, pancreatic and colon cancers.

2. Background Art

Ras proteins are small GTPases and key regulators of diverse signal transduction pathways controlling cell growth, differentiation and apoptosis. They are also common oncogenes mutated in ~20% of all cancers [1-16]. Upregulation of Ras via its overexpression and the downregulation of physiological inhibitors of Ras have been observed in various cancers including hepatocellular carcinoma (HCC), the third leading cause of cancer-related death worldwide and the primary cause of death in patients with liver cirrhosis [17-21]. Ras proteins become active after their membrane association initiated by transfer of a prenyl, farnesyl (F) or geranylgeranyl (GG), group from F-pyrophosphate (F-PP) or GG-pyrophosphate (GG-PP) mediated by F-transferase (FTase) or GG-transferase (GGTase) respectively [9, 11, 22-24]. Carboxymethylation of the C-terminal prenylcysteine residue mediated by isoprenylcysteine carboxymethyltransferase (ICMT) completes the membrane association process of KRas whereas HRas and NRas are further palmytoylated prior to membrane association. Ras proteins bind GTP with the picomolar affinity that makes it difficult to block this process with inhibitors. Targeting Ras activity or Ras downstream effector signaling cascades in cancer therapy has been largely unsuccessful [6, 13, 14]. In addition, inhibition of the Ras prenylation enzymes (FTase or GGTase) individually was ineffective, while the simultaneous inhibition of both enzymes was toxic [6, 13, 14].

Ras proteins are important mediators of signal transduction and potent oncogenes, that have long been targets of anticancer therapy studies. Despite numerous efforts to generate approaches that block Ras activation in cancer, clinical studies using these approaches have failed. Previous efforts to directly inhibit FTase and GGTase have been clinically unsuccessful, [3-6, 12-15].

Hepatocellular carcinoma, pancreatic and colon cancer in patients represent a therapeutic challenge. There is a need for treatment approaches and regimens for these patients that otherwise have a very low life expectancy.

SUMMARY OF THE INVENTION

Here, embodiments include inter alia, methods to suppress hepatocellular carcinoma (HCC) cell growth via inhibition of Ras membrane association, a step that is critically required for their activation from inactive precursors. These methods decrease generation of the substrates of FTase and GGTase, F—PP and GG-PP, thereby impeding Ras membrane association. The current disclosure provides for therapeutic methods and compositions for treating HCC in patients through the inhibition of AA3, including, but not limited to, with a small molecule. Embodiments also include methods to suppress other cancers, including but not limited to pancreatic and colon cancer through the inhibition of AA3 such as, for example, by a small molecule.

Embodiments include methods of treating HCC, methods of reducing or inhibiting HCC growth or proliferation in a subject, methods of inhibiting growth of a HCC cell, methods for treating liver cancer, methods for preventing liver cancer, methods for treating a liver cancer patient with a small molecule AA3 inhibitor, methods for improving the prognosis of a liver cancer patient, methods for reducing risk of liver cancer, methods for reducing risk of liver cancer in a patient infected with hepatitis A, B and/or C, methods for treating a patient with liver cancer or with symptoms of liver cancer, methods for inhibiting or reducing the 90-100 kDa form of AA3, methods for inhibiting or reducing the 90-100 kDa form of AA3 but not the 35 kDa form of AA3, methods for reducing or decreasing the level of AA3 activity or function; methods for reducing or decreasing the level of AA3 expression, methods for increasing the survival rate of a patient with hepatocellular carcinoma, methods for treating metastasis or metastatic cancer, methods for inhibiting liver metastasis, methods of treating cancer resulting from metastasis of primary liver cancer, and methods of improving the symptoms of liver cancer. The steps and embodiments discussed in this disclosure are contemplated as part of any of these methods. Moreover, compositions for use in any of these methods are also contemplated. The methods, steps and embodiments discussed in this disclosure regarding HCC are also contemplated for other cancers including but not limited to pancreatic and colon cancer. Moreover, compositions for use in any of these methods referencing HCC are also contemplated for other cancers including but not limited to pancreatic and colon cancer.

Methods may comprise or consist essentially of one or more of the following steps: administering to a subject an AA3 inhibitor; administering to a subject a composition comprising an AA3 inhibitor; administering to a subject an effective amount of an AA3 inhibitor or a composition comprising an AA3 inhibitor; obtaining a biological sample from the subject; testing a biological sample from the subject for HCC; assaying the subject for AA3 inhibition; determining the subject may be responsive to therapy with an AA3 inhibitor; assaying or measuring AA3 activity or expression levels in the patient; comparing AA3 activity of expression levels to a control; treating the subject with chemotherapy, radiation, and/or immunotherapy; removing all or part of a tumor from the subject; performing a biopsy on a subject; and/or monitoring the subject for AA3 activity or expression.

In some embodiments, methods comprise administering to the subject an effective amount of a composition comprising an AA3 inhibitor. Other aspects of the disclosure relate to methods of inhibiting growth of a HCC cell comprising administering to the cell an effective amount of an inhibitor. In some embodiments, the inhibitor inhibits or reduces levels of AA3 activity or expression. In specific embodiments, AA3 activity is decreased, inhibited, lessened, or reduced. In specific embodiments, methods involve inhibiting AA3 activity in a cell. In certain embodiments, both the 90-100 kDa form of AA3 form and the 35 kDa form of AA3 is the target of the AA3 inhibitor. In other embodiments, the 90-100 kDa form of AA3 form but not the the 35 kDa form of AA3 is the target of the AA3 inhibitor. In further embodiments, at least the 90-100 kDa form of AA3 is targeted.

In some embodiments, the AA3 inhibitor inhibits or reduces levels of a 95-100 kDa form of AA3. In other embodiments, the AA3 inhibitor does not inhibit a 35 kDa form of AA3 and only inhibits the 95-100 kDa form. In some embodiments, the compositions exclude an inhibitor of a 35 kDa form of AA3. The AA3 inhibitor may be any appropriate agent that inhibits an AA3. In some embodiments, the inhibitor is an antibody or a nucleic acid or a small molecule.

In certain embodiments, AA3 activity is inhibited with a small molecule. The term "small molecule" refers to a low molecular weight (<900 daltons) organic compound that may help regulate a biological process, with a size on the order of $10^{-9}$ m.

In some embodiments, the small molecule is a benzothiazinone, or derivative, analog, or salt thereof, which may be used in a method or composition discussed herein. In specific embodiment, the small molecule is 2-Phenyl-4H-1,3-benzothiazin-4-one, which is also referred to as Inhibitor 10 below, or a derivative, analog, or salt thereof. A compound with the chemical structure of Formula I, which includes 2-Phenyl-4H-1,3-benzothiazin-4-one (Inhibitor 10), can be used as an AA3 inhibitor in embodiments. Embodiments include a derivative, analog, or salt of a compound with the chemical structure of Formula I. Embodiments also include a composition, including a pharmaceutical formulation, comprising a derivative, analog, or salt of a compound with the chemical structure of Formula I. Embodiments also include composition or pharmaceutical formulation comprising a derivative, analog, or salt of Inhibitor 10. It is also specifically contemplated that one or more compounds whose structure is covered by Formula I may be excluded.

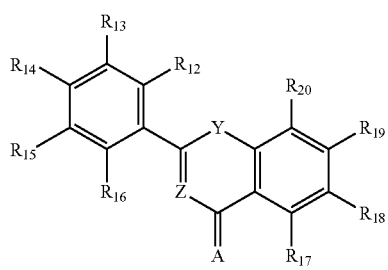

Formula I wherein X is O, S, CH$_2$, or NH; Z is N or CH; A is O, S, or NH; and each of $R_{12}$-$R_{20}$ independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester.

In some embodiments, the small molecule is a sulfonamide, or a derivative, analog, or salt thereof, which may be used in a method or composition discussed herein. In specific embodiment, the small molecule is 2-[(3-Fluoro-4-methoxybenzyl)sulfanyl]-1-methyl-1H-benzimidazole-5-sulfonamide (referred to as Inhibitor 11 below), or a derivative, analog, or salt thereof. Other sulfonamide are 3-Methyl-4-tetrazol-1-yl-N-(2-m-tolyl-ethyl)-benzenesulfonamide, N-(2,3-Dichloro-4-oxo-4H-naphthalen-1-ylidene)-benzenesulfonamide and N-[(1E)-2,3,5-Trichloro-4-oxocyclohexa-2,5-dien-1-ylidene]benzenesulfonamide, or a derivative, analog, or salt thereof. A compound with Formula II, which includes 2-[(3-Fluoro-4-methoxybenzyl)sulfanyl]-1-methyl-1H-benzimidazole-5-sulfonamide (Inhibitor 11), can be used as an AA3 inhibitor in embodiments. In some embodiments, there is a compound that is a derivative, analog, or salt of an agent that has a chemical structure of Formula II. Embodiments also include a composition, including a pharmaceutical formulation, comprising a derivative, analog, or salt of a compound with the chemical structure of Formula II. Embodiments also include composition or pharmaceutical formulation comprising a derivative, analog, or salt of Inhibitor 11. It is also specifically contemplated that one or more compounds whose structure is covered by Formula II may be excluded.

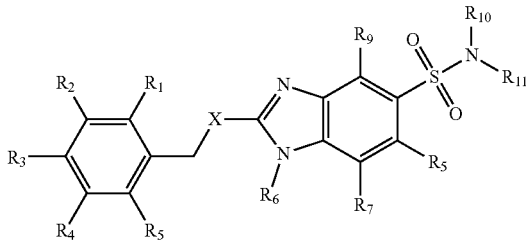

Formula II wherein X is O, S, CH$_2$, or NH; and each of $R_1$-$R_{11}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester.

In additional embodiments, the small molecule is a thiazolidinone (also referred to as a TZD), which may be used in a composition or method discussed herein. In specific embodiments, the small molecule is (5Z)-5-(3-Bromo-2-hydroxy-5-nitrobenzylidene)-3-(2,4-dimethylphenyl)-2-thioxo-1,3-thiazolidin-4-one (referred to as Inhibitor 3 herein), or a derivative, analog, or salt thereof. In other embodiments, a thiazolidinone is (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one, (5E)-5-{[5-(2-Bromophenyl)-2-furyl]methylene}-2-thioxo-1,3-thiazolidin-4-one, or a derivative, analog, or salt thereof. A compound with Formula III or a compound with the functional group shown below—or derivative, analog, or salt of either thereof—can be used as an AA3 inhibitor in embodiments. Embodiments also include a composition, including a pharmaceutical formulation, comprising a derivative, analog, or salt of a compound with the chemical structure of Formula III. It is also specifically contemplated that one or more compounds whose structure is covered by Formula III may be excluded.

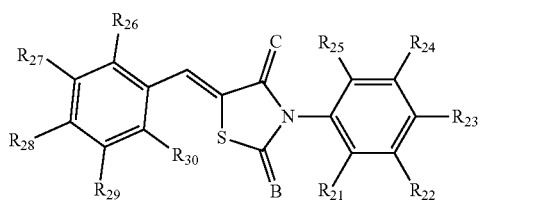

Formula III wherein B and C are each independently O, S, or NH, and each of $R_{21}$-$R_{30}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester.

Alternatively, compounds with this five-membered $C_3NS$ ring functional group may also be used as an AA3 inhibitor:

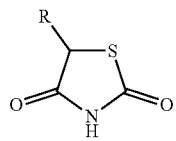

In additional embodiments, the small molecule is a chromenone, or derivative, analog, or salt thereof, which may be used in a method or composition discussed herein. In specific embodiments, the small molecule is 6-Chloro-3-(3-fluorobenzoyl)-4H-chromen-4-one, 7-Diethylamino-3-(5-pyridin-4-yl-[1,3,4]oxadiazol-2-yl)-chromen-2-one or a derivative, analog, or salt thereof. It is specifically contemplated that any of these may be excluded in an embodiment.

In additional embodiments, the small molecule is a thiazole, or a derivative, analog, or salt thereof. In specific embodiments, the small molecule is 4-Methyl-N-(6-methyl-5,6-dihydro-4H-[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide, [2-(Benzylamino)-2-oxoethyl]-1,3-benzothiazol-3-ium bromide, or derivative, analog, or salt thereof. Embodiments also include a composition, including a pharmaceutical formulation, comprising a derivative, analog, or salt of a compound with the chemical structure of a chromenone. It is specifically contemplated that any of these may be excluded in an embodiment.

In additional embodiments, the small molecule is a thienopyrimidine, or a derivative, analog, or salt thereof, which may be used in methods or compositions discussed herein. In some embodiments, the small molecule is 8-(4-Methoxyphenyl)-9-sulfanyl-5,8-dihydronaphtho[2',1':4,5]thieno[2,3-d]pyrimidin-7(6H)-one, {[2-(4-Methoxyphenyl)-5,6,7,8-tetrahydro[1]benzothieno[2,3-d]pyrimidin-4-yl]sulfanyl}acetic acid, or derivative, analog, or salt thereof. Embodiments also include a composition, including a pharmaceutical formulation, comprising a derivative, analog, or salt of a compound with the chemical structure of a thenopyrimidine. It is specifically contemplated that any of these may be excluded in an embodiment.

In additional embodiments, the small molecule is a (thiocyanatophenyl)carbamoyl cyclohexene, or a derivative, analog, or salt thereof, which may be used in methods or compositions discussed herein. In some embodiments, the small molecule is 6-[(2-Bromo-4-thiocyanatophenyl)carbamoyl]-3-cyclohexene-1-carboxylic acid, 6-[(2-Chloro-4-thiocyanatophenyl)carbamoyl]-3-cyclohexene-1-carboxylic acid, or derivative, analog, or salt thereof. Embodiments also include a composition, including a pharmaceutical formulation, comprising a derivative, analog, or salt of a compound with the chemical structure of a (thiocyanatophenyl) carbamoyl cyclohexene. It is specifically contemplated that any of these may be excluded in an embodiment.

In some embodiments, the small molecule is 4-Methyl-N-(6-methyl-5,6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3-Benzenesulfonyl-1-(4-chloro-phenyl)-3-furan-2-yl-propan-1-one, 1-Benzyl-3-[4-(2-pyridinyl)-1-piperazinyl]-2,5-pyrrolidinedione, N-(3-Cyano-4,5-dimethyl-2-thienyl)-2-[(7-ethyl[1,3]dioxolo[4,5-g]quinolin-6-yl)sulfanyl]acetamide, (5E)-5-(2-Methoxybenzylidene)-1-(1-naphthyl)-2-thioxodihydro-4,6(1H,5H)-pyrimidinedione, (4E)-5-Methyl-4-{[(4-nitrophenyl)amino]methylene}-2-phenyl-2,4-dihydro-3H-pyrazole-3-thione, 2-[(E)-(4H-1,2,4-Triazol-4-ylimino)methyl]-1-benzothiophene-3-ol, 2-(4-ethoxyphenyl)-2-methyl succinic acid, or a derivative, analog, or salt thereof. Embodiments also include a composition, including a pharmaceutical formulation, comprising a derivative, analog, or salt of a compound discussed above. It is specifically contemplated that any of these may be excluded in an embodiment.

In further embodiments, a small molecule compound with Formula IV or a compound with the functional group shown below (or a derivative, analog, or salt of either thereof) can be used as an AA3 inhibitor in embodiments. Embodiments also include a composition, including a pharmaceutical formulation, comprising a derivative, analog, or salt of a compound with the chemical structure of Formula IV. It is also specifically contemplated that one or more compounds whose structure is covered by Formula IV may be excluded.

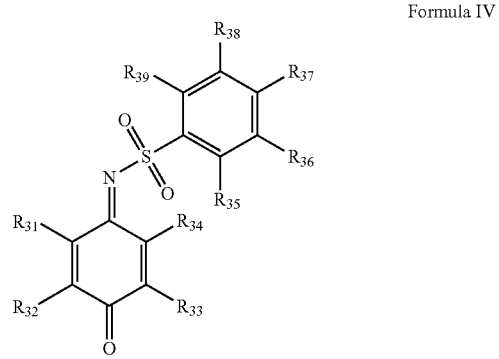

Formula IV wherein each of $R_{31}$, $R_{32}$, and $R_{35}$-$R_{39}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester; and $R_{33}$ and $R_{34}$ independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, or come together to form a carbocyclic or heterocyclic ring of 5 to 7 atoms.

In further embodiments, a small molecule compound with Formula V or a compound with the functional group shown below (or a derivative, analog, or salt of either thereof) can be used as an AA3 inhibitor in embodiments. Embodiments also include a composition, including a pharmaceutical formulation, comprising a derivative, analog, or salt of a compound with the chemical structure of Formula V. It is also specifically contemplated that one or more compounds whose structure is covered by Formula V may be excluded.

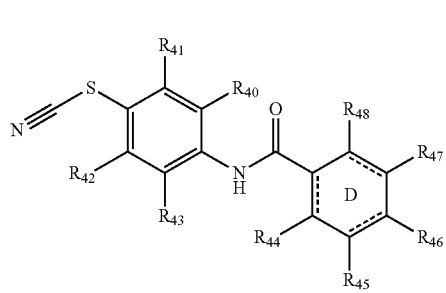

Formula V wherein each of $R_{40}$-$R_{48}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester; and the ring denoted by "D" may include one, two, or three carbon-carbon double bonds.

In further embodiments, a small molecule compound with Formula VI or a derivative, analog, or salt of either thereof can be used as an AA3 inhibitor in embodiments. Embodiments also include a composition, including a pharmaceutical formulation, comprising a derivative, analog, or salt of a compound with the chemical structure of Formula VI. It is also specifically contemplated that one or more compounds whose structure is covered by Formula VI may be excluded.

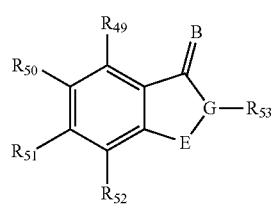

Formula VI wherein each of $R_{49}$-$R_{52}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, $R_{53}$ is a substituted or unsubstituted aromatic ring, B is O or S, G is N or CH, and E is $CH_2$, NH, S, or Se, or a derivative, analog, or salt thereof. In some embodiments, a molecule of Formula VI is 2-(4-methylphenyl)-1,2-benzothiazol-3-one (inhibitor 21) or 2-phenyl-1,2-benzoselenazol-3(2H)-one (also referred to as Ebselen). It is also specifically contemplated that one or more compounds whose structure is covered by Formula VI may be excluded.

In some embodiments, the inhibitor inhibits an AA3 polypeptide or 95-100 kDa form of AA3 or a 35 kDa form of AA3.

In some embodiments of the methods, the AA3 inhibitor binds the AA3 polypeptide. In certain embodiments, the AA3 inhibitor comprise an anti-AA3 antibody or fragment thereof. The antibodies may be monoclonal, polyclonal, Fab fragments, single chain variable fragments, humanized, and/or third generation (3G) fragments.

In other embodiments, the inhibitor inhibits AA3 nucleic acid expression. In certain embodiments, the AA3 expression inhibitor is a nucleic acid molecule. In some embodiments, the nucleic acid inhibitor is an siRNA, an miRNA, an aptamir, or a ribozyme.

In some embodiments, AA3 inhibitors are pharmaceutically formulated. The pharmaceutical formulations may be administered in any appropriate manner. In some embodiments of the methods, the formulations are administered systemically or locally. An AA3 inhibitor may be administered to a tumor bed or to the area of a resected tumor. In some embodiments, the administration is done orally, parenterally, subcutaneously, intramuscularly or intratumorally.

In some embodiments of the methods, the formulation comprising an AA3 inhibitor is administered via a targeted drug delivery system, or a liver-targeted delivery system or the drug may be conjugated to a carrier protein.

In some embodiments, the methods further comprise administration of an additional therapy. In some embodiments, the additional therapy comprises tumor ablation therapy, embolization therapy, radiation therapy, chemotherapy, liver-targeted therapy, surgery or any appropriate combination thereof. In some aspects, the liver-targeted therapy comprises any appropriate liver-targeted drug. In some aspects, the liver-targeted drug is sorafenib and/or regorafenib.

Embodiments include methods wherein the subject is a mammal. In other embodiments, the subject is a human subject. The subject will have hepatocellular carcinoma (HCC), will be suspected of having, or will be at risk of developing HCC. In certain aspects, the human subject is a patient who has been diagnosed with HCC. In some aspects, the subject has been previously treated for cancer. In some aspects, the subject is at risk of developing HCC. In other aspects the subject has hepatitis B or C or is a carrier for hepatitis B virus or hepatitis C virus. In other embodiments, the subject has been diagnosed with cirrhosis and/or exhibits signs of cirrhosis. In further embodiments, the subject has or is at risk for recurrent HCC. In other embodiments, the subject has or is at risk for metastasis.

In some embodiments, the methods further comprise obtaining a biological sample. In some aspects, the sample is from a subject. The subject could be a human. In some embodiments, the sample is a liver sample. The sample could comprise HCC tumor or cancer cells.

In some embodiments of the methods, the control is a non-cancer sample, a normal hepatocyte sample or a non-hepatocyte sample.

In some embodiments of the methods, the measuring level of expression of AA3 comprises measuring protein expression. Protein expression can be measured by performing, for example, ELISA, RIA, FACS, dot blot, Western Blot, immunohistochemistry, antibody-based radioimaging, mass spectroscopy, a combination of said methods or any other appropriate protein expression assay. In some aspects, measuring protein expression comprises measuring a 90-100 kDa form of AA3.

In further embodiments, the methods further comprise administration of a therapy to the subject to reduce HCC growth or proliferation in the subject. The therapy could be an immunotherapy. In some aspects, the immunotherapy comprises anti-AA3 antibodies. In other aspects, the anti- AA3 antibodies inhibit or reduces the levels of a 95-100 kDa form of AA3 but not a 35 kDa form of AA3.

In additional embodiments, the methods of diagnosis comprise administering an additional therapy. The additional therapy comprises tumor ablation therapy, embolization therapy, radiation therapy, chemotherapy, liver-targeted therapy, surgery or any appropriate combination thereof. In some aspects, the liver-targeted therapy comprises sorafenib and/or regorafenib.

In some embodiments, the methods further comprise measuring the levels of N-acetyl-F-cysteine (NAFC) and/or N-acetyl-GG-cysteine (NAGGC) in the sample and comparing the levels or ratio to a control.

Certain embodiments are directed to pharmaceutical compositions comprising an inhibitor(s) of AA3. Other embodiments are directed to pharmaceutical compositions comprising an inhibitor of 95-100 kDa form of AA3. In certain aspects, the inhibitor(s) does not affect a 35 kDa monomer of AA3. In the pharmaceutical compositions disclosed herein, the AA3 inhibitor may be any appropriate agent that inhibits an AA3. In some embodiments, the inhibitor is an antibody inhibitor or a nucleic acid inhibitor or a small molecule inhibitor. In some embodiments, the inhibitor a inhibits AA3 polypeptide or 95-100 kDa form of AA3 but not a 35 kDa form of AA3. In other embodiments, the inhibitor inhibits nucleic acid expression.

In certain aspects, the pharmaceutical compositions are formulated so as to be administered in any appropriate manner. In some embodiments, the formulations are administered systemically or locally. In some embodiments, the formulation is for administration that is oral, parenteral, subcutaneous, intramuscular, or intratumoral.

In some embodiments the pharmaceutical formulations are administered via a targeted drug delivery system, or a liver-targeted delivery system or the inhibitor may be conjugated to a carrier protein.

Compositions of the present invention include immunogenic compositions against AA3 protein, 95-100 kDa form of AA3, 35 kDa form of AA3, or any combination thereof, wherein the protein(s), antigen(s) or epitope(s) are contained in an amount effective to achieve the intended purpose. More specifically, an effective amount means an amount of active ingredients necessary to stimulate or elicit an immune response, or provide resistance to, amelioration of, or mitigation of disease. In more specific aspects, an effective amount prevents, alleviates or ameliorates symptoms of disease or infection, or prolongs the survival of the subject being treated. Determination of the effective amount is well within the capability of those skilled in the art, especially in light of the detailed disclosure provided herein. For any preparation used in the methods of the invention, an effective amount or dose can be estimated initially from in vitro studies, cell culture, and/or animal model assays. For example, a dose can be formulated in animal models to achieve a desired immune response or circulating antibody concentration or titer. Such information can be used to more accurately determine useful doses in humans.

It is contemplated that any method or composition described herein can be implemented with respect to any other method or composition described herein and that different embodiments may be combined.

Use of the one or more compositions may be employed based on methods described herein. Use of one or more compositions may be employed in the preparation of medicaments for treatments, immunoglobulins for treatment or detection methods according to the methods described herein. Other embodiments are discussed throughout this application. Any embodiment discussed with respect to one aspect of the disclosure applies to other aspects of the disclosure as well and vice versa. The embodiments in the Example section are understood to be embodiments that are applicable to all aspects of the technology described herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. It is to be noted, however, that the appended drawings illustrate certain embodiments of the invention and therefore are not to be considered limiting in their scope.

FIG. 1 (A) AA3 expression in normal hepatocytes and HCC cells lines. (A) AA3 relative expression levels in HCC cell lines in comparison with normal hepatocytes. Combined AA3 monomer and oligomer levels were used for calculations obtained in 3 independent experiments. (B) A representative AA3 immunoblot of normal hepatocytes and HCC cell lines. The HR-C1 antibody was used for human AA3 immunoblotting.

FIG. 2 AA3 expression in normal livers. The HR-C1 antibody was used for AA3 immunodetection.

FIG. 3 AA3 expression in liver tumors of HCC patients. The HR-C1 antibody was used for AA3 immunodetection.

FIG. 5 (A) Human AA3 and rat AA1 deacelylation activity with NAFC and NAGGC as substrates. The activity was measured in the fluorescent assay (see methods). (B) Deacetylation activity with NAFC and NAGGC as substrates of immunoaffinity purified AA3 from HuH7 and HepG2 cells, and normal primary hepatocytes (Hep).

FIG. 6. (A) FC and NAFC levels in HUH7 and HepG2 cells untreated (C=untreated control) and treated with inhibitors (Inh) 10 and 11. (B) The effect of inhibitors 10 and 11 of the [FC]/[NAFC] ratio in HepG2 and HuH7 cell lines.

FIG. 11 Chemical structures for 2-Phenyl-4H-1,3-benzothiazin-4-one (Inhibitor 10) and Ebselen (2-Phenyl-1,2-benzoselenazol-3(2H)-one).

FIG. 12 Chemical structure for 6-Chloro-3-(3-fluorobenzoyl)-4H-chromen-4-one and 7-Diethylamino-3-(5-pyridin-4-yl-[1,3,4]oxadiazol-2-yl)-chromen-2-one.

FIG. 13 Chemical structures for 4-Methyl-N-(6-methyl-5,6-dihydro-4H-[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide and 3-[2-(Benzylamino)-2-oxoethyl]-1,3-benzothiazol-3-ium bromide.

FIG. 14 Chemical structures for 8-(4-Methoxyphenyl)-9-sulfanyl-5,8-dihydronaphtho[2',1':4,5]thieno[2,3-d]pyrimidin-7(6H)-one and {[2-(4-Methoxyphenyl)-5,6,7,8-tetrahydro[1]benzothieno[2,3-d]pyrimidin-4-yl]sulfanyl}acetic acid.

FIG. 15 Chemical structure for 6-[(2-Bromo-4-thiocyanatophenyl)carbamoyl]-3-cyclohexene-1-carboxylic acid and 6-[(2-Chloro-4-thiocyanatophenyl)carbamoyl]-3-cyclohexene-1-carboxylic acid.

FIG. 16 Chemical structures for 2-[(3-Fluoro-4-methoxybenzyl)sulfanyl]-1-methyl-1H-benzimidazole-5-sulfonamide (Inhibitor 11), 3-Methyl-4-tetrazol-1-yl-N-(2-m-tolyl-ethyl)-benzenesulfonamide, N-(2,3-Dichloro-4-oxo-4H-naphthalen-1-ylidene)-benzenesulfonamide N-[(1E)-2,3,5-Trichloro-4-oxocyclohexa-2,5-dien-1-ylidene]benzenesulfonamide, and 4-Methyl-N'-(4-methylphenyl)benzenesulfonohydrazide.

FIG. 17 Chemical structures for (5Z)-5-(3-Bromo-2-hydroxy-5-nitrobenzylidene)-3-(2,4-dimethylphenyl)-2-thioxo-1,3-thiazolidin-4-one (Inhibitor 3), (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one and (5E)-5-{[5-(2-Bromophenyl)-2-furyl]methylene}-2-thioxo-1,3-thiazolidin-4-one.

FIG. 18 Chemical structures for 4-Methyl-N-(6-methyl-5,6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3-Benzenesulfonyl-1-(4-chloro-phenyl)-3-furan-2-yl-propan-1-one, 1-Benzyl-3-[4-(2-pyridinyl)-1-piperazinyl]-2,5-pyrrolidinedione, N-(3-Cyano-4,5-dimethyl-2-thienyl)-2-[(7-ethyl[1,3]dioxolo[4,5-g]quinolin-6-yl) sulfanyl]acetamide, (5E)-5-(2-Methoxybenzylidene)-1-(1-naphthyl)-2-thioxodihydro-4,6(1H,5H)-pyrimidinedione, (4E)-5-Methyl-4-{[(4-nitrophenyl)amino]methylene}-2-phenyl-2,4-dihydro-3H-pyrazole-3-thione, 2-[(E)-(4H-1,2,4-Triazol-4-ylimino)methyl]-1-benzothiophene-3-ol, and 2-(4-ethoxyphenyl)-2-methyl succinic acid.

FIG. 20. Substrate specificity of mouse mAA3. The $V_{max}$ unit (U) is equal to 1 µmol of a deacetylated product formed in 1 min per 1 mg protein.

FIG. 21. The Km and Vmax values of mAA3 with N-acetylfarnesylcysteine (NAFC) and N-acetylgeranylgeranylcysteine.

FIG. 23 Overview of mAA3 structure. (A) Single mAA3 protomer in ribbon representation with the substrate cavity and 156-164 loop indicated (yellow). (B) Two mAA3 protomers form the biologically observed dimer with NAY present. In both A and B the hydrolytic domain is colored green and the shielding domain is colored purple.

DETAILED DESCRIPTION OF ILLUSTRATIVE EMBODIMENTS

Figure 4:
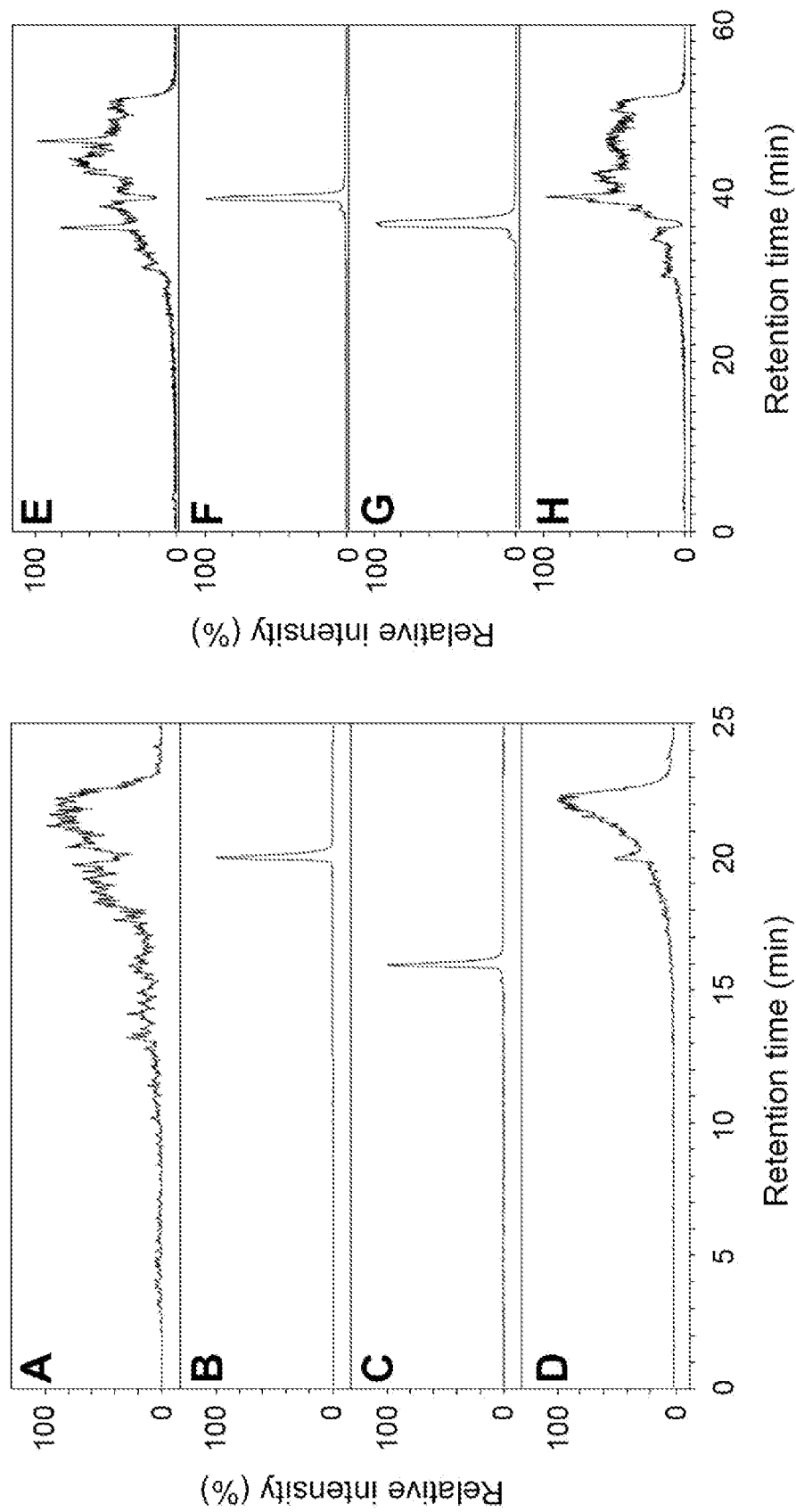
FIG. 4 Deacetylation of NAFC (a-d) and NAGCC (e-h) by human AA3. The reconstructed ion traces are the (M+H)+ ions from FC (m/z 326), NAFC (m/z 368), GGC (m/z 394) and NAGGC (m/z 436). Reconstructed ion chromatograms for m/z 326 (a,c), m/z 368 (b,d), m/z 394 (e,g) and m/z 436 (f,h). NAFC (a,b), NAFC+AA3 (c,d), NAGGC (e,f), NAGGC+AA3 (g,h).

Given the lack of success of previous efforts by the scientific community of FTase and GGTase inhibition in blocking Ras membrane association, the inventors present a different approach to inhibiting Ras membrane association. The approach is to decrease Ras prenylation mediated by FTase and GGTase by decreasing the intracellular level of F-PP and GG-PP. Both F-PP and GG-PP are known to be synthesized in the mevalonate pathway [25-27]. Suppression of this pathway via inhibition of a key enzyme, 3-hydroxy-3-methyl-glutaryl-coenzyme A reductase, demonstrated antitumor activity although paradoxical stimulation of tumor activity was also reported [28]. The latter is not surprising given that Ras prenylation is normally required for apoptosis signaling that plays a role in tumor cell survival [2-6]. A number of functionally important proteins also require prenylation for their activation [25-57]. The inventors hypothesized that in addition to the mevalonate pathway, another pathway functions that may generate F-PP and GG-PP from FC and GGC released during catabolism of the prenylated Ras and other prenylated proteins. This pathway is controlled by N-acetyltransferases that acetylate excessive amounts FC and GGC generating N-acetyl-FC (NAFC) and N-acetyl-GGC (NAGGC), which cannot be used for the F-PP and GG-PP synthesis. In addition, NAFC and NAGGC can decrease Ras membrane association via inhibition of ICMT [29]. The inventors demonstrate that an enzyme aminoacylase 3 (AA3; EC 3.5.1.114) is upregulated in HCC cell lines that deacetylates NAFC and NAGGC thereby recovering FC and GGC for F-PP and GG-PP formation in the proposed pathway.

Previous approaches to block/inhibit Ras membrane association were unsuccessful for cancer treatment in human clinical studies. A new approach is shown in the Examples and described herein to decrease Ras membrane association in hepatocellular carcinoma (HCC) cell lines via inhibition of an enzyme aminoacylase 3 (AA3; EC 3.5.1.114). AA3 expression in HCC cell lines was drastically elevated in comparison with normal hepatocytes. Treatment of HepG2 cells with AA3 inhibitors, and HepG2 and HuH7 with AA3 siRNA significantly decreased Ras membrane association and was toxic to the HCC cell lines. AA3 inhibitors also increased the levels of N-acetylfarnesylcysteine (NAFC) and N-acetylgeranylgeranylcysteine (NAGGC) in HepG2 and Huh7 cell lines. It is shown herein that AA3 deacetylates NAFC and NAGGC, and generated farnesylcysteine (FC) and geranylgeranylcysteine (GGC) are used in HCC cells for the regeneration of farnesylpyrophosphate and geranylgeranylpyrophosphate providing the prenyl (farnesyl or geranylgeranyl) group for Ras prenylation required for Ras membrane association. This was shown experimentally where purified human AA3 was capable of efficiently deacetylating NAFC and NAGGC. The current methods and compositions, therefore provide for a novel therapeutic approaches to treating HCC. The methods and compositions relate to inhibiting levels of AA3 in a subject.

According to certain aspects of the disclosure, methods of treating HCC comprise administering a composition comprising an aminocylase 3 (AA3; EC 3.5.1.114) inhibitor to a subject. In some embodiments of the methods the AA3 inhibitor inhibits or reduces levels of a 95-100 kDa form of AA3. In other embodiments, the AA3 inhibitor does not inhibit a 35 kDa form of AA3 and only inhibits the 95-100 kDa form. In some embodiments, the compositions exclude an inhibitor of a 35 kDa form of AA3. The AA3 inhibitor may be any appropriate agent that inhibits an AA3. In some embodiments, the inhibitor is an antibody inhibitor or a nucleic acid inhibitor or a small molecule inhibitor. In some embodiments, the inhibitor inhibits the 95-100 kDa form of AA3 or a 35 kDa form of AA3. In other embodiments, the inhibitor inhibits nucleic acid expression. In some embodiments of the methods, the compositions are immunotherapeutic and comprise anti-AA3 antibodies. The antibodies could be monoclonal or polyclonal or Fab fragments or single chain variable fragments or third generation (3G) fragments.

In some embodiments of the methods, the compositions comprising AA3 inhibitors are pharmaceutically formulated. The pharmaceutical formulations may be administered in any appropriate manner. In some embodiments of the methods, the formulations are administered systemically or locally. In some embodiments, the administration is orally, parenterally, subcutaneously, intramuscularly or intratumorally. In some embodiments of the methods, the formulation comprising an AA3 inhibitor is administered via a targeted drug delivery system, or a liver-targeted delivery system or the drug may be conjugated to a carrier protein. In some embodiments, the methods further comprise administration of an additional therapy. In some embodiments, the additional therapy comprises tumor ablation therapy, embolization therapy, radiation therapy, chemotherapy, liver-targeted therapy, surgery or any appropriate combination thereof. In some aspects, the liver-targeted therapy comprises any appropriate liver-targeted drug. In some aspects, the liver-targeted drug is sorafenib and/or regorafenib.

According to other aspects of the disclosure pharmaceutical compositions comprising an inhibitor(s) of AA3. Other embodiments are directed to pharmaceutical compositions comprising an inhibitor of 95-100 kDa form of AA3. In certain aspects, the inhibitor(s) does not affect a 35 kDa monomer of AA3. In the pharmaceutical compositions disclosed herein, the AA3 inhibitor may be any appropriate agent that inhibits an AA3. In some embodiments, the inhibitor is an antibody inhibitor or a nucleic acid inhibitor or a small molecule inhibitor. In some embodiments, the inhibitor inhibits AA3 polypeptide or 95-100 kDa form of AA3 but not a 35 kDa form of AA3. In other embodiments, the inhibitor inhibits nucleic acid expression. In certain aspects, the pharmaceutical compositions are formulated so as to be administered in any appropriate manner. In some embodiments, the formulations are administered systemically or locally. In some embodiments, the administration is orally, parenterally, subcutaneously, intramuscularly or intratumorally. In some embodiments the pharmaceutical formulations are administered via a targeted drug delivery system, or a liver-targeted delivery system or the inhibitor may be conjugated to a carrier protein.

Further aspects of the disclosure relate to methods of reducing or inhibiting HCC growth or proliferation in a subject comprising administering to the subject an effective amount of a composition comprising an AA3 inhibitor.

Other aspects of the disclosure relate to methods of inhibiting growth of a HCC cell comprising administering to the cell an effective amount of an inhibitor of a 90-100 kDa form of AA3 form. In some embodiments of these methods, the inhibitor inhibits or reduces levels of 90-100 kDa form of AA3 form but not 35 kDa form of AA3.

The texts of the references cited in this disclosure are herein incorporated by reference in their entireties. The meaning of terms as intended is defined herein below.

I. Definitions

A "subject," "individual" or "patient" is used interchangeably herein and refers to a vertebrate, for example a primate, a mammal or a human. Mammals include, but are not limited to cattle, equines, canines, bovines, ovines, murines, rats, simians, humans, farm animals, sport animals and pets. Also intended to be included as a subject are any subjects involved in clinical research trials not showing any clinical sign of disease, or subjects involved in epidemiological studies, or subjects used as controls.

The term "providing" is used according to its ordinary meaning to indicate "to supply or furnish for use." In some embodiments, the protein is provided directly by administering the protein, while in other embodiments, the protein is effectively provided by administering a nucleic acid that encodes the protein. In certain aspects the invention contemplates compositions comprising various combinations of nucleic acid, antigens, peptides, and/or epitopes.

The term "substantially the same" or "not significantly different" refers to a level of expression that is not significantly different than what it is compared to. Alternatively, or in conjunction, the term substantially the same refers to a level of expression that is less than 2, 1.5, or 1.25 fold different than the expression or activity level it is compared to.

The term "similarity" refers to a peptide that has a sequence that has a certain percentage of amino acids that are either identical with the reference peptide or constitute conservative substitutions with the reference peptides.

Moieties of the invention, such peptides, or antigens, may be conjugated or linked covalently or noncovalently to other moieties such as adjuvants, proteins, peptides, supports, fluorescence moieties, or labels. The term "conjugate" or "immunoconjugate" is broadly used to define the operative association of one moiety with another agent and is not intended to refer solely to any type of operative association, and is particularly not limited to chemical "conjugation." Recombinant fusion proteins are particularly contemplated. Compositions of the invention may further comprise an adjuvant or a pharmaceutically acceptable excipient. An adjuvant may be covalently or non-covalently coupled to a peptide of the invention. In certain aspects, the adjuvant is chemically conjugated to the peptide.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately." The term "about" or "around" is also used to indicate that a value includes the standard deviation of error for the device or method being employed to determine the value.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" can refer to peptide that is substantially free of cellular material, bacterial material, viral material, or culture medium (when produced by recombinant DNA techniques) of their source of origin, or chemical precursors or other chemicals (when chemically synthesized). Moreover, an isolated compound refers to one that can be administered to a subject as an isolated compound; in other words, the compound may not simply be considered "isolated" if it is adhered to a column or embedded in an agarose gel. Moreover, an "isolated peptide" is a nucleic acid or protein fragment that is not naturally occurring as a fragment and/or is not typically in the functional state.

The terms "protein", "polypeptide" and "peptide" are used interchangeably herein when referring to a gene product or functional protein.

The term "amino acid" includes naturally-occurring .alpha.-amino acids and their stereoisomers, as well as unnatural (non-naturally occurring) amino acids and their stereoisomers. "Stereoisomers" of amino acids refers to mirror image isomers of the amino acids, such as L-amino acids or D-amino acids. For example, a stereoisomer of a naturally-occurring amino acid refers to the mirror image isomer of the naturally-occurring amino acid, i.e., the D-amino acid. The term "amino acid modification" or "amino acid alteration" refers to a substitution, a deletion, or an insertion of one or more amino acids.

The term "nucleic acid," "nucleotide" or "polynucleotide" refers to deoxyribonucleic acids (DNA) or ribonucleic acids (RNA) and polymers thereof in either single-, double- or multi-stranded form. The term includes, but is not limited to, single-, double- or multi-stranded DNA or RNA, genomic DNA, cDNA, DNA-RNA hybrids, or a polymer comprising purine and/or pyrimidine bases or other natural, chemically modified, biochemically modified, non-natural, synthetic or derivatized nucleotide bases. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), orthologues, and complementary sequences as well as the sequence explicitly indicated. Specifically, degenerate codon substitutions may be achieved by generating sequences in which the third position of one or more selected (or all) codons is substituted with mixed-base and/or deoxyinosine residues. The term nucleic acid is used interchangeably with gene, cDNA, and mRNA encoded by a gene.

The term "nucleotide sequence encoding a peptide" means the segment of DNA involved in producing a peptide chain, it includes regions preceding and following the coding region (leader and trailer) involved in the transcription/translation of the gene product and the regulation of the transcription/translation, as well as intervening sequences (introns) between individual coding segments (exons).

"Percentage of sequence identity" is determined by comparing two optimally aligned sequences over a comparison window, wherein the portion of the sequence (e.g., a peptide of the invention) in the comparison window may comprise additions or deletions (i.e., gaps) as compared to the reference sequence which does not comprise additions or deletions, for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

The term "percent identity" or "percent sequence identity," in the context of describing two or more polynucleotide or amino acid sequences, refer to two or more sequences or subsequences that are the same or have a specified percentage of amino acid residues or nucleotides that are the same (for example, a variant of a peptide of interest (e.g., mimotope of interest) used in the method of this invention has at least 80% sequence identity, preferably 85%, 90%, 91%, 92%, 93, 94%, 95%, 96%, 97%, 98%, 99%, or 100% identity, to a reference sequence, e.g., a corresponding epitope or mimotope of interest), when compared and aligned for maximum correspondence over a comparison window, or designated region as measured using one of the following sequence comparison algorithms or by manual alignment and visual inspection. Such sequences are then said to be "substantially identical." With regard to polynucleotide sequences, this definition also refers to the complement of a test sequence. Preferably, the identity exists over a region that is at least about 8 amino acids in length, or more preferably over a region that is at least 8-25 or at least 8 to 12 amino acids in length.

The terms "ameliorating," "inhibiting," or "reducing," or any variation of these terms, when used in the claims and/or the specification includes any measurable decrease or complete inhibition to achieve a desired result.

The term "inhibitor" refers to a therapeutic agent that indirectly or directly inhibits the activity or expression of a protein, process (e.g. metabolic process), or biochemical pathway The term "pharmaceutical formulation" is intended to mean a composition or a mixture of compositions comprising at least one active ingredient; including but not limited to, salts, solvates, and hydrates of compounds described herein.

As used herein, "treating," "treatment" or "therapy" is an approach for obtaining beneficial or desired clinical results. This includes the reduction or the alleviation of symptoms, the reduction or alleviation of pain, or the reduction in the frequency of withdrawal symptoms, and/or reduction in the occurrence of anxiety or depression and/or reduction in suicidal thinking. Furthermore, these terms are intended to encompass curing as well as ameliorating at least one symptom of the condition or disease. For example, in the case of opioid use disorders, a response to treatment includes the cessation in the use of opioids, or the cessation of at least one opioid withdrawal symptom.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

The use of the word "a" or "an" when used in conjunction with the term "comprising" in the claims and/or the specification may mean "one," but it is also consistent with the meaning of "one or more," "at least one," and "one or more than one."

II. Hepatocellular Carcinoma (HCC)

Hepatocellular carcinoma (HCC) is a common neoplasia that currently constitutes the second leading cause of cancer related death. It appears most frequently in a liver with chronic injury and cirrhosis and it is usually diagnosed as an advanced stage with a poor median survival rate of six to twenty months.

Most cases occur in developing countries, but its incidence is rising in Western countries due to hepatitis C. Notwithstanding the advances in hepatitis therapies and the fact that HCC screening has increased in several areas, still 40% present with advanced disease which is only amenable for palliative systemic treatment. The disease continues to pose a challenge to the medical and scientific community form many reasons. First: the inherent chemoresistance of the HCC neoplasia; second, the pharmacologic challenges due to a compromised liver, and last, the difficulty in assessing radiological responses accurately, etc.

A. Stages of HCC

HCC is an aggressive tumor whose treatment possibilities will depend on the phase of the tumor, the liver functionality and patient's performance status. There are several staging systems available but no consensus on which to use. The Child-Pugh system will assess the patient's hepatic reserve and liver function. Other staging systems, such as Barcelona Clinic Liver Cancer, will consider tumor phase, performance status, hepatic status, symptoms, etc. This system may provide the link between disease and treatment strategies. In very early/early stages, curative treatment (liver surgery or hepatic transplantation) and locoregional treatments (such as radiofrequency ablation), have better survival benefits.

Intermediate stage is very heterogeneous and transarterial chemoembolization/radioembolization are the main options if preserved hepatic function (Child-Pugh A) and performance status 0. Advanced cases have got a short prognosis. For these patients, systemic palliative therapies might be considered.

B. Aminoacylase 3 (AA3)

Aminoacylase 3 (AA3) is a hydrolase that removes the acyl group from N-acylated aromatic amino acids and mercapturic acids (S-conjugates of N-acetylcysteine (Pushkin et al., 2004). Pushkin et al. (2004) cloned mouse Acy3 cDNA, which encodes a deduced 318-amino acid protein (AA3) with a calculated molecular mass of about 35.2 kD. Acy3 mAA3 (mAA3) has no membrane domain, but it contains consensus sites for N-glycosylation, and also tyrosine sulfation, tyrosine and threonine phosphorylation, and myristoylation. Northern blot analysis detected high expression of an approximately 1.4-kb Acy3 transcript in kidney, followed by liver. Weaker expression was detected in heart, small intestine, brain, lung, testis, and stomach. Testis expressed an additional transcript of about 2.2 kb. Immunocytochemical analysis of mouse kidney revealed AA3 localization to the apical membrane of S1 convoluted proximal tubule cells and in the cytoplasm of S2 and S3 proximal straight tubule cells.

Figure 19:
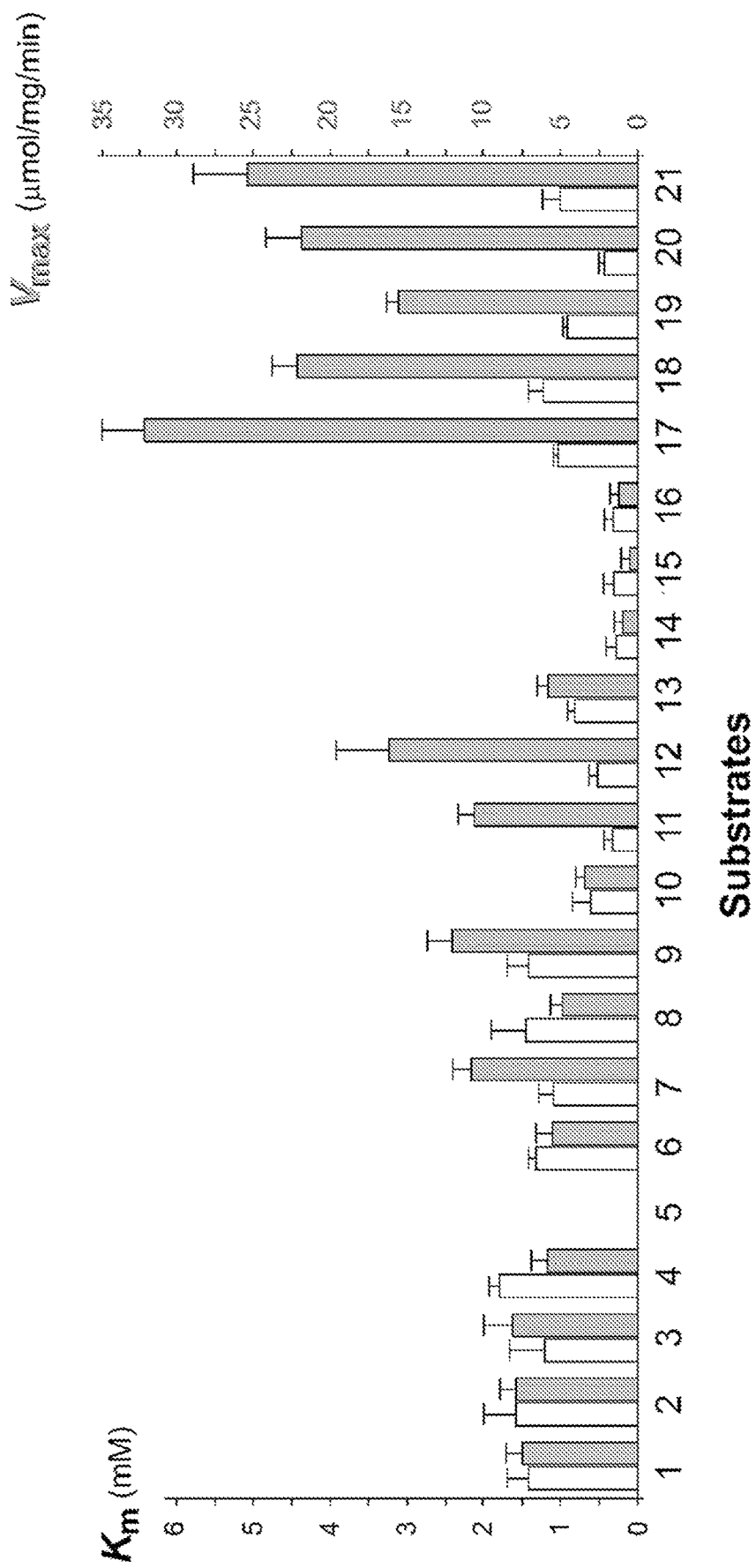
FIG. 19 The $V_{max}$ (black) and $K_m$ (green) values of mAA3 with amino (1-6) and mercapturic (6-21) acids (Newman et al., 2007). The data are means±S.E of at least three experiments except for N-acetyl-S-(4-bromobenzyl)-L-cysteine. (1) N-Acetyl-L-tyrosine (NAY), (2) N-Acetyl-L-phenylalanine, (3) N-Acetyl-L-tryptophan, (4) N-Acetyl-L-histidine, (5) N-Acetyl-L-cysteine, (6) N-Acetyl-L-lysine, (7) N-Acetyl-S-benzyl-L-cysteine, (8) N-acetyl-S-(2-fluorobenzyl)-L-cysteine, (9) N-acetyl-S-(2-chlorobenzyl)-L-cysteine, (10) N-acetyl-S-(3-fluorobenzyl)-L-cysteine, (11) N-acetyl-S-(4-chlorobenzyl)-L-cysteine, (12) N-Acetyl-S-(4-bromobenzyl)-L-cysteine, (13) N-acetyl-S-(4-methoxybenzyl)-L-cysteine, (14) N-Acetyl-S-(1,1,2,2-tetrafluoroethyl)-L-cysteine, (15) N-Acetyl-S-(2-chloro-1,1,2-trifluoroethyl)-L-cysteine, (16) N-Acetyl-S-(2,2-difluoro-1,1-dichloroethyl)-L-cysteine, (17) N-Acetyl-S-(2,2-dichloro-1,1-difluoroethyl)-L-cysteine, (18) N-Acetyl-S-(1,2,2-trichlorovinyl)-L-cysteine, (19) N-Acetyl-S-(1,2-dichlorovinyl)-L-cysteine (NADCVC), (20) N-Acetyl-S-(2,2-dichlorovinyl)-L-cysteine, (21) N-Acetyl-S-(1,2,3,4,4-pentachlorobutadienyl)-L-cysteine.

By assaying mouse AA3 (mAA3) expressed in HEK293 cells, Pushkin et al. (2004) found that it used all acetylated substrates examined, which included N-acetyl-L-histidine, N-acetyl-L-tyrosine (NAY), N-acetyl-L-phenylalanine, and S-benzyl-N-acetyl-L-cysteine. It showed highest affinity for a mercapturic acid S-benzyl-N-acetyl-L-cysteine and had a pH optimum of 7.5 to 7.7. In subsequent studies performed by these UCLA researchers (Newman et al. 2007. Ryazantev et al. 2007. Tsirulnikov et al. 2009) the substrate specificity and other catalytic properties of mAA3 were characterized in more detail. FIGS. 19 and 20 illustrating some of their results showing the substrate groups likely involved in the binding to AA3. All substrates (amino acids and mercapturic acids) have a common N-acetyl-α-amino carboxylic acid group (marked with brown circle in FIG. 20, N-acetyl-L-phenylalanine) that is likely involved in their binding to AA3. mAA3 deacetylates N-acetyl-L-tyrosine (NAY), N-acetyl-L-phenylalanine, N-acetyl-L-tryptophan, N-acetyl-L-histidine and $N^{\alpha}$-acetyl-L-lysine but not any other amino acids (N-acetyl-L-cysteine, N-acetyl-aspartic acid etc.) which indicates that the aromatic group linked to the N-acetyl-α-amino carboxylic acid group is also required for the proper substrate orientation on the active site and catalytic activity of AA3. Modifications of the phenyl group affect both the $K_m$ and $V_{max}$ values. For example, substitution of proton in phenylalanine making NAY increased the affinity but decreased $V_{max}$. N-acetylated dicarboxylic amino acids (aspartic and glutamic) and aliphatic amino acids (e.g. alanine, valine, leucine), and N-acetylated aliphatic amino acids with the SH-(cysteine) and OH-groups (serine, threonine) were not deacetylated. These results suggested that the presence of a bulky group is necessary for N-acetylated amino acids to be become substrates of AA3. AA3 also deacetylates S-conjugates of N-acetyl-L-cysteine (mercapturic acids) with bulky aromatic and haloid-containing aliphatic compounds. For example, fluorine, chlorine and bromine derivatives of N-acetyl-S-benzyl-L-cysteine have different affinity and $V_{max}$ to mAA3. In addition, the same haloid when placed at different positions of the benzyl ring has different effect on the $K_m$ and $V_{max}$ values of mAA3 (FIGS. 19, 20). AA3 also deacetylates S-conjugates of cysteine with haloid substituted vinyl and ethyl groups. Again, the position and nature of a haloid group significantly affects the $K_m$ and $V_{max}$ values of mAA3. For example, N-Acetyl-S-(2,2-difluoro-1,1-dichloroethyl)-L-cysteine has ~18 times higher affinity ($K_m$) and ~30 times lower Vmax than N-acetyl-S-(2,2-dichloro-1,1-difluoroethyl)-L-cysteine although the only difference in these compounds is that two chlorine and two fluorine atoms positions are flipped in the ethyl group between C1 and C2 atoms in the vinyl group. mAA3 also deacetylates N-acetylfarnesylcysteine (NAFC) and N-acetylgeranylgeranylcysteine (NAGGC), the precursors of farnesylpyrophosphate and geranylgeranylpyrophosphates (see [0072]) that possess long 15- and 20-carbon chain groups linked to the sulfur atom in cysteine (FIG. 21). It is interesting that NAGGC has the highest affinity (Km=0.025 mM) of all mAA3 substrates although the Km value is inversely correlates with the Vmax value. Given that mAA3 has a very high sequence homology with human AA3 (hAA3), the results obtained with mAA3 can be used to approximate the affinity of various compounds to human AA3. Mouse, rat and human AA3 use a bivalent metal ion for their catalysis (Tsirulnikov et al., 2009; Hsieh et al., 2010). $Zn^{2+}$ is found in the crystal structure of mAA3 (Hsieh at al., 2010). Chelating agents inactivate AA3 (Tsirulnikov et al., 2009) that also may be used in generating AA3 inhibitors.

Figure 22:
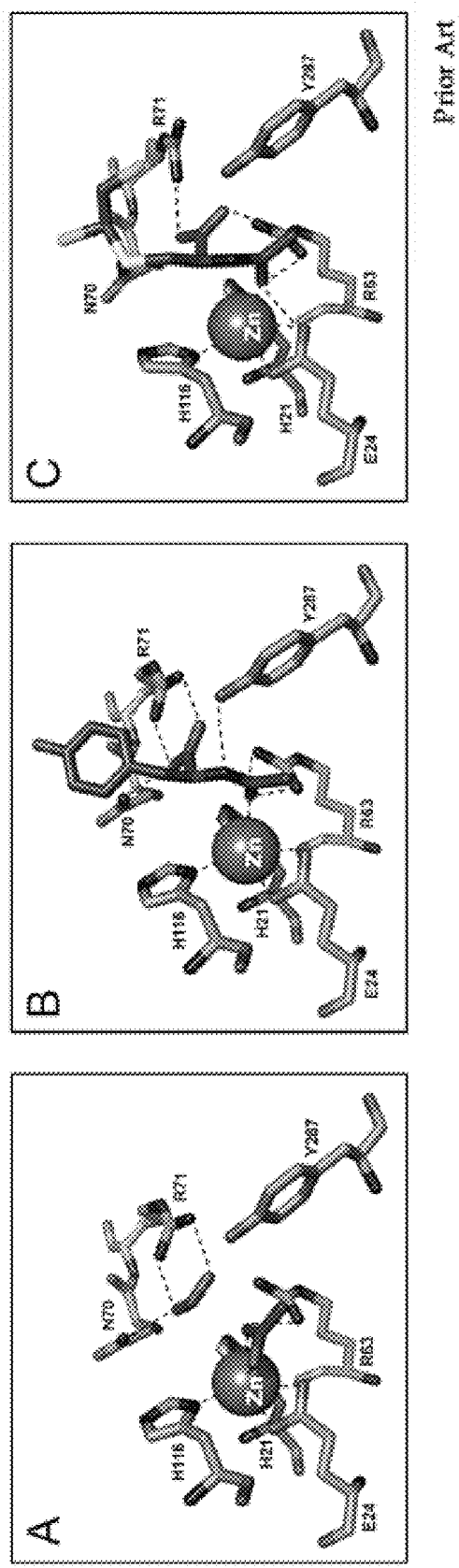
FIG. 22. Mouse mAA3 active site (Hsieh et al., 2010). (A) Wild-type mAA3 (wt-mAA3), with acetate and formate bound. (B) mAA3 E177A mutant with NAY bound in the active site. (C) mAA3 E177A mutant with N-acetyl-S-(1,2-dichlorovinyl)-L-cysteine (NADCVC) bound in the active site. The residues involved in substrate binding are represented in green sticks, the zinc ion is a grey sphere, the molecules bound in the active site are purple and the hydrogen bonding is represented by dashed black lines.

Mouse wild-type and mutant (E177A) AA3 crystal structures without and with substrates were resolved to 2-2.8 Å resolution in our study (Hsieh et al., 2010) that provided very important information on the AA3 active site architecture (FIG. 22) and helps in predicting the structure of efficient AA3 inhibitors. Crystals of wt-AA3 contained formate and acetate that were present in the crystallization solution. Formate formed the hydrogen bonds with Asn70 and Arg71, and acetate had the hydrogen bonds with Arg63 and $Zn^{2+}$ (FIG. 22A). There was no wt-AA3 crystals formed with any of the AA3 substrates. The mutation of Glu177 to alanine completely blocked catalytic activity and the E177A mutant was crystallized in the presence of NAY. The N-acetyl-α-amino carboxylic acid moiety of NAY—a conserved component of AA3 substrates (FIGS. 19, 20)—is tightly bound by seven hydrogen bonds (FIG. 22B). Specifically, the acetyl oxygen coordinates zinc and forms two hydrogen bonds with Arg63; the α-carboxylic group forms a salt bridge with Arg71 and a hydrogen bond with Asn70; and the amide has hydrogen bonds to the hydroxyl of Tyr287. It also has numerous van der Waals interactions with AA3. The side-chain of NAY binds to AA3 primarily through van der Waals interactions and via single hydrogen bond with Glu129. Eight residues participate in van der Waals interactions with the substrate side chain (Asn70, Arg71, Ile127, Glu129, Tyr156, Phe164, Ser165, Cys175). Given that five residues (Asn70, Arg71, His116, Ile127, and Phe281) involved in NAY binding are conserved in mammalian AA3 and aminoacylase 2 (AA2, EC 3.5.1.15, strictly deacetylates N-acetyl-L-aspartic acid) these common residues are likely not responsible for specificity of NAY Substrate binding to AA3. The 156-164 loop (FIG. 23) is likely plays an important role in the substrate recognition of AA3 with Phe164 that rotates approximately 50° around the β-carbon to interact with NAY playing the key role in this process. There are differences in the binding of mercapturic acid NADCVC to mouse AA3 (FIG. 22C). Specifically, the substrate's acetyl oxygen interacts with $Zn^{2+}$ and the side chains of Glu24 and Arg63. The α-carboxylic group accepts hydrogen bonds from the side chains of Arg71 and Tyr287, but unlike the NAY-mAA3, there is no hydrogen bond with Asn70. The side chain of NADCVC similar to NAY interacts with AA3 solely via van der Waals interactions except of Phe164 that does not undergo the 50° rotation. The results obtained by the inventors suggest that AA3 has a more dynamic active site that AA2, capable of accommodating a broad range of substrates.

Hartz (2011) mapped the ACY3 gene to chromosome 11q13.2 based on an alignment of the ACY3 sequence (GenBank AF3595506) with the genomic sequence (GRCh37).

III. AA3 Inhibitors

The methods of the disclosure also include the administration of compositions comprising an AA3 inhibitor. The inhibitors can be anti-AA3 antibodies, nucleic acid inhibitors, small molecules or any other agent that is known to inhibit AA3.

Cancer Cell Line Toxicity Data

Figure 24:
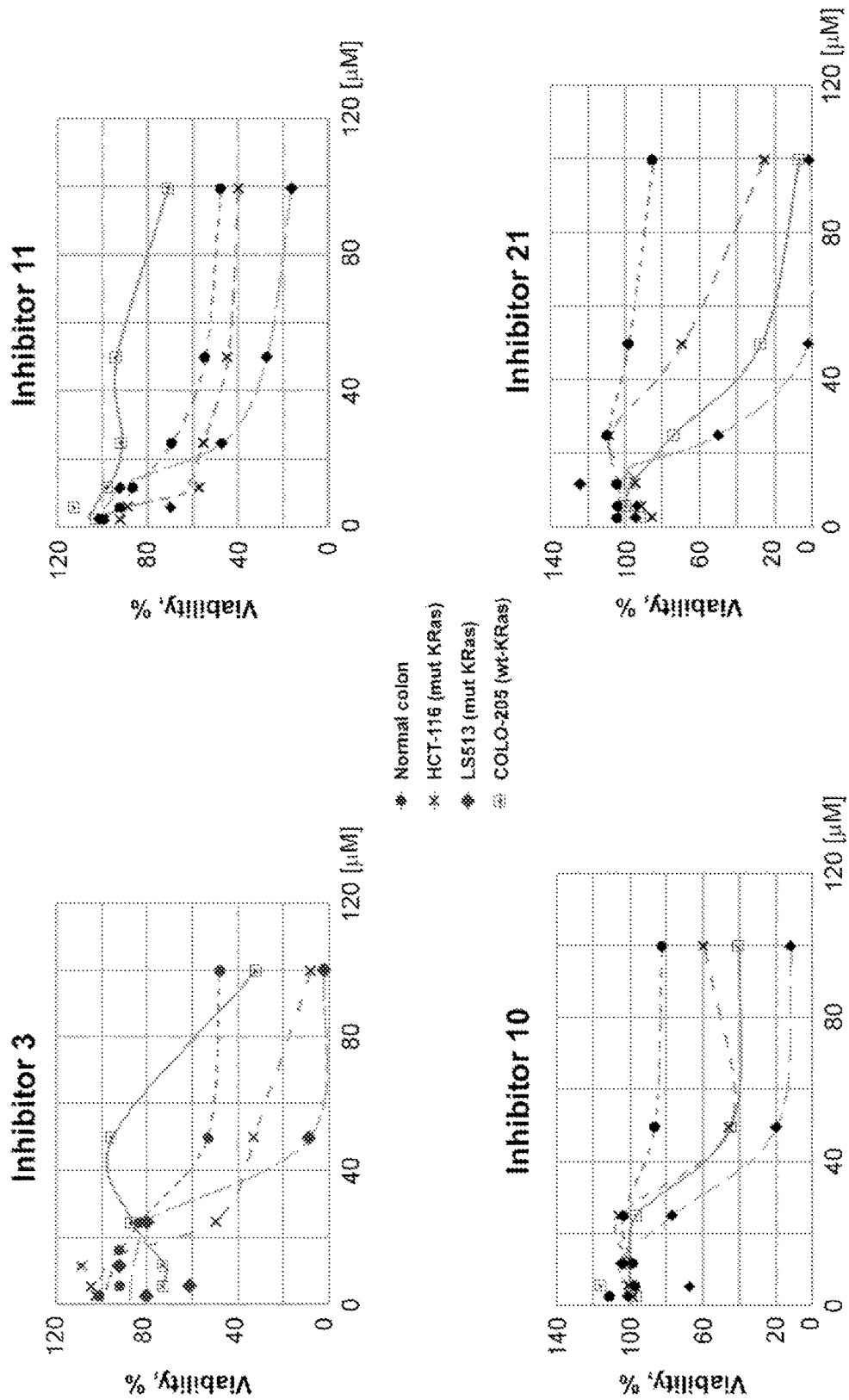
FIG. 24. Effect of AA3 inhibitors on viability of colon normal and cancer cells. AA3 inhibitors 10 and 21 suppress growth of the cell lines expressing wild type (wt) or mutant (mut) KRas. Inhibitors 3 and 11 suppress growth of the cell lines expressing mutant (mut) KRas.
Figure 25:
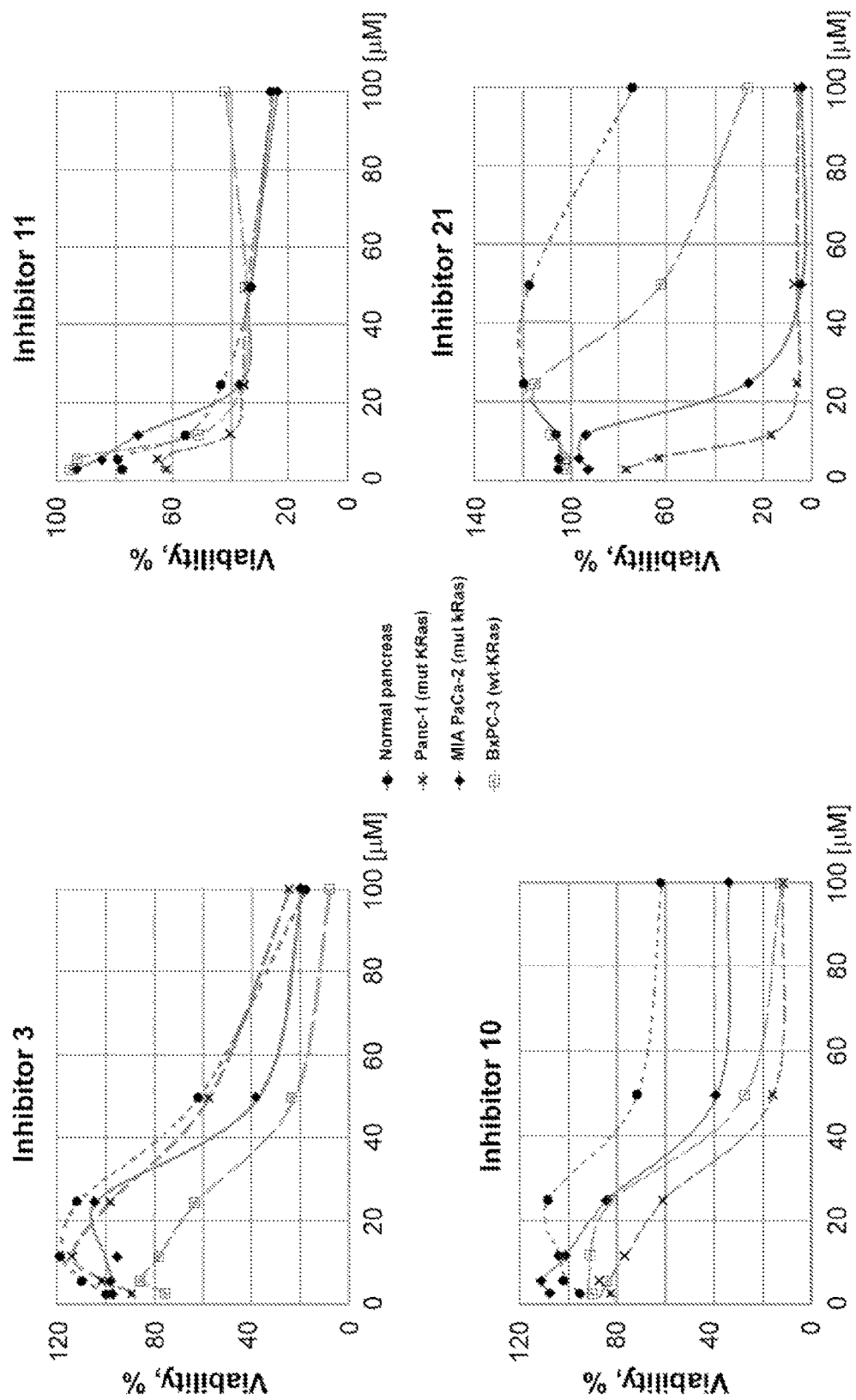
FIG. 25. AA3 inhibitors are toxic for pancreatic normal and cancer cells. Inhibitors 10 and 21 are significantly less toxic for normal than cancer cell lines. Both inhibitors are efficient for the cell lines expressing either wild type (wt) or mutant (mut) KRas.

Data using colon and pancreatic cancer cell lines support the inventors' hypothesis that AA3 inhibitors have an effect on the viability of colon normal cells and cancer cells. FIG. 24 illustrates suppression of colon cancer cell growth by AA3 inhibitors. Inhibitors 10 and 21 are significantly less toxic for normal than cancer cell lines. AA3 inhibitors also suppress pancreatic cancer cell growth (FIG. 25). Importantly AA3 inhibitors were toxic for both the cell lines expressing wt-Ras and mutant Ras. Differences in toxicity of AA3 inhibitors to different cancer lines are also likely related to the inhibitor's different uptake and metabolism by these cells.

A. Inhibitory Small Molecules

The methods of the disclosure also include the administration of compositions comprising an AA3 inhibitor that is a small molecule such the compounds listed in Example 3 below: 2-phenyl-4H-1,3-benzothiazin-4-one (Inhibitor 10) (Specs, Hopkinton, R.I.), 2-[(3-fluoro-4-methoxybenzyl) sulfanyl]-1-methyl-1H-benzimidazole-5-sulfonamide (Inhibitor 11) (Enamine, Monmouth Jct., N.J.), (5Z)-5-(3-Bromo-2-hydroxy-5-nitrobenzylidene)-3-(2,4-dimethylphenyl)-2-thioxo-1,3-thiazolidin-4-one (Inhibitor 3), or Ebselen. Another AA3 inhibitor is 2-(4-Methylphenyl)-1,2-benzothiazol-3-one (inhibitor 21). Other small molecules disclosed herein may be used in compositions and/or methods including pharmaceutical compositions.

B. Inhibitory Antibodies

In certain embodiments, an antibody or a fragment thereof that binds to at least a portion of an AA3 protein, or a 95-100 kDa form of AA3 and inhibits the protein's activity and/or function is used in the methods and compositions described herein.

In some embodiments, the antibody is a monoclonal antibody or a polyclonal antibody. In some embodiments, the antibody is a chimeric antibody, an affinity matured antibody, a humanized antibody, or a human antibody. In some embodiments, the antibody is an antibody fragment. In some embodiments, the antibody is a Fab, Fab', Fab'-SH, F(ab')2, or scFv. In one embodiment, the antibody is a chimeric antibody, for example, an antibody comprising antigen binding sequences from a non-human donor grafted to a heterologous non-human, human or humanized sequence (e.g., framework and/or constant domain sequences). In one embodiment, the non-human donor is a mouse. In one embodiment, an antigen binding sequence is synthetic, e.g., obtained by mutagenesis (e.g., phage display screening, etc.). In one embodiment, a chimeric antibody has murine V regions and human C region. In one embodiment, the murine light chain V region is fused to a human kappa light chain or a human IgG1 C region.

Examples of antibody fragments include, without limitation: (i) the Fab fragment, consisting of VL, VH, CL and CH1 domains; (ii) the "Fd" fragment consisting of the VH- and CH1 domains; (iii) the "Fv" fragment consisting of the VL and VII domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker which allows the two domains to associate to form a binding domain; (viii) bi-specific single chain Fv dimers (see U.S. Pat. No. 5,091,513) and (ix) diabodies, multivalent or multispecific fragments constructed by gene fusion (U.S. Patent Pub. 2005/0214860). Fv, scFv or diabody molecules may be stabilized by the incorporation of disulphide bridges linking the VH and VL domains. Minibodies comprising a scFv joined to a CH3 domain may also be made (Hu et al, 1996).

A monoclonal antibody is a single species of antibody wherein every antibody molecule recognizes the same epitope because all antibody producing cells are derived from a single B-lymphocyte cell line. Hybridoma technology involves the fusion of a single B lymphocyte from a mouse previously immunized with an antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced. However, in therapeutic applications a goal of hybridoma technology is to reduce the immune reaction in humans that may result from administration of monoclonal antibodies generated by the non-human (e.g., mouse) hybridoma cell line.

Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent and human amino acid sequences. In "humanized" monoclonal antibodies, only the hypervariable CDR is derived from mouse monoclonal antibodies, and the framework regions are derived from human amino acid sequences. It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

It is possible to create engineered antibodies, using monoclonal and other antibodies and recombinant DNA technology to produce other antibodies or chimeric molecules which retain the antigen or epitope specificity of the original antibody, i.e., the molecule has a binding domain. Such techniques may involve introducing DNA encoding the immunoglobulin variable region or the CDRs of an antibody to the genetic material for the framework regions, constant regions, or constant regions plus framework regions, of a different antibody. See, for instance, U.S. Pat. Nos. 5,091,513, and 6,881,557, which are incorporated herein by this reference.

By known means as described herein, polyclonal or monoclonal antibodies, binding fragments and binding domains and CDRs (including engineered forms of any of the foregoing), may be created that are specific to a protein described herein, one or more of its respective epitopes, or conjugates of any of the foregoing, whether such antigens or epitopes are isolated from natural sources or are synthetic derivatives or variants of the natural compounds.

Antibodies may be produced from any animal source, including birds and mammals. Particularly, the antibodies may be ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by this reference. These techniques are further described in: Marks (1992); Stemmer (1994); Gram et al. (1992); Barbas et al. (1994); and Schier et al. (1996).

Methods for producing polyclonal antibodies in various animal species, as well as for producing monoclonal antibodies of various types, including humanized, chimeric, and fully human, are well known in the art. Methods for producing these antibodies are also well known. For example, the following U.S. patents and patent publications provide enabling descriptions of such methods and are herein incorporated by reference: U.S. Patent publication Nos. 2004/0126828 and 2002/0172677; and U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; and 6,891,024. All patents, patent publications, and other publications cited herein and therein are hereby incorporated by reference in the present application.

It is fully expected that antibodies to AA3 and/or a 95-100 kDa form of AA3 will have the ability to neutralize or counteract the effects of the protein regardless of the animal species, monoclonal cell line or other source of the antibody. Certain animal species may be less preferable for generating therapeutic antibodies because they may be more likely to cause allergic response due to activation of the complement system through the "Fe" portion of the antibody. However, whole antibodies may be enzymatically digested into "Fe"

(complement binding) fragment, and into binding fragments having the binding domain or CDR. Removal of the Fc portion reduces the likelihood that the antigen binding fragment will elicit an undesirable immunological response and, thus, antibodies without Fc may be particularly useful for prophylactic or therapeutic treatments. As described above, antibodies may also be constructed so as to be chimeric, partially or fully human, so as to reduce or eliminate the adverse immunological consequences resulting from administering to an animral an antibody that has been produced in, or has sequences from, other species.

In some embodiments, the inhibitor is a peptide, polypeptide, or protein inhibitor. In some embodiments, the inhibitor is an antagonistic antibody.

C. Inhibitory Nucleic Acid

Inhibitory nucleic acids or any ways of inhibiting gene expression of AA3 known in the art are contemplated in certain embodiments. Examples of an inhibitory nucleic acid include but are not limited to siRNA (small interfering RNA), short hairpin RNA (shRNA), double-stranded RNA, an antisense oligonucleotide, a ribozyme, and a nucleic acid encoding thereof. An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. The nucleic acid may have nucleotides of at least or at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 50, 60, 70, 80, 90 nucleotides in length or any range derivable therefrom.

As used herein, "isolated" means altered or removed from the natural state through human intervention. For example, an siRNA naturally present in a living animal is not "isolated," but a synthetic siRNA, or an siRNA partially or completely separated from the coexisting materials of its natural state is "isolated." An isolated siRNA can exist in substantially purified form, or can exist in a non-native environment such as, for example, a cell into which the siRNA has been delivered.

In some embodiments, the nucleic acid inhibitor is comprises a modification, such as a chemical modification or a modified base. In some embodiments, one or more (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 (or any derivable range therein) of the nucleotide positions in one or both strands of an siRNA molecule are modified. Modifications include nucleic acid sugar modifications, base modifications, backbone (internucleotide linkage) modifications, non-nucleotide modifications, and/or any combination thereof. In certain instances, purine and pyrimidine nucleotides are differentially modified. For example, purine and pyrimidine nucleotides can be differentially modified at the 2'-sugar position (i.e., at least one purine has a different modification from at least one pyrimidine in the same or different strand at the 2'-sugar position). In other instances, at least one modified nucleotide is a 2'-deoxy-2'-fluoro nucleotide, a 2'-deoxy nucleotide, or a 2'-O-alkyl nucleotide. In certain embodiments, the siRNA molecule has 3' overhangs of one, two, three, or four nucleotide(s) on one or both of the strands. In other embodiments, the siRNA lacks overhangs (i.e., has blunt ends). The overhangs can be modified or unmodified. Examples of modified nucleotides in the overhangs include, but are not limited to, 2'-O-alkyl nucleotides, 2'-deoxy-2'-fluoro nucleotides, or 2'-deoxy nucleotides. The overhang nucleotides in the antisense strand can comprise nucleotides that are complementary to nucleotides in the AA3 gene target sequence. Likewise, the overhangs in the sense stand can comprise nucleotides that are in the AA3 target sequence. In certain instances, the siRNA molecules have two 3' overhang nucleotides on the antisense stand that are 2'-O-alkyl nucleotides and two 3' overhang nucleotides on the sense stand that are 2'-deoxy nucleotides.

In further embodiments, there are synthetic nucleic acids that are AA3 inhibitors. An inhibitor may be between 17 to 25 nucleotides in length and comprises a 5' to 3' sequence that is at least 90% complementary to the 5' to 3' sequence of a mature AA3 mRNA. In certain embodiments, an inhibitor molecule is 17, 18, 19, 20, 21, 22, 23, 24, or 25 nucleotides in length, or any range derivable therein. Moreover, an inhibitor molecule has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature AA3 gene mRNA, particularly a mature, naturally occurring mRNA such as the human sequence. The human sequence is set forth as mRNA in Accession Number BC008689.1, which is hereby incorporated by reference.

IV. Therapeutic Methods

A. Current Treatment Options for HCC

There are various approaches to the treatment of HCC but still the survival rates of advanced HCC patients have not significantly improved.

HCC is poorly chemosensitive due to the expression of drug resistance genes, and the liver dysfunction which hinders the delivery of drugs. In addition, cirrhosis has an impact on the drug distribution volumes.

Cytotoxic chemotherapy is used in treating HCC whether administered as a monotherapy of as a combination. Examples of drugs include but are not limited to doxorubicin, anthracyclines, 5-fluorouracil, fluoropyrimidines, capecitabine, gemcitabine, cisplatin and various combinations thereof.

Hormonal therapy is also used. As there is a significant male predominance in morbidity and mortality in HCC, it has long been considered that sex hormones play a role in its development. Some HCCs express estrogen receptors (ER) and estrogens have shown some protective effects against HCC. Examples of drugs used include tamoxifen, megestrol acetate, octreotide and others.

Molecularly targeted therapy includes sorafenib. Sorafenib is a small molecule inhibitor of several tyrosine protein kinases (TKI), such as VEGFR, platelet derived growth factor receptor (PDGFR) and Raf family kinases. It is a targeted drug that works in 2 ways. It help block tumors from forming new blood vessels, which they need to grow. It also targets some of the proteins on cancer cells that normally help them grow. It will inhibit growth of multiple kinases related to angiogenesis, cell proliferation and differentiation. In preclinical studies, sorafenib has shown antiproliferative effects in HCC cell lines. It also decreased tumor angiogenesis and tumor-cell signalling, increasing apoptosis in a mouse model. Sorafenib in combination with chemotherapy, or in combination with oxaliplatin is also used. Sorafenib is a pill that is taken orally, twice a day.

Additional examples of targeted therapy drugs include, but are not limited to, cabozantinib, regorafenib, CELESTIAL, lenvatinib, tivantinib, ramucirumab (a monoclonal anti-VEGFR-2 antibody), and apatinib. The current disclosure contemplates the use of any of such drugs in combination with the current methods and compositions described herein. Regorafenib is a targeted drug that blocks several proteins that normally either help tumor cells grow or help form new blood vessels to feed the tumor. The drug can be used to treat liver cancer, normally if sorafenib is no longer helpful. It is usually formulated to be taken as pills.

Immunotherapy is also used for the treatment of HCC. Immunotherapeutic drugs include, but are not limited to, pembrolizumab, nivolumab, tremelimumab, MEK inhibitors such as refametinib. Other small molecule c-MET inhibitors are also used or under study. Examples include foretinib, tepotinib, capmatinib, golvantinib and others.

Surgery with resectioning of a tumor or a liver transplant are also methods for current treatment of HCC depending on the stage of the disease.

Other methods include tumor ablation which is a treatment that destroys liver tumors without removing them. These techniques are used in patients with a few small tumors and when surgery is not a good option (often because of poor health or reduced liver function). They are less likely to cure the cancer than surgery, but they can still be very helpful for some people. These treatments are also sometimes used in patients waiting for a liver transplant.

Further methods for treating liver cancer includes embolization which is a procedure that injects substances to try to block or reduce the blood flow to cancer cells in the liver. The liver is unusual in that it has 2 blood supplies. Most normal liver cells are fed by branches of the portal vein, whereas cancer cells in the liver are usually fed by branches of the hepatic artery. Blocking the branch of the hepatic artery feeding the tumor helps kill off the cancer cells, but it leaves most of the healthy liver cells unharmed because they get their blood supply from the portal vein.

Embolization is an option for some patients with tumors that cannot be removed by surgery. It can be used for tumors that are too large to be treated with ablation (usually larger than 5 cm across). It can also be used with ablation. Embolization does reduce some of the blood supply to the normal liver tissue, so it may not be a good option for some patients whose liver has been damaged by diseases such as hepatitis or cirrhosis.

There are different kinds of radiation therapy that is used for treating liver cancer. External beam radiation therapy, focuses radiation delivered from outside the body on the cancer. This can sometimes be used to shrink liver tumors to relieve symptoms such as pain, but it is not used as often as other local treatments such as ablation or embolization. Although liver cancer cells are sensitive to radiation, this treatment can't be used at very high doses because normal liver tissue is also easily damaged by radiation. Stereotactic body radiation therapy (SBRT) is a technique that allows treatment to be completed in a short-time. Radiation therapy usually means getting small doses of radiation 5 days a week for several weeks, SBRT uses very focused beams of high-dose radiation given on one or a few days. Beams are aimed at the tumor from many different angles. To target the radiation precisely, the person is put in a specially designed body frame for each treatment. Radioemboliztion involve injecting small readioactive beads into the hepatic artery. They lodge in the liver near tumors and give off small amounts of radiation that travel only a short distance.

B. Treatment of Cancer in General

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the treatment methods described herein may be used in conjunction with removal of superficial cancers, precancers, or incidental amounts of normal tissue.

In some embodiments, the methods may further comprise a therapy described herein such as those described below.

Laser therapy is the use of high-intensity light to destroy tumor cells. Laser therapy affects the cells only in the treated area. Laser therapy may be used to destroy cancerous tissue and relieve a blockage in the esophagus when the cancer cannot be removed by surgery. The relief of a blockage can help to reduce symptoms, especially swallowing problems.

Photodynamic therapy (PDT), a type of laser therapy, involves the use of drugs that are absorbed by cancer cells; when exposed to a special light, the drugs become active and destroy the cancer cells. PDT may be used to relieve symptoms of esophageal cancer such as difficulty swallowing.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well. A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein). A patient may be administered a single compound or a combination of compounds described herein in an amount that is, is at least, or is at most 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

V. Formulations and Routes of Administration

In certain aspects, the compositions or agents for use in the methods, such as therapeutic agents or inhibitors, are suitably contained in a pharmaceutically acceptable carrier. The carrier is non-toxic, biocompatible and is selected so as not to detrimentally affect the biological activity of the agent. The agents in some aspects of the disclosure may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the disclosure also contemplate local administration of the compositions by coating medical devices, local administration, and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

In certain embodiments, an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 μg/kg/body weight, about 5 μg/kg/body weight, about 10 μg/kg/body weight, about 50 μg/kg/body weight, about 100 μg/kg/body weight, about 200 μg/kg/body weight, about 350 μg/kg/body weight, about 500 μg/kg/body weight, about 1 mg/kg/body weight, about 5 mg/kg/body weight, about 10 mg/kg/body weight, about 50 mg/kg/body weight, about 100 mg/kg/body weight, about 200 mg/kg/body weight, about 350 mg/kg/body weight, about 500 mg/kg/body weight, to about 1000 mg/kg/body weight or more per administration, and any range derivable therein. In non-limiting examples of a derivable range from the numbers listed herein, a range of about 5 μg/kg/body weight to about 100 mg/kg/body weight, about 5 g/kg/body weight to about 500 mg/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

The compositions may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antgifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, intralesional, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VI. Combination Therapies

The compositions and related methods, particularly the administration of AA3 inhibitors can also be used in combination with the administration of conventional HCC drugs for example or in combination with other methods of treatment of HCC as described above. In some embodiments, one or more AA3 inhibitors may be combined with traditional cancer therapy, such as curative resection, liver transplantation, radiofrequency ablation, trans-arterial chemoembolization, radioembolization and a systemic targeted agent like sorafenib. Treatment of HCC depends on several factors include tumor stage, patient performance status and liver function reserve. One or more of these may be combined with treatment involving one or more AA3 inhibitors. In some embodiments, they are co-formulated in a composition.

In one aspect, it is contemplated that therapy is used in conjunction with another treatment. Alternatively, the therapy may precede or follow the other agent treatment by intervals ranging from minutes to weeks. In embodiments where the other agents and/or a proteins or polynucleotides are administered separately, one would generally ensure that a significant period of time did not expire between the time of each delivery, such that the agent and antigenic composition would still be able to exert an advantageously combined effect on the subject. In such instances, it is contemplated that one may administer both modalities within about 12-24 h of each other or within about 6-12 h of each other. In some situations, it may be desirable to extend the time period for administration significantly, where several days (2, 3, 4, 5, 6 or 7) to several weeks (1, 2, 3, 4, 5, 6, 7 or 8) lapse between the respective administrations.

The methods and compositions may include chemotherapy, therapeutic agents, surgical removal of cancerous cells, radiation therapy, and combinations thereof. In some aspects, the treatment regimen excludes one or more of chemotherapy, therapeutic agents, surgical removal of cancerous cells and/or radiation therapy.

Various combinations of more than an anticancer modality, agent or compound (or a combination of such agents and/or compounds) may be employed, for example, a first anticancer modality, agent or compound is "A" and a second anticancer modality, agent or compound (or a combination of such modalities, agents and/or compounds) given as part of an anticancer therapy regime, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the compositions or therapeutic compounds or agents to a patient or subject will follow general protocols for the administration of such compounds, taking into account the toxicity, if any, of the current composition, or other compositions described herein. It is expected that the treatment cycles would be repeated as necessary. It also is contemplated that various standard therapies as well as surgical intervention may be applied in combination with the described therapy.

Radiation therapy that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Alternative cancer therapy include any cancer therapy other than surgery, chemotherapy and radiation therapy, such as immunotherapy, gene therapy, hormonal therapy or a combination thereof. Subjects identified with poor prognosis using the present methods may not have favorable response to conventional treatment(s) alone and may be prescribed or administered one or more alternative cancer therapy per se or in combination with one or more conventional treatments. (See above regarding liver specific therapies)

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

VII. Examples

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of particular embodiments, are exemplary, and are not intended as limitations on the scope of the invention. Changes therein and other uses which are encompassed within the spirit of the invention as defined by the scope of the claims will occur to those skilled in the art.

Example 1: Expression of AA3 in Primary Hepatocytes, HCC Cell Lines, Normal and HCC Livers All studied HCC cell lines (HuH1, HuH7, JHH5, JHH7, HLE, HCF and HepG2) expressed AA3 (FIG. 1). AA3 expression in HCC cell lines was 5 to 20 times greater than in normal primary hepatocytes (FIG. 1A). There were two AA3 bands of ~35 and 90-100 kDa (FIG. 1B). The immunostaining was blocked by pre-incubation of HR-C1 antibody with purified human AA3. The higher mobility band corresponded to the AA3 monomer (~35 kDa) that has been reported to be expressed in normal mammalian kidney and liver [32, 35-38]. The ~90-100 kDa band was detected in most HCC cell lines but not in normal hepatocytes (FIG. 1).

The inventors studied next the protein expression level of AA3 in normal liver and HCC livers. As shown in FIG. 2, AA3 protein is expressed mostly in hepatocytes with weak expression in biliary epithelial cells (FIG. 2). AA3 expression in normal liver was negative (−) to minimal (+) and was moderate (++) to high (+++) in HCC livers (FIG. 3).

Example 2: AA3 Deacetylates NAFC and NAGGC

Human AA3 efficiently deacetylates NAFC (FIG. 4a-d) and NAGGC (FIG. 4e-h) generating FC and GGC respectively. Kinetic parameters for these substrates ($K_m$: 0.025 and 0.14 mM; kcat: 2 and 7.2 s$^{-1}$ for NAFC and NAGGC, respectively) are similar to the other AA3 substrates, N-acetylated aromatic amino acids and mercapturic acids [30-33, 38,39].

AA1 (EC 3.5.1.14), in addition to AA3, has been reported to deacetylate certain mercapturic acids [36], although the substrate specificity of AA1 differed from AA3 [30-33, 39]. Therefore, we determined whether AA1 deacetylates NAFC and NAGGC. In experiments conducted by the inventors, rat AA1 that has high sequence identity with human AA1 did not significantly deacetylate these mercapturates: the specific activity was less than 0.1% of the corresponding value of AA3 and therefore the exact activity value could not be estimated (FIG. 5a).

Since HCC cell lines express the ~90-100 kDa form that may change the ability of AA3 to deacetylate NAFC and NAGGC, the inventors assayed (in the fluorescence assay) each of the mercapturates with AA3 immunoaffinity purified from HepG2 and HuH7 cells, and normal hepatocytes. AA3 from both cell lines deacetylated both mercapturates and N-acetyl-L-tyrosine with near similar specific activity (FIG. 5b) whereas the deacetylation rate of the substrates by the sample from normal hepatocytes was significantly lower. The amount of ~35 kDa AA3 form was very similar and small in all samples whereas the amount of ~90-100 kDa AA3 form in both HepG2 and HuH7 cells was ~50 times greater than of ~35 kDa form and this form was not expressed in normal hepatocytes. The finding and the significantly greater AA3 activity of HCC samples indicates that the ~90-100 kDa AA3 form is catalytically active and deacetylates NAFC and NAGGS.

Therefore, AA3 is likely responsible for the NAFC and NAGGC deacetylation in normal hepatocytes, and in HCC cell lines.

Example 3. Effect of AA3 Inhibitors on FC and NAFC Levels in HCC Cell Lines

The inventors' data suggest that AA3 deacetylates and therefore decreases the level of NAFC and NAGGC in HCC cells, and conversely AA3 inhibition should increase these levels. Accordingly, we measured NAFC and FC levels in HCC cells before and after treatment with AA3 inhibitors [33]. In untreated HepG2 and HuH7 cell lines, both FC and NAFC were detected; the level of FC in both cell lines was significantly higher than NAFC (FIG. 6). The FC level in HepG2 cells was higher than in HuH7 cells whereas the NAFC level in both cell lines was similar. Correspondingly the [FC]/[NAFC] ratio in HepG2 cells was slightly smaller (~2.6) then HepG2 cells (~3.7). Treatment with AA3 inhibitors 10 and 11 significantly increased the level of NAFC in both cell lines; the FC level was not significantly changed in HepG2 cell line, and in HuH7 cell lines decreased by approximately 50%. In the HepG2 cell line, the [FC]/[NAFC] ratio decreased from ~8.4 in untreated cells to ~1.6 and ~2.8 in cells treated with inhibitors 10 and 11 respectively. In HuH7 cells, the [FC]/[NAFC] ratio decreased from ~2.8 in untreated cells to ~0.85 and ~0.9 in cells treated with inhibitors 10 and 11 respectively. Therefore, the magnitude of changes in this ratio induced by inhibitors 10 and 11 in both cell lines was quite similar: 3.0-5.3 in HepG2 and 3.1-3.3 in HuH7 cells.

Example 4: AA3 Inhibitors and siRNA Decrease Membrane Associated Ras in HepG2 Cells The inventors tested next their prediction that AA3 inhibition as well as decreased AA3 synthesis should reduce Ras membrane association in HCC cells. Treatment of HepG2 cells with inhibitors 10 and 11 decreased levels of membrane associated Ras (FIG. 7a). Level of the membrane associated Ras with inhibitors 10 and 11 was decreased by ~50% of control.

Human AA3 siRNA also decreased levels of the membrane associated Ras in HepG2 and HUH7 cell lines (FIG. 7A,B). The reduction was greater in HUH7 than HepG2 cells The data indicated that AA3 inhibition or suppression of synthesis via RNA interference decreases the level of membrane associated Ras and therefore these treatments are toxic to HCC cells.

Figure 8:
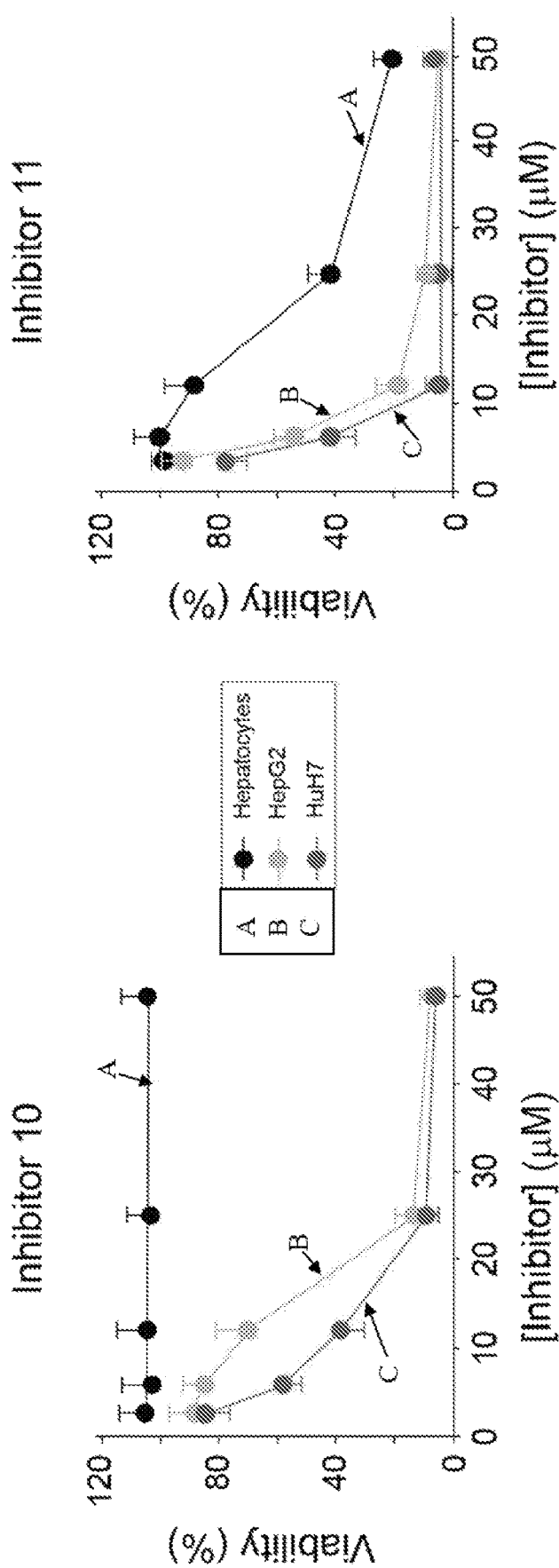
FIG. 8 Effect of AA3 inhibitors on the HepG2 and HuH7 cell viability.

Example 5: Effect of AA3 Inhibitors and siRNA on the Viability of HCC Cell Lines The viability of HCC cells in the presence of AA3 inhibitors was further studied. Inhibitors 10 and 11 were toxic to both HepG2 and HuH7 cell lines within the micromolar range (FIG. 8). Importantly inhibitor 10 was not toxic to normal primary hepatocytes in 0-50 μM range, and inhibitor 11 was significantly less toxic to normal cells in comparison with HCC cell lines.

Figure 7:
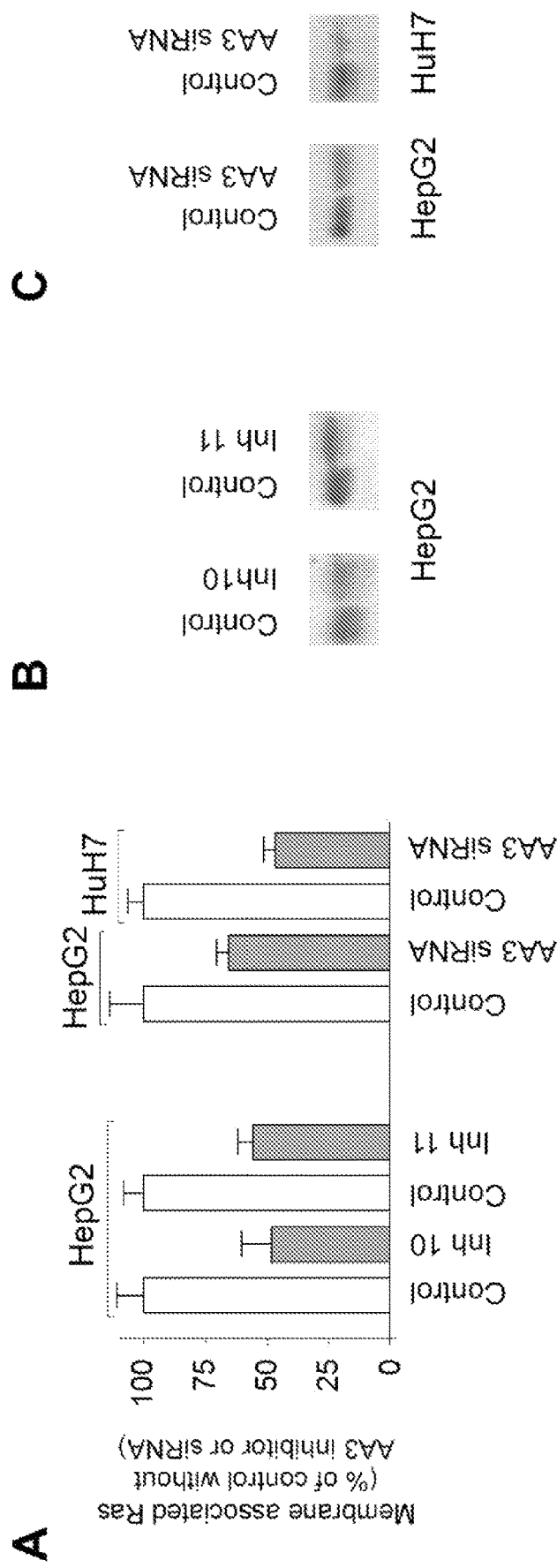
FIG. 7 (A) Levels of the membrane associated Ras in HepG2 and HuH7 cells treated with AA3 inhibitors 10 (Inh 10) and 11 (Inh 11), and AA3 siRNA. Control: untreated HepG2 cells (in study effect of inhibitors) or HepG2 and HuH7 cells treated with universal scrambled siRNA duplex (in study effect of AA3 siRNA). (B) Levels of the membrane associated Ras in HepG2 cells treated with inhibitors 10 and 11. Loading: 20 μg per lane. (C) HepG2 and HUH7 cells treated with universal scrambled siRNA duplex (control) and AA3 siRNA. Loading: 20 μg per lane.
Figure 9:
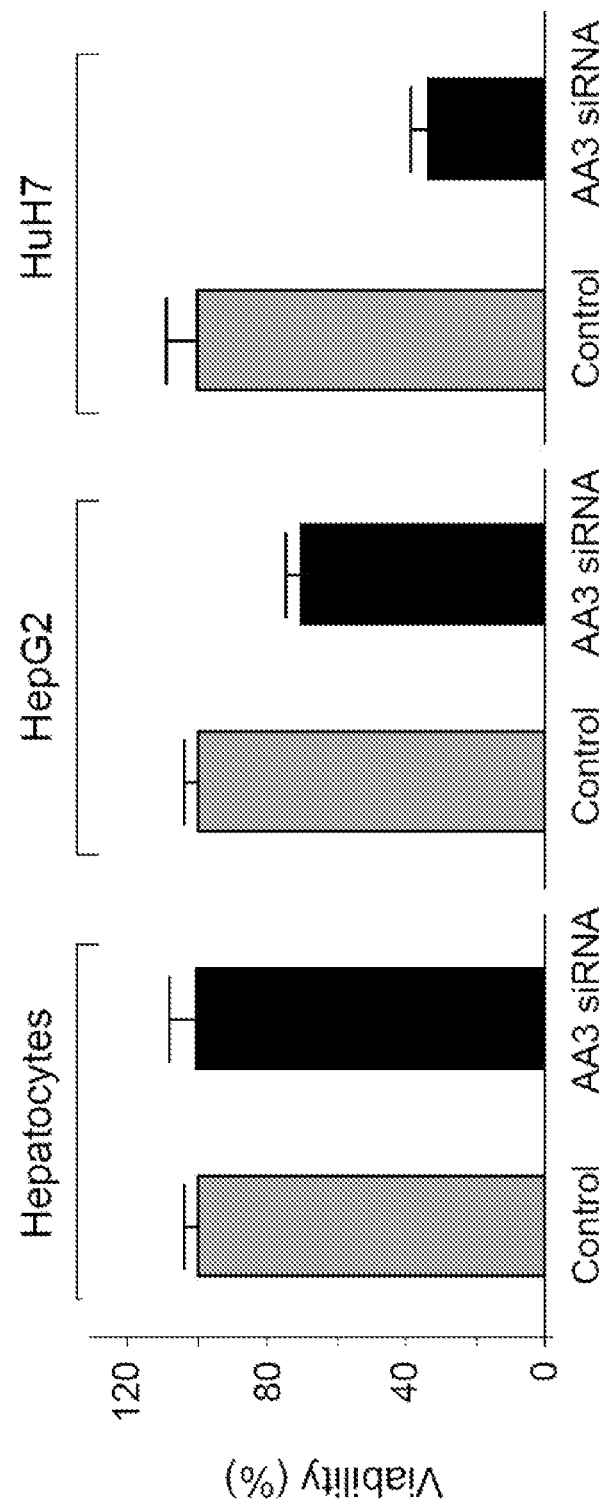
FIG. 9 Effect of AA3 siRNA on the viability of normal hepatocytes, HepG2 and HuH7 cells.
Figure 10:
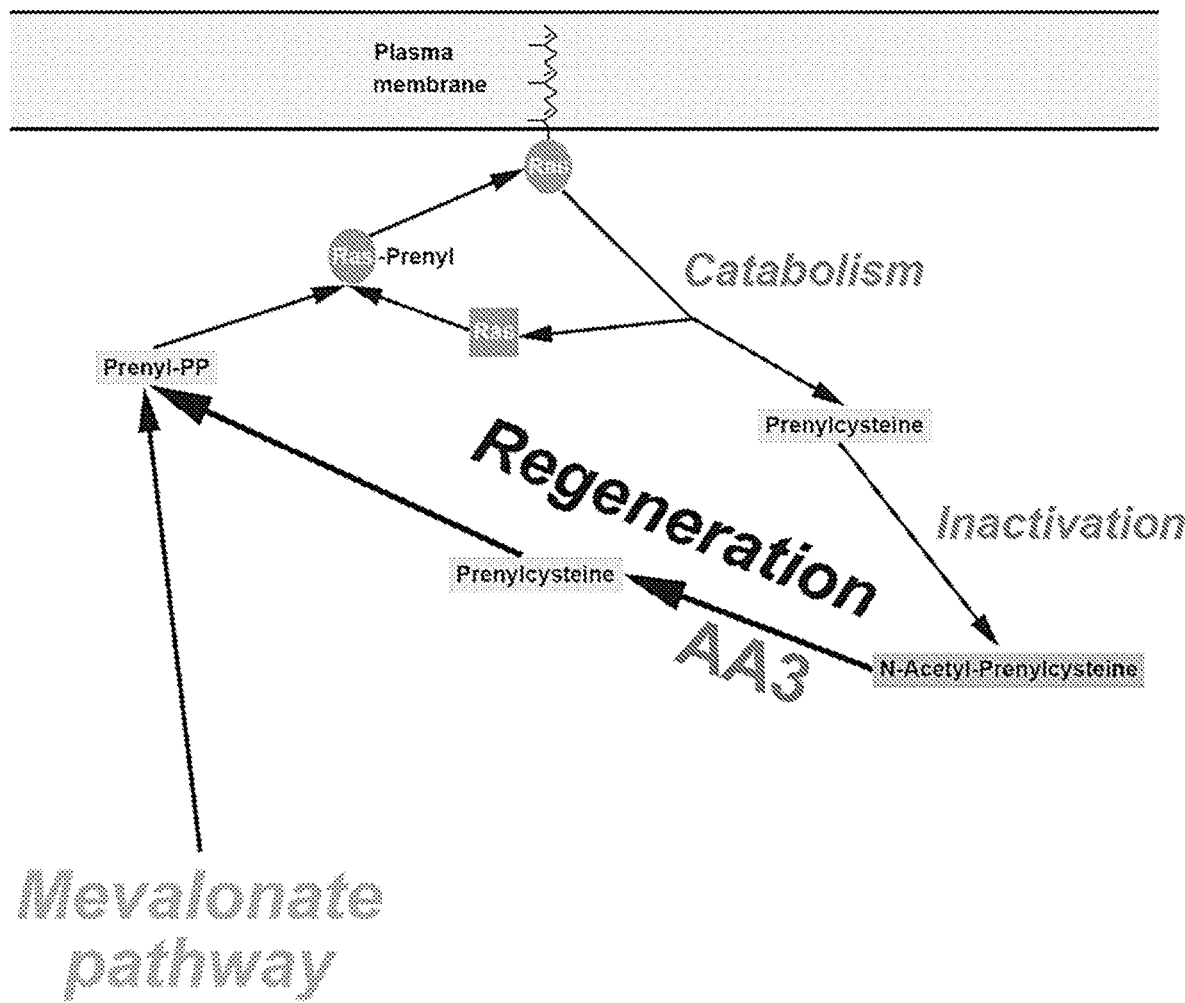
FIG. 10 Hypothetical mechanism of the AA3 initiated regeneration of prenyl-PP in HCC cells.

Suppression of AA3 with siRNA was also toxic to both HepG2 and HuH7 cell lines and not toxic to normal hepatocytes (FIG. 9) complementing the AA3 inhibition data (FIG. 7). In total, our findings These findings suggest that AA3 activity is more important for HCC cell survival than normal hepatocytes.

Example 6. Effect of AA3 Inhibitors in Colon and Pancreatic Cell Lines

AA3 inhibitors 10 and 21 suppress growth of the colon cancer cell lines expressing wild type (wt) or mutant (mut) KRas (FIG. 24). Inhibitors 3 and 11 suppress growth of the colon cancer cell lines expressing mutant (mut) KRas. AA3 inhibitors 3, 10, 11 and 21 are toxic for pancreatic normal and cancer cells. Inhibitors 10 and 21 are significantly less toxic for normal than cancer cell lines. Both inhibitors are efficient for the cell lines expressing either wild type (wt) or mutant (mut) KRas.

Example 7: Experimental Procedures

A. Cell Lines

Human HCC cell lines HuH1, HuH7, JHH5, JHH7, HLE, HLF, and HepG2 were obtained from ATCC (Manassas, Va.). The well-characterized HepG2 cell line was used in all experiments. The HuH7 cell line was also used in experiments to ensure the data was not specific only to the HepG2 cell line. Plated primary hepatocytes were obtained from Corning Life Sciences (Woburn, Mass.). HCC cell lines were cultured in DMEM medium containing 10% fetal bovine serum (FBS) and 1% penicillin-streptomycin (Life Technologies, Grand Island, N.Y.) at 37° C. and 5% $CO_2$. Primary hepatocytes were maintained in Williams Medium E with supplements (Corning Life Sciences) at 37° C. and 5% $CO_2$.

Human colon cancer cell lines COLO 205, HCT 116, LS 513 (all ATCC), primary colon epithelial cells (Cell Biologics), pancreatic cancer cell lines PANC-1, MIA PaCa-2, BxPC-3, and normal pancreatic duct epithelial cells (UCLA collection) were used in experiments. COLO 205, LS 513, BxPC-3 cells were cultivated in RPMI 1640 medium with 10% FBS, HCT 116 cells were cultivated in McCoy's 5A medium with 10% FBS, PANC-1 and MIA PaCa-2 cell lines were cultivated in DMEM medium with 10% FBS, and normal colon and pancreatic cells were maintained in Human Epithelial Cell Medium (Cell Biologics).

B. Measurement of AA3 and Prenylated Ras Expression in HCC Cell Lines

Cultured HCC cells and primary hepatocytes were washed with PBS buffer, treated with 0.25% Trypsin-EDTA solution (Corning) and precipitated at 1,000 rpm for 5 min. For protein extraction, HCC cells were lysed on ice by vortexing every 5 min for 30 min in RIPA buffer containing 20 mM Tris-HCl (pH 7.5), 150 mM NaCl, 5 mM EDTA, 1% Triton X-100, 0.5% sodium deoxycholate, 0.1% SDS, and 1× Halt protease inhibitor cocktail (Thermo Scientific, Waltham, Mass.). Prenylated Ras other membrane associated proteins were extracted from HCC cells using a Mem-PER Plus Kit (Thermo Scientific) according to the manufacturer's protocol. Protein extracts were resolved on 4-15% SDS-polyacrilamide gels (Bio-Rad, Hercules, Calif.), and proteins were electrotransferred to Hybond PVDF membranes (GE Healthcare Life Sciences, Piscataway, N.J.). Membranes were blocked with 5% non-fat dry milk (Bio-Rad) in PBST buffer (1×PBS with 0.05% Tween-20) followed by incubation with the primary antibody (1:1,000) for 1 h at room temperature. Our affinity purified polyclonal rabbit anti-human AA3 antibody HR-C130 was used for detection of human AA3. The antibody, pre-incubated for 1 h at 37° C. with 10 mg/ml purified recombinant human AA3, was used as a negative control. Rabbit polyclonal anti-Ras antibody 05-516, clone RAS10 (EMD Millipore, Gibbstown, N.J.) was used for detection of human Ras. After incubation with primary antibodies, membranes were washed with PBST buffer and incubated 30 min with horse radish peroxidase (HRP) conjugated goat anti-rabbit IgG (Jackson ImmunoResearch, West Grove, Pa.) at 1:5,000 dilution, washed with PBST, and developed with an ECL Western Blotting Detection Reagent (GE Healthcare).

Protein concentration in the samples was determined using a Micro-BCA Protein Assay Kit (Thermo Scientific).

C. Immunohistochemistry

Human normal and HCC liver samples were obtained under an Institutional Review Board approved protocol (#12-000647). Samples were fixed in 10% buffered formalin and embedded in paraffin blocks from which 4 am liver sections were transferred to slides. Slides were baked at 40° C. overnight in incubator, dewaxed in xylene and hydrated through an alcohol gradient (100%, 95%, 90%, 70%) and double distilled $H_2O$. For antigen retrieval slides were incubated at ~95° C. in 10 mM sodium citrate buffer (pH 6.0) for 20 min. The slides were then soaked in PBST and blocked with 1% goat serum (Vector labs, Burlingame, Calif.) in PBS for 1 h. Then slides were incubated for 1 h at 37° C. with HR-C1 antibody diluted 1:100 in PBS. After wash in PBS, slides were incubated at room temperature with a horse radish peroxidase (HRP) conjugated secondary goat anti-rabbit antibody (Jackson Immunoresearch) diluted 1:100 in PBS. After wash in PBS, slides were incubated with HRP substrate solution (Vector Labs, Burlingame, Calif.) for 45 s. The slides were counterstained in hematoxylin for 5 min and washed in running tap water. Finally, the slides were dried overnight, soaked in xylene and mounted in Permount. Slides without primary antibody incubation were used as negative controls. AA3 labeling was evaluated in a semi-quantitative manner, wherein the relative staining intensity was defined as negative (−), minimal (+), moderate (++) and high (+++).

D. Expression and Purification of Human AA3

Human normal and HCC liver samples were obtained under an Institutional Review Board approved protocol (#12-000647). Slides were baked at 40° C. overnight in incubator. Then they were blocked with 1% goat serum (Vector labs, Burlingame, Calif.) in PBS for 1 h. For antigen retrieval slides were incubated at ~95° C. in 10 mM sodium citrate buffer (pH 6.0) for 20 min. Then slides were incubated for 1 h at 37° C. with HR-C1 antibody diluted 1:100 in PBS. After wash in PBS, slides were incubated at room temperature with a horse radish peroxidase (HRP) conjugated secondary goat anti-rabbit antibody (Jackson Immunoresearch) diluted 1:100 in PBS. After wash in PBS, slides were incubated with HRP substrate solution (Vector Labs, Burlingame, Calif.) for 45 s. Slides without primary antibody incubation were used as negative controls.

E. Expression and Purification of Human AA3

Human N-terminally 6His-tagged AA3 was expressed in E. coli and purified to homogeneity as described previously [31]. Purified human AA3 on denaturing SDS-PAGE showed a single band of ~35 kDa and was ~99% homogeneous.

F. Rat Aminoacylase 1 (AA1)

Purified rat AA1 (EC 3.5.1.14) was purchased from (Sigma-Aldrich, St. Louis, Mo.).

G. Immunoaffinity Purification of AA3 from HepG2 and HuH7 Cells, and Normal Hepatocytes Because extracts from HepG2 and HuH7 cells and hepatocyte contained compounds that interfered with AA3 activity measurement in the fluorescent assay [32], we performed partial purification of AA3. HepG2 and HuH7 cells collected from two 10-cm plates (2-107 cells) or equal number of normal hepatocytes were lysed on ice for 20 min in 0.5 ml of 50 mM Na-phosphate buffer, pH 7.5, containing 0.1% Triton X-100, and 1× Halt protease inhibitor cocktail (Thermo Scientific). After centrifugation at 18,000 g for 20 min, the supernatant was incubated at 4° C. and constant rotation (5 rpm) for 1 h with our HR-C1 antibody immobilized on 10 µl of protein A Separose 4B-CL beads (GE HealthCare). To immobilize the anti-AA3 antibody, 2.0 ml protein A Separose 4B-Cl beads were incubated at 4° C. and rotated of 5 rpm for 1 h with 8 ml HR-C1 antibody (1 mg/ml) and washed 3 times with 10 ml of 50 mM sodium phosphate buffer.

H. AA3 Activity Fluorescent Assay

AA3 activity was measured using a previously described fluorescence assay [32]. Human purified AA3 (1 µg), rat AA1 (1 µg) or immunoaffinity purified AA3 from HepG2 and HuH7 cells were assayed for 30 min at 370 in 300 1 of 50 mM sodium phosphate buffer, pH 7.5, containing 1 mM NAFC or NAGGC both from Cayman Chemical (Ann Arbor, Mich.). Then 100 µl of the reaction mixture was added to 1 ml of 50 mM sodium phosphate buffer containing 1 mM fluorescamine, and fluorescence was measured (390 nm excitation, 475 nm emission).

In the control experiments boiled human AA3 and rat AA1 were used. In other control experiments, immunoaffinity beads not incubated with HCC cell or hepatocyte extracts were used.

I. Mass Spectrometry Study of the AA3 Mediated Deacetylation of NAFC and NAGGC

To study the deacetylation of NAFC and NAGGC mediated by AA3, 50 µl aliquots from the reaction assays were injected onto Agilent Eclipse Plus C18 reverse phase HPLC column equilibrated with 0.1% formic acid, and eluted with acetonitrile/0.1% formic acid gradient (0-90%, 20 min). The effluent from the column was passed to an Ionspray ion source connected to a triple quadrupole mass-spectrometer (MS) API III+(PerkinElmer, Boston, Mass.). NAFC and NAGGC (Cayman Chemical) were used for MS calibration.

J. AA3 Inhibitors

Our AA3 inhibitors [33] ($K_i$~1 µM) were used in HCC cell and normal hepatocyte assays, namely inhibitor 10: 2-phenyl-4H-1,3-benzothiazin-4-one (Specs, Hopkinton, R.I.) and inhibitor 11: 2-[(3-fluoro-4-methoxybenzyl)sulfanyl]-1-methyl-1H-benzimidazole-5-sulfonamide (Enamine, Monmouth Jct., N.J.).

K. Generation of FC and GGC

To generate authentic FC and GGC for chromatographic and MS calibration, 1 mM NAFC and NAGGC purchased from Cayman Chemical were hydrolyzed with purified recombinant human AA3 (0.03 mg/ml) in 50 mM Tris-HCl, pH 7.5 for 3 h at 37° C. Then FC and GGC were purified by reverse phase HPLC, dried and their identity was confirmed by MS and MS/MS.

L. Levels of FC and NAFC in HUH-7 and HepG2 Cells

HUH7 and HepG2 cells were seeded in 6-well plates at a density 250,000 cells per well in complete medium. Next day the medium was changed to 2 ml DMEM with 1% FBS containing a 10-20 µM AA3 inhibitor. After 24 h incubation, the medium was collected, concentrated 10 times on a vacuum concentrator; 10 µl aliquots were used for quantitation by LC/MS and LC/MS/MS-MRM. The cells were trypsinized, washed in PBS and centrifuged at 2,000 g for 10 min. Then cell pellet was lysed on ice in 50 µl of 20 mM Tris-HCl, pH 7.5, containing 1% dodecyl maltoside (DDM) and 1× protease inhibitor cocktail (Sigma/Aldrich). After centrifugation (14,000 g, 10 min) the supernatants were diluted 4 times with methanol and centrifuged (14,000 g, 10 min), then the supernatants were diluted 10 times with water, and 10 µl aliquots were used for quantitation by LC/MS and LC/MS/MS-MRM as described above expect electrospray ionization was used with an Agilent 6460 triple quadrupole mass spectrometer.

M. Effect of AA3 Inhibitors and siRNA on the Membrane Associated Ras in HCC Cells HepG2 cells were seeded in 6-well plates at a density 250,000 cells per well. Next day the cell medium was changed to DMEM, containing 1% FBS without or with AA3 inhibitors 10 and 11 (IC50~1 µM). 24 h later cells were collected, washed with PBS and the membrane associated Ras proteins were extracted as described above, resolved on SDS-PAGE, and detected with the anti-Ras antibody (EMD Millipore).

To study the effect of AA3 suppression on Ras membrane association, HepG2 and HuH7 cells seeded onto 6-well plates at the same density, were transfected with 50 pmol ACY3 (AA3) Silencer Select Pre-designed siRNA (Invitrogen, Grand Island, N.Y.) using the Lipofectamine RNAiMAX reagent (Invitrogen) following the manufacturer protocol. Universal scrambled siRNA duplex (OriGene, Rockville, Md.) was used as a negative control. After 48 h incubation, membrane associated proteins were extracted and membrane associated Ras was determined by immunoblotting as described above.

N. Toxicity of AA3 Inhibitors and siRNA to HCC, Colon and Pancreatic Cancer Cell Lines and Normal Cells HCC cell lines HepG2, HuH7, primary hepatocytes, colon cell lines COLO 205, HCT 116, LS 513, primary colon epithelial cells, pancreatic cancer cell lines PANC-1, MIA PaCa-2, BxPC-3, and normal pancreatic duct epithelial cells were seeded in 96-well plates at a density 10,000 cells per well in complete medium. Next day medium was changed to medium containing 1% FBS and an AA3 inhibitor (3-100 µM). 24 h later cell viability was determined using the MTT (3-(4,5-dimethylthiazol-2-yl)-2,5-diphenyltetrazolium bromide) cell viability assay [34]. Cells were incubated during 4 h at 37° C. with 150 µl fresh media containing 0.5 mg/ml MTT. Then 50 µl of 20% SDS in 25 mM HCl was added to each well, incubated for 4 h and the optical density at 570 nm was measured on a VMax Kinetic Microplate Reader (Molecular Devices, Sunnyvale, Calif.).

To study the effect of AA3 silencing, HepG2 and HUH7 cells seeded in 96-well plates were transfected with 2 pmol AA3 siRNA using the Lipofectamine RNAiMAX reagent as per the manufacturer protocol. Cell viability was measured in the MTT assay 48 h later as described.

O. Statistical Analysis

Experimental data are depicted as mean±SEM. 3-8 studies were performed in each experimental protocol.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references recited in the application, to the extent that they provide exemplary procedural or other details supplementary to those set forth herein, are specifically incorporated herein by reference.

REFERENCES

The following references and the publications referred to throughout the specification, to the extent that they provide exemplary procedural or other details supplementary to those set forth herein, are specifically incorporated herein by reference.

REFERENCES

1 Hobbs G A, Der C J, Rossman K L. RAS isoforms and mutations in cancer at a glance. J Cell Sci 2016; 129: 1287-1292.
2 Bos J L. Ras oncogenes in human cancer: a review. Cancer Res 1989; 49: 4682-4689.
3 Zhang F, Cheong J K. The renewed battle against RAS-mutant cancers. Cell Mol Life Sci 2016; 73: 1845-1858.
4 Ryan M B, Der C J, Wang-Gillam A, Cox A D. Targeting RAS-mutant cancers: is ERK the key? Trends Cancer 2015; 1: 183-198.
5 McCormick F. K-Ras protein as a drug target. J Mol Med (Berl) 2016; 94: 253-258.
6 Cox A D, Der C J, Philips M R. Targeting RAS membrane association: back to the future for anti-RAS drug discovery? Clin Cancer Res 2015; 21: 1819-1827.
7 Shaw R J, Cantley R C. Ras, PI(3)K and mTOR signaling controls tumour cell growth. Nature 2006; 441: 424-430.
8 Campbell S L, Khosravi-Far R, Rossman K L, et al. Increasing complexity of Ras signaling. Oncogene 1998; 17: 1395-1413.
9 Lowy D R, Willumsen B M. Function and regulation of Ras. Annu Rev Biochem 1993; 62:851-891.
10 Chetty R, Govender D. Gene of the month: KRAS. J Clin Pathol 2013; 66: 548-550.
11 Konstantinopoulos P A, Karamouzis M V, Papavassiliou A G. Post-translational modifications and regulation of the RAS superfamily of GTPases as anticancer targets. Nat Rev Drug Discov 2007; 6: 541-555.
12 Cox A D, Fesik S W, Kimmelman A C, et al. Drugging the undruggable RAS: Mission possible? Nat Rev Drug Discov 2014; 13: 828-851.
13 McCormick F. KRAS as a therapeutic target. Clin Cancer Res 2015; 21: 1797-1801.
14 Pasca di Magliano M, Logsdon C D. Roles for KRAS in pancreatic tumor development and progression. Gastroentherol 2013; 144: 1220-1229.
15 Huang H, Daniluk J, Liu Y, et al. Oncogenic K-Ras requires activation for enhanced activity. Oncogene 2014; 33: 532-535.
16 Downward J. Targeting RAS signaling pathways in cancer therapy. Nat Rev Cancer 2003; 3: 11-22.
17 Teufel A, Staib F, Kanzler S, et al. Genetics of hepatocellular carcinoma. World J Gastroenterol 2007; 13: 2271-2282.
18 Wong C M, Ng I O. Molecular pathogenesis of hepatocellular carcinoma. Liver Int 2008; 28: 160-174.
19 Villanueva A, Llovet J M. Targeted therapies for hepatocellular carcinoma. Gastroenterology 2011; 140: 1410-1426.
20 Sangiovanni A, Del Ninno E, Fasani P, et al. Increased survival of cirrhotic patients with a hepatocellular carcinoma detected during surveillance. Gastroenterology 2004; 126: 1005-1014.
21 El-Serag. (2011) Hepatocellular carcinoma. N Engl J Med 2011; 365: 1118-1127.
22 Zhang F L, Casey P J. Protein prenylation: molecular mechanisms and functional consequences. Annu Rev Biochem 1996; 65: 241-269.
23 Gao L, Liao J, Yang G Y. CAAX-box protein, prenylation process and carcinogenesis. Am J Transl Res 2009; 1: 312-325.
24 Whyte D B, Kirschmeier P, Hockenberry T N, et al. K- and N-Ras are geranylgeranylated in cells treated with farnesyl protein transferase inhibitors. J Biol Chem 1997; 272: 14459-14464.
25 Buhaescu I, Izzedine H. Mevalonate pathway: A review of clinical and therapeutical implications. Clin Biochem 2007; 40: 575-584.
26 Mullen P J, Yu R, Longo J, Archer M C, Penn L Z. The interplay between cell signaling and the mevalonate pathway in cancer. Nat Rev Cancer 2016; 16: 718-731.
27 Boroughs L K, DeBerardinis R J. Metabolic pathways promoting cancer cell survival and growth. Nat Cell Biol 2015; 17: 351-359.
28 Zhou Y Y, Zhu G Q, Wang Y, et al. Systematic review with network meta-analysis: statins and risk of hepatocellular carcinoma. Oncotarget 2016; 7: 21753-21762.
29 Svensson A W, Casey P J, Young S G, et al. Genetic and pharmacologic analyses of the role of Icmt in Ras membrane association and function. Methods Enzymol 2006; 407: 144-159.
30 Tsirulnikov K, Abuladze N, Newman D, et al. Mouse aminoacylase 3: A metalloenzyme activated by cobalt and nickel. Biochim Biophys Acta 2009; 1794: 1049-1057.
31 Hsieh J M, Tsirulnikov K, Sawaya M R, et al. Structures of aminoacylase 3 in complex with acetylated substrates. Proc Natl Acad Sci USA 2010; 107: 17962-17967.
32 Pushkin A, Carpenito G, Abuladze N, et al. Structural characterization, tissue distribution, and functional expression of murine aminoacylase III. Am J Physiol 2004; 286: C848-C856.
33 Tsirulnikov K, Abuladze N, Bragin A, et al. Inhibition of aminoacylase 3 protects rat brain cortex neuronal cells from the toxicity of 4-hydroxy-2-nonenal mercapturate and 4-hydroxy-2-nonenal. Toxicol Appl Pharmacol 2012; 263: 303-314.
34 Mosmann T. Rapid colorimetric assay for cellular growth and survival: application to proliferation and cytotoxicity assays. J Immunol Methods 1983; 65: 55-63.

35 Endo Y. N-acyl-1-aromatic amino acid deacylase in animal tissues. Biochim Biophys Acta 1978; 523: 207-214.

36 Suzuki S, Tateishi M. Purification and characterization of a rat liver enzyme catalyzing N-deacetylation of mercapturic acid conjugates. Drug Metab Dispos 1981; 9: 573-577.

37 Uttamsingh V, Anders M W. Acylase-catalyzed deacetylation of haloalkene-derived mercapturates. Chem Res Toxicol 1999; 12: 937-942.

38 Anders M W, Dekant W. Aminoacylases. Adv Pharmacol 1994; 27: 431-448.

39 Newman D, Abuladze N, Scholz K, et al. Specificity of aminoacylase III-mediated deacetylation of mercapturic acids. Drug Metab Dispos 2007; 35: 43-50.

40 Bentinger M, Griinler, J, Peterson E, et al. Phosphorylation of farnesol in rat liver microsomes: properties of farnesol kinase and farnesyl phosphate kinase. Arch Biochem Biophys 1998; 353: 191-198.

41 Chung Y T, Matkowskyj K A, Li H, et al. Overexpression and oncogenic function of aldo-keto reductase family 1B10 (AKR1B10) in pancreatic carcinoma. Mod Pathol 2012; 25: 758-766.

42 Long P M, Stradecki H M, Minturn J E, et al Differential aminoacylase expression in neuroblastoma. Int J Cancer 2011; 129: 1322-1330.

What is claimed is:

1. A method of treating hepatocellular carcinoma (HCC), pancreatic cancer or colon cancer in a subject comprising administering to the subject an effective amount of a composition comprising an AA3 inhibitor.

2. The method of claim 1, wherein the AA3 inhibitor inhibits AA3 activity or function.

3. The method of claim 1, wherein the AA3 inhibitor is at least one of the following:

a small molecules a small molecule selected from: a benzothiazinone, sulfonamide, thiazolidinone, chromenone, thiazole, thienopyrimidine, or (thiocyanatophenyl)carbamoyl cyclohexene, 2-(4-Methylphenyl)-1,2-benzothiazol-3-one, or a derivative, analog, or salt thereof;

2-Phenyl-4H-1,3-benzothiazin-4-one or 2-Phenyl-1,2-benzoselenazol-3(2H)-one, or a derivative, analog, or salt thereof;

a chromenone, or a derivative, analog, or salt thereof;

6-Chloro-3-(3-fluorobenzoyl)-4H-chromen-4-one and 7-Diethylamino-3-(5-pyridin-4-yl-[1,3,4]oxadiazol-2-yl)-chromen-2-one, or a derivative, analog, or salt thereof;

a thiazole, or a derivative, analog, or salt thereof;

4-Methyl-N-(6-methyl-5,6-dihydro-4H[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide, 342-(Benzylamino)-[2-oxoethyl]-1,3-benzothiazol-3-iumbromide, or a derivative, analog, or salt thereof;

a thienopyrmidine or a derivative, analog, or salt thereof;

8-(4-Methoxyphenyl)-9-sulfanyl-5,8-dihydronaphtho[2',1':4,5]thieno[2,3-d]pyrimidin-7(6H)-one or [2-(4-Methoxyphenyl)-5,6,7,8-tetrahydro[1]benzothieno[2,3-d]pyrimidin-4-yl]sulfanyIIacetic acid, or a derivative, analog, or salt thereof;

(thiocyanatophenyl)carbamoyl cyclohexene, or a derivative, analog, or salt thereof;

6-[(2-Bromo-4-thiocyanatophenyl)carbamoyl]-3-cyclohexene-1-carboxylic acid or 6-[(2-Chloro-4-thiocyanatophenyl)carbamoyl]-3-cyclohexene-1-carboxylic acid, or a derivative, analog, or salt thereof;

a sulfonamide, or a derivative, analog, or salt thereof;

2-(3 -Fluoro-[4-methoxybenzyl)sulfanyl]-1-methyl-1H-benzimidazole-5-sulfonamide (Inhibitor 11), 3 -Methyl-4-tetrazol-1-yl-N-(2-m-tolyl-ethyl)-b enzenesulfonamide, N-(2,3 -Dichloro-4-oxo-4H-naphthalen-1-ylidene)-benzenesulfonamide N-[(1E)-2,3 , 5-Trichloro-4-oxocyclohexa-2,5-dien-1-ylidene]benzenesulfonamide, or 4-Methyl-N'-(4-methylphenyl)benzenesulfonohydrazide, or a derivative, analog, or salt thereof;

a thiazolidinone, or a derivative, analog, or salt thereof;

(5Z)-5-(3-Bromo-2-hydroxy-5-nitrobenzylidene)-3-(2,4-dimethylphenyl)-2-thioxo-1,3-thiazolidin-4-one (Inhibitor 3), (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one, or (5E)-5-{ [5-(2-Bromophenyl)-2-furyl]methylene}-2-thioxo-1,3-thiazolidin-4-one, or a derivative, analog, or salt thereof;

4-Methyl-N-(6-methyl-5,6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3 -Benzenesulfonyl-1-(4-chlorophenyl)-3-furan-2-yl-propan-1-one, 1-Benzyl-3-[4-(2-pyridinyl)-1-piperazinyl]-2, 5 -pyrrolidinedione, N-(3-Cyano-4,5-dimethyl-2-thienyl)-2-[(7-ethyl [1,3 ] dioxolo[4, 5 -g]quinolin-6-yl)sulfanyl] acetamide, (5E)-5 -(2-Methoxybenzylidene)-1 -(1 -naphthyl)-2-thioxodihydro-4, 6(1H, 5H)-pyrimidinedione, (4E)-5-Methyl-4-{ [(4-nitrophenyl)amino]methylene}-2-phenyl-2,4-dihydro-3H-pyrazole-3-thione, 2-[(E)-(4H-1,2,4-Triazol-4-ylimino)methyl]-1-benzothiophene-3-ol, 2-(4-Methylphenyl)-1,2-benzothiazol-3 -one or 2-(4-ethoxyphenyl)-2-methyl succinic acid, or a derivative, analog, or salt thereof;

a compound with Formula I, or any derivative, analog, or salt thereof, wherein Formula I is:

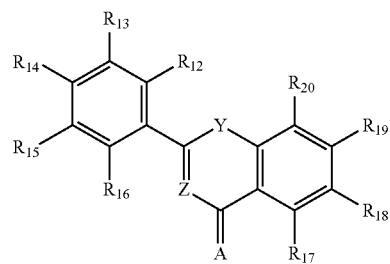

wherein X is O, S, CH$_2$, or NH; Z is N or CH; A is O, S, or NH; and each of R12-R20 independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula II, or any derivative, analog, or salt thereof, wherein Formula H is:

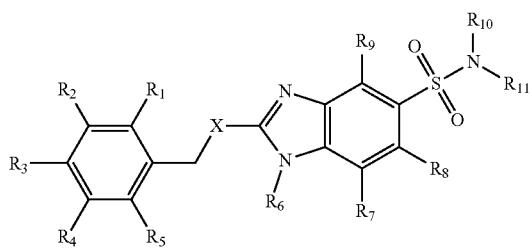

wherein X is O, S, CH2, or NH; and each of $R_1$-$R_{11}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula III, or any derivative, analog, or salt thereof, wherein Formula

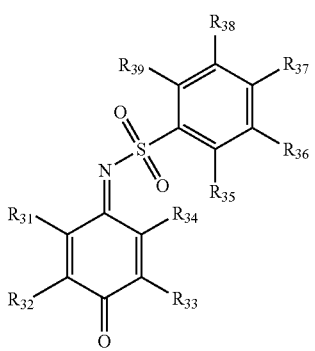

wherein B and C are each independently O, S, or NH, and each of $R_{21}$-$R_{30}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula IV, or any derivative, analog, or salt thereof, wherein Formula IV is:

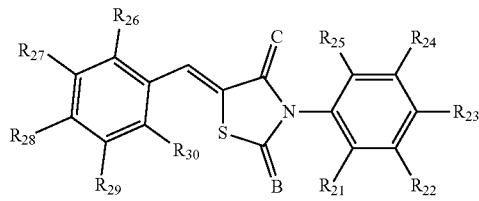

wherein each of $R_{31}$, $R_{32}$, and $R_{35}$-$R_{39}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

and $R_{33}$ and $R_{34}$ independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, or come together to form a carbocyclic or heterocyclic ring of 5 to 7 atoms;

a compound with Formula V, or any derivative, analog, or salt thereof, wherein Formula V is:

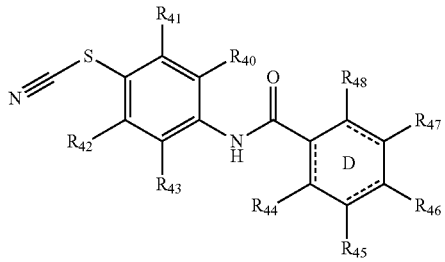

wherein each of $R_{40}$-$R_{48}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester; and the ring denoted by "D" may include one, two, or three carbon-carbon double bonds;

a compound with Formula VI, or any derivative, analog, or salt thereof, wherein Formula Vi 1S:

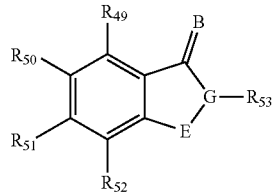

wherein each of $R_{49}$-$R_{52}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, $R_{53}$ is a substituted or unsubstituted aromatic ring, B is O or S, G is N or CH, and E is $CH_2$, NH, S, or Se, or a derivative, analog, or salt thereof;

2-Phenyl-4H-1,3-benzothiazin-4-one, 2-Phenyl-1,2-benzoselenazol-3(2H)-one, 6-Chloro-3-(3-fluorobenzoyl)-4H-chromen-4-one, 7-Diethylamino-3-(5-pyridin-4-yl-[1,3,4]oxadiazol-2-yl)-chromen-2-one, 4-Methyl-N-(6-methyl-5,6-dihydro-4H-[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide, 3-[2-(Benzylamino)-2-oxoethyl]-1,3-benzothiazol-3-ium bromide, 8-(4-Methoxyphenyl)-9-sulfanyl-5,8-dihydronaphtho[2', 1':4,5]thieno[2,3-d]pyrimidin-7(6H)-one, { [2-(4-Methoxyphenyl)-5,6,7,8-tetrahydro[1]benzothieno[2,3-d]pyrimidin-4-yl]sulfanyl }acetic acid, 6-[(2-Bromo-4-thiocyanatophenyl)carbamoyl]-3-cyclohexene-1-carboxylic acid, 6-[(2-Chloro-4-thiocyanatophenyl)carbamoyl]-3-cyclohexene-1-carboxylic acid, 2-[(3-Fluoro-4-methoxybenzyl)sulfanyl]-1-methyl-1H-benzimidazole-5-sulfonamide (Inhibitor 11), 3-Methyl-4-tetrazol-1-yl-N-(2-m-tolyl-ethyl)-benzenesulfonamide, N-(2,3 -Dichloro-4-oxo-4H-naphthalen-1-ylidene)-b enzenesulfonamide N-[(1E)-2,3,5-Trichloro-4-oxocyclohexa-2,5-dien-1-ylidene] benzenesulfonamide, 4-Methyl-N'-(4-methylphenyl)

benzenesulfonohydrazide, (5Z)-5-(3-Bromo-2-hydroxy-5-nitrobenzylidene)-3-(2,4-dimethylphenyl)-2-thioxo-1,3-thiazolidin-4-one (Inhibitor 3), (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one, (5E)-5-{ [5 -(2-Bromophenyl)-2-furyl]methylene } -2-t hioxo-1,3-thiazolidin-4-one, 4-Methyl-N-(6-methyl-5, 6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3-Benzenesulfonyl-1-(4-chloro-phenyl)-3-furan-2-yl-propan-1-one, 1-Benzyl-344-(2-pyridinyl)-[1-piperazinyl]-2,5-pyrrolidinedione, N-(3-Cyano-4,5-dimethyl-2-thienyl)-2-[(7-ethyl[1,3]dioxolo[4,5-g]quinolin-6-yl)sulfanyl]acetamide, (5E)-5-(2-Methoxybenzylidene) -1-(1 -naphthyl)-2-thioxodihydro-4,6(1H, 5H)-pyrimidinedione, (4E)-5-Methyl-4-{ [(4-nitrophenyl)amino]methylene} -2-phenyl-2,4-dihydro-3H-pyrazole-3 -thione, 2-[(E)-(4H- 1,2,4-Triazol-4-ylimino) methyl] -1-benzothiophene-3-ol, 2-(4-ethoxyphenyl)-2-methyl succinic acid, or any derivative, analog, or salt thereof; or 2-(4-methylphenyl)-1,2-benzothiazol-3-one or 2-phenyl-1,2-benzoselenazol-3(2H)-one.

4. The method of claim 1, wherein the composition is immunotherapeutic.

5. The method of claim 4, wherein the composition comprises anti- AA3 antibodies.

6. The method of claim 1, wherein the AA3 inhibitor reduces the expression of AA3 nucleic acids.

7. The method of claim 1, wherein the composition is a pharmaceutical formulation.

8. The method of claim 7, wherein the formulation is at least one of the following:

administered systematically,. administered orally, intravenously, tumorally, parenterally, subcutaneously, or intramuscularly;

administered locally;

administered via a targeted drug delivery system; or administered via a liver-targeted or an intrahepatic-targeted drug delivery system.

9. The method of claim 7, wherein the pharmaceutical formulation comprises a carrier.

10. The method of claim 1, wherein the method further comprises administration of an additional cancer therapy.

11. The method of claim 10, wherein the additional therapy comprises at least one of the following:

tumor ablation therapy, embolization therapy, radiation therapy, chemotherapy, liver-targeted therapy, or surgery; or sorafenib and/or regorafenib.

12. The method of claim 1, wherein the subject is one of either a mammal or a human.

13. A method of reducing or inhibiting hepatocellular carcinoma (HCC) growth or proliferation in a subject comprising administering to the subject an effective amount of a composition comprising an AA3 inhibitor.

14. The method of claim 13, wherein the AA3 inhibitor inhibits AA3 activity or function.

15. The method of claim 13, wherein the AA3 inhibitor is at least one of the following:

a small molecule;

a benzothiazinone, sulfonamide, thiazolidinone, chromenone, thiazole, thienopyrimidine, or (thiocyanatophenyl)carbamoyl cyclohexene, or a derivative, analog, or salt thereof;

a benzothiazinone, or a derivative, analog, or salt thereof;

2-Phenyl-4H-1,3-benzothiazin-4-one or 2-Phenyl-1,2-benzoselenazol-3(2H)-one, or a derivative, analog, or salt thereof;

a chromenone, or a derivative, analog, or salt thereof;

6-Chloro-3-(3-fluorobenzoyl)-4H-chromen-4-one and 7-Diethylamino-3-(5-pyridin-4-yl-[1,3,4]oxadiazol-2-yl)-chromen-2-one, or a derivative, analog, or salt thereof;

a thiazole, or a derivative, analog, or salt thereof;

4-Methyl-N-(6-methyl-5,6-dihydro-4H-[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide, 3-[2-(Benzylamino) -2-oxoethyl]-1,3-benzothiazol-3-ium bromide, or a derivative, analog, or salt thereof;

a thienopyrmidine or a derivative, analog, or salt thereof;

8-(4-Methoxyphenyl)-9-sulfanyl-5,8-dihydronaphtho[2', 1':4,5]thieno[2,3-d]pyrimidin-7(6H)-one or {[2-(4-Methoxyphenyl)-5,6,7,8-tetrahydro[1]benzothieno[2,3-d]pyrimidin-4-yl]sulfanyl }acetic acid, or a derivative, analog, or salt thereof;

A (thiocyanatophenyl)carbamoyl cyclohexene, or a derivative, analog, or salt thereof;

6-[(2-Bromo-4-thiocyanatophenyl)carbamoyl]-3-cyclohexene-1-carboxylic acid or 6-[(2-Chloro-4-thiocyanatophenyl)carbamoyl]-3-cyclohexene-1-carboxylic acid, or a derivative, analog, or salt thereof;

a sulfonamide, or a derivative, analog, or salt thereof;

2-(3 -Fluoro-[4-methoxybenzyl)sulfanyl]-1-methyl-1H-b enzimidazole-5-sulfonamide (Inhibitor 11), 3-Methyl-4-tetrazol-1-yl-N-(2-m-tolyl-ethyl)-benzenesulfonamide, N-(2,3-Dichloro-4-oxo-4H-naphthalen-1-ylidene)-b enzenesulfonamide N-[(1E)-2,3,5-Trichloro-4-oxocyclohexa-2,5-dien-1-ylidene] benzenesulfonamide, or 4-Methyl-N'-(4-methylphenyl) benzenesulfonohydrazide, or a derivative, analog, or salt thereof;

a thiazolidinone, or a derivative, analog, or salt thereof;

(5Z)-5-(3-Bromo-2-hydroxy-5-nitrobenzylidene)-3-(2,4-dimethylphenyl)-2-thioxo-1,3-thiazolidin-4-one (Inhibitor 3), (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one, or (5E)-5-{ [5-(2-Bromophenyl)-2-furyl]methylene}-2-thioxo-1,3-thiazolidin-4-one, or a derivative, analog, or salt thereof;

4-Methyl-N-(6-methyl-5,6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3-Benzenesulfonyl-1-(4-chlorophenyl)-3-furan-2-yl-propan-1-one, 1-Benzyl-3-[4-(2-pyridinyl)-1-piperazinyl]-2,5-pyrrolidinedione, N-(3-Cyano-4,5-dimethyl-2-thienyl)-2-[(7-ethyl[1,3]dioxolo[4,5-g]quinolin-6-yl)sulfanyl]acetamide, (5E)-5-(2-Methoxybenzylidene)-1-(1-naphthyl)-2-thioxodihydro-4, 6(1H, 5H)-pyrimidinedione, (4E)-5-Methyl-4-{ [(4-nitrophenyl)amino]methylene}-2-phenyl-2,4-dihydro-3H-pyrazole-3-thione, 2-[(E)-(4H-1,2,4-Triazol-4-ylimino)methyl]-1-benzothiophene-3- ol, or 2-(4-ethoxyphenyl)-2-methylsuccinic acid, or a derivative, analog, or salt thereof;

a compound with Formula I, or any derivative, analog, or salt thereof, wherein Formula I is:

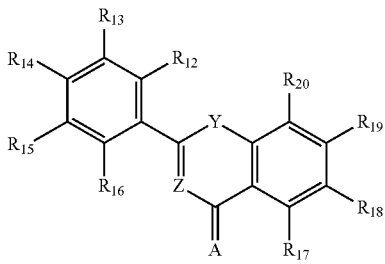

wherein X is O, S, $CH_2$, or NH; Z is N or CH; A is O, S, or NH; and each of $R_{12}$-$R_{20}$ independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula II, or any derivative, analog, or salt thereof, wherein Formula II is:

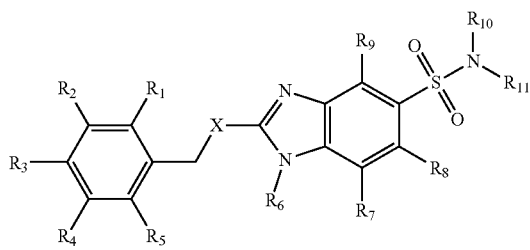

wherein X is O, S, $CH_2$, or NH; and each of $R_1$-$R_{11}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula III, or any derivative, analog, or salt thereof, wherein Formula III is:

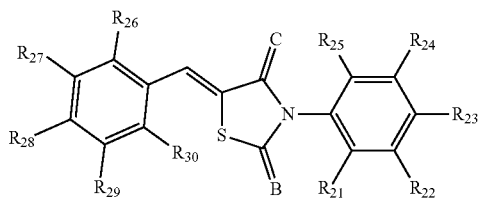

wherein B and C are each independently O, S, or NH, and each of $R_{21}$-$R_{30}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester;

a compound with Formula IV, or any derivative, analog, or salt thereof, wherein Formula IV is:

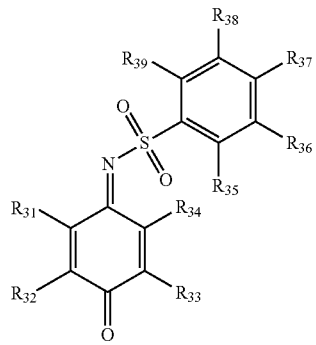

wherein each of $R_{31}$, $R_{32}$, and $R_{35}$-$R_{39}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester; and $R_{33}$ and $R_{34}$ independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, or come together to form a carbocyclic or heterocyclic ring of 5 to 7 atoms;

a compound with Formula V, or any derivative, analog, or salt thereof, wherein Formula V is:

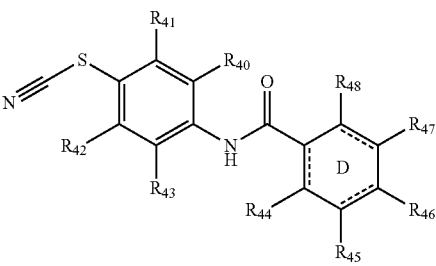

wherein each of $R_{40}$-$R_{48}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester; and the ring denoted by "D" may include one, two, or three carbon-carbon double bonds;

a compound with Formula VI, or any derivative, analog, or salt thereof, wherein Formula VI is:

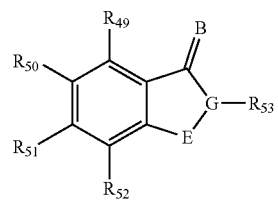

wherein each of $R_{49}$-$R_{52}$ is independently hydrogen, hydroxyl, alkoxy, halide, alkyl, alkenyl, alkynyl, cycloalkyl, cycloalkenyl, heterocycyl, aryl, heteroaryl, alkylaryl, alkylheteroaryl, sulfonyl, sulfonate, sulfonamide, nitrate, carbamate, or carboxylic acid or ester, $R_{53}$ is a substituted or unsubstituted aromatic ring, B is O or S, G is N or CH, and E is CH$_2$, NH, S, or Se, or a derivative, analog, or salt thereof;

2-Phenyl-4H-1,3-benzothiazin-4-one, 2-Phenyl-1,2-benzoselenazol-3 (2H)-one, 6-Chloro-3-(3-fluorobenzoyl)-4H-chromen-4-one, 7-Diethylamino-3-(5-pyridin-4-yl[4 1,3,4] oxadiazol-2-y1)-chromen-2-one, 4-Methyl-N-(6-methyl-5,6-dihydro-4H-[1,3]thiazolo[4,5-e]indazol-2-yl)-1,3-thiazole-5-carboxamide, N-[(4-Methoxyphenyl)(4-pyridinyl)methyl]-2-methyl-1,3-benzothiazole-6-carboxamide, 2-(1,3-Benzothiazol-2-ylsulfanyl)ethanamine hydrobromide, 3-[2-(Benzylamino)-2-oxoethyl]-1,3-benzothiazol-3-iumbromide, 8-(4-Methoxyphenyl)-9-sulfanyl-5, 8-dihydronaphtho[2', 1' :4,5 ]thieno[2,3-d]pyrimidin-7 (6H)-one, { [2-(4-Methoxyphenyl)-5, 6,7, 8-tetrahydro[ 1 ]benzothieno[2,3-d]pyrimidin-4-yl] sulfanyl } acetic acid, 6-[(2-Bromo-4-thiocyanatophenyl) carbamoyl]-3-cyclohexene-1-carboxylic acid, 6-[(2-Chloro-4-thiocyanatophenyl)carbamoyl]-3-cyclohexene-1-carboxylic acid, 2-[(3-Fluoro-4-methoxybenzyl)sulfanyl]-1-methyl-1H-benzimidazole-5-sulfonamide (Inhibitor 11), 3-Methyl-4-tetrazol-1-yl-N-(2-m-tolyl-ethyl)-benzenesulfonamide, N-(2,3-Dichloro-4-oxo-4H-naphthalen-1-ylidene)-benzenesulfonamideN-[(1E)-2,3, 5-Trichloro-4-oxocyclohexa-2, 5-dien-1-ylidene]benzenesulfonohydrazide, 4-Methyl-N'-(4-methylphenyl)benzenesulfonohydrazide, (5Z)-5-(3-Bromo-2-hydroxy-5-nitrobenzylidene)-3-(2,4-dimethylphenyl)-2-thioxo-1,3-thiazolidin-4-one(Inhibitor 3), (5Z)-5-(3-Bromo-2-hydroxy-5-nitrobenzylidene)-3-(3-fluorophenyl)-2-thioxo-1,3-thiazolidin-4-one, (5Z)-5-(3-Bromo-2-hydroxy-5-nitrobenzylidene)-3-(3-methylphenyl)-2-thioxo-1,3-thiazolidin-4-one, (5E)-5-{ [5-(2-Bromophenyl)-2-furyl]methylene }-2-thioxo-1,3-thiazolidin-4-one, 4-Methyl-N-(6-methyl-5,6-dihydro-4H-[1,3]thiazolo[4,5-e]indazol-2-yl)-1,3-thiazole-5-carboxamide, 4-[(4-Methoxybenzoyl)amino]-N-(4-methylphenyl)-1-piperidinecarboxamide, 3-Benzenesulfonyl-1-(4-chloro-phenyl)-3-furan-2-yl-propan-1-one, 1-Benzyl-344-(2-pyridinyl)-[1-piperazinyl]-2,5-pyrrolidinedione, N-(3-Cyano-4,5-dimethyl-2-thienyl)-2-[(7-ethyl[1,3]dioxolo[4,5-g]quinolin-6-yl) sulfanyl]acetamide, (5E)-5-(2-Methoxybenzylidene)-1-(1-naphthyl)-2-thioxodihydro-4,6(1H,5H)-pyrimidinedione, (4E)-5-Methyl-4-{[(4-nitrophenyl) amino]methylene}-2-phenyl-2,4-dihydro-3H-pyrazole-3-thione, 2-[(E)-(4H-1,2,4-Triazol-4-ylimino)methyl]-1-benzothiophene-3-ol, 2-(4-ethoxyphenyl)-2-methyl succinic acid, or any derivative, analog, or salt thereof;

2-(4-methylphenyl)-1,2-benzothiazol-3-one or 2-phenyl-1,2-benzoselenazol-3(2H)-one; or an siRNA.

16. The method of claim 13, wherein the composition is immunotherapeutic.

17. The method of claim 16, wherein the composition comprises anti-AA3 antibodies.

18. The method of claim 13, wherein the AA3 inhibitor reduces the expression of AA3 nucleic acids.

19. The method of claim 15, wherein the composition is a pharmaceutical formulation.

20. The method of claim 19, wherein the formulation is delivered via a drug delivery system that targets HCC cells but not normal cells.

21. The method of claim 19, wherein the formulation is at least one of the following:
administered systematically;
administered orally, intravenously, intratumorally, parenterally, subcutaneously, or intramuscularly; or
administered locally.

22. The method of claim 15, wherein the method further comprises administration of an additional cancer therapy.

23. The method of claim 22, wherein the additional therapy comprises at least one of the following:
tumor ablation therapy, embolization therapy, radiation therapy, chemotherapy, liver-sorafenib targeted therapy, or surgery; or and/or regorafenib.

24. The method of claim 13, wherein the subject is a mammal or a human.

* * * * *

UNITED STATES PATENT AND TRADEMARK OFFICE
CERTIFICATE OF CORRECTION

PATENT NO. : 11,464,784 B2
APPLICATION NO. : 16/646975
DATED : October 11, 2022
INVENTOR(S) : Kurtz et al.

It is certified that error appears in the above-identified patent and that said Letters Patent is hereby corrected as shown below:

In the Specification

Column 40, Line 67, Please delete "H" and insert -- II -- therefore.

Column 41, Line 20, Please delete "Formula" and insert -- Formula III is --.

Column 42, Line 24, Please delete "Vi 1S:" and insert -- VI is: -- therefore.

Column 43, Line 39, Please delete ",." and insert -- ; -- therefore.

Signed and Sealed this
Twenty-seventh Day of December, 2022

Katherine Kelly Vidal
*Director of the United States Patent and Trademark Office*